US007758855B2

(12) United States Patent
Kopecko et al.

(10) Patent No.: US 7,758,855 B2
(45) Date of Patent: Jul. 20, 2010

(54) DNA PROMOTERS AND ANTHRAX VACCINES

(75) Inventors: Dennis J. Kopecko, Silver Spring, MD (US); Manuel Osorio, Bethesda, MD (US); Siba Bhattacharyya, Bethesda, MD (US); Chandrakant P. Giri, Rockville, MD (US); Milan Blake, Fulton, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 11/378,003

(22) Filed: Mar. 17, 2006

(65) Prior Publication Data

US 2010/0150965 A1    Jun. 17, 2010

Related U.S. Application Data

(63) Continuation of application No. PCT/US2004/030616, filed on Sep. 20, 2004.

(60) Provisional application No. 60/504,505, filed on Sep. 18, 2003, provisional application No. 60/504,504, filed on Sep. 18, 2003.

(51) Int. Cl.
    A61K 48/00    (2006.01)
    C12N 15/74   (2006.01)
    C12N 1/20    (2006.01)
(52) U.S. Cl. .............. 424/93.2; 435/471; 435/252.8
(58) Field of Classification Search .................. None
    See application file for complete search history.

(56) References Cited

U.S. PATENT DOCUMENTS

| 4,632,830 | A | 12/1986 | Formal et al. |
| 5,066,596 | A | 11/1991 | Manning et al. |
| 6,500,419 | B1 * | 12/2002 | Hone et al. ............... 424/93.2 |
| 6,610,836 | B1 | 8/2003 | Breton et al. |
| 6,770,479 | B1 * | 8/2004 | Lee et al. ................ 435/456 |
| 2004/0197343 | A1 * | 10/2004 | Dubensky et al. ........ 424/184.1 |
| 2005/0281841 | A1 | 12/2005 | Kopecko et al. |

FOREIGN PATENT DOCUMENTS

| WO | WO 93/11220 A1 | 6/1993 |
| WO | WO 98/48026 A1 | 10/1998 |
| WO | WO99/39735 * | 8/1999 |
| WO | WO 00/02522 | 1/2000 |
| WO | WO 01/19974 | 3/2001 |
| WO | WO 01/70955 A2 | 9/2001 |
| WO | WO 02/04646 | 1/2002 |
| WO | WO 02/34773 A2 | 5/2002 |

OTHER PUBLICATIONS

McClelland et al. Nature. vol. 413. (Oct. 20, 2001). pp. 852-856.*
Cardenas et al. (Clinical Microbiology Reviews, vol. 5, No. 3; Jul. 1992, p. 328-342).*
Wood et al. (Cellular Microbiology. 2000, 2(4): 293-303).*
Heinzinger et al. (J. Bacteriology. May 1995, vol. 177, No. 10: 2813-2820).*
Everest et al. (FEMS Microbiol. Lett., Feb. 1995; 126(1): 97-101).*
Galen et al. (Trends in Microbiology. Aug. 2001; 9(8): 372-376).*
Baud, D. et al. 2004 "Immunogenicity against human papillomavirus type 16 virus-like particles is strongly enhanced by the PhoP$^c$ phenotype in *Salmonella enterica* serovar *typhimurium.*" *Infect. Immun.* 72:750-756.
Besser T.E. et al. 1997 "Salmonellosis associated with *S. typhimurium* DT104 in the USA." *Vet. Rec.* 140:75.
Burke, C.J. et al. 1999 "Formulation, stability, and delivery of live attenuated vaccines for human use." *Critical Rev. in Therapeutic Drug Carrier Sys.* 16:1-83.
Clarke, R.C. et al. 1986 "Galactose epimeraseless mutants of *Salmonella typhimurium* as live vaccines for calves" *Can. J. Veterinary Res.* 50:165-173.
Cryz, S.J., Jr. et al. 1996 "Factors influencing the stability of live oral attenuated bacterial vaccines." *Dev. Biol. Stand.* 87:277-281.
Dilts, D.A et al. 2000 "Phase I clinical trials of *aroA aroD* and *aroA aroD htrA* attenuated *S. typhi* vaccines; effect of formulation on safety and immunogenicity." *Vaccine* 18:1473-1484.
Dixon, T.C. et al. 1999 "Anthrax." *New Engl. J. Med.* 341:815-826.
EBI Database Accession # AAS56086, Feb. 13, 2002.
Evans S. et al. 1996 "Case control study of multiple-resistant *Salmonella typhimurium* DT104 infection of cattle in Great Britain." *Vet. Rec.* 139: 557-558.
Farchaus, J.W. et al. 1998 "Fermentation, purification, and characterization of protective antigen from a recombinant, avirulent strain of *Bacillus anthracis.*" *Appl. Environ. Microbiol.* 64:982-991.
Flick-Smith, H.C. et al. 2002 "Mucosal or parenteral administration of microsphere-associated *Bacillus anthracis* protective antigen protects against anthrax infection in mice." *Infect. Immun.* 70:2022-2028.
Friedlander, A.M. et al. 2002 "Anthrax Vaccines" *Curr. Top. Microbiol. Immunol.* 271:33-60.
Garmory, H.S. et al. 2003 "*Salmonella enterica* serovar *typhimurium* expressing a chromosomally integrated the *Bacillus anthracis* protective antigen gene protects mice against an anthrax spore challenge." *Infect. Immun.* 71:3831-3836.
Gentschev, I. et al. 1996 "Development of antigen-delivery systems, based on the *Escherichia coli* hemolysin secretion pathway." *Gene* 179:133-140.
Gentschev, I. et al. 2002 "The *E. coli* α-hemolysin secretion system and its use in vaccine development." *Trends Microbiol.* 10:39-45.

(Continued)

*Primary Examiner*—Scott Long
(74) *Attorney, Agent, or Firm*—Swanson & Bratschun, L.L.C.

(57) ABSTRACT

The invention is related to intracellularly induced bacterial DNA promoters and vaccines against *Bacillus anthracis.*

21 Claims, 38 Drawing Sheets

OTHER PUBLICATIONS

Germanier, R. et al. 1975 "Isolation and characterization of Gal E mutant Ty 21a of *Salmonella typhi*: a candidate strain for a live, oral typhoid vaccine." *J. Infect. Dis.* 131:553-558.

Hohmann, E.L. et al. 1996 "*phoP/phoQ*-deleted *Salmonella typhi* (Ty800) is a safe and immunogenic single-dose typhoid fever vaccine in volunteers." *J. Infect. Dis.* 173:1408-1414.

Hollingsworth, J. et al. 1997 "Federal agencies collaborate to control dangerous new *Salmonella* strain." *J. Am. Vet. Med. Assoc.* 210: 1712 & 1716.

Hone, D. et al. 1988 "A chromosomal integration system for stabilization of heterologous genes in *Salmonella* based vaccine strains." *Microb. Pathog.* 5:407-418.

Hosek, G. et al. 1997 "Multidrug-resistant *Salmonella* serotype typhimurium—United States, 1996" *MNWR* 46:308-310.

Ito, K. et al. 1980 "Synthesis, assembly into the cytoplasmic membrane, and proteolytic processing of the precursor of coliphage M13 coat protein." *J. Biol. Chem.* 255:2123-2130.

Ivins, B.E. et al. 1986 "Cloning and expression of the *Bacillus anthracis* protective antigen gene in *Bacillus subtilis*." *Infect. Immun.* 54:537-542.

Ivins, B.E. et al. 1998 "Comparative efficacy of experimental anthrax vaccine candidates against inhalation anthrax in rhesus macaques." *Vaccine* 16:1141-1148.

Larkin, M. 2002 "Anthrax vaccine is safe and effective-but needs improvement, says IOM." *Lancet* 359:951.

Levine, M.M. et al. 1999 "Duration of efficacy of Ty21a, attenuated *Salmonella typhi* live oral vaccine." *Vaccine* 17:S22-S27.

Maskell, D.J. et al. 1987 "The initial suppression of bacterial growth in a *Salmonella* infection is mediated by a localized rather than a systemic response." *Microb. Path.* 2:295-305.

Mock, M. et al. 2001 "Anthrax." *Annu. Rev. Microbiol.* 55:647-671.

Nakayama, K. et al. 1988 "Construction of an $ASD^+$ expression-cloning vector: stable maintenance and high level expression of cloned genes in a *Salmonella* vaccine strain" *Biotechnology* 6:693-697.

Oxer, M.D. et al. 1991 "High level heterologous expression in *E. coli* using the anaerobically-activated *nirB* promoter." *Nucleic Acids Res.* 19:2889-2892.

Pasetti, M.F. et al. 2003 "Attenuated *Salmonella* enterica serovar Typhi and *Shigella flexneri* 2a strains mucosally deliver DNA vaccines encoding measles virus hemagglutinin, inducing specific immune responses and protection in cotton rats." *J. Virol.* 77: 5209-5217.

Rhie, G. et al. 2003 "A dually active anthrax vaccine that confers protection against both bacilli and toxins." *PNAS USA* 100:10925-10930.

Schneerson, R. et al. 2003 "Poly(γ-D-glutamic acid) protein conjugates induce IgG antibodies in mice to the capsule of *Bacillus anthracis*: a potential addition to the anthrax vaccine. "*PNAS USA* 100:8945-8950.

Schodel, F. 1992 "Prospects for oral vaccination using recombinant bacteria expressing viral epitopes." *Adv. Virus Res.* 41:409-446.

Singh, Y. et al. 1989 "A deleted variant of *Bacillus anthracis* protective antigen is non-toxic and blocks anthrax toxin action in vivo." *J. Biol. Chem.* 264:19103-19107.

Strugnell, R.A. et al. 1990 "Stable expression of foreign antigens from the chromosome of *Salmonella typhimurium* vaccine strains." *Gene* 88:57-63.
Tite, J.P. et al. 1990 "Anti-viral immunity induced by recombinant nucleoprotein of Influenza A virus. III Delivery of recombinant nucleoprotein to the immune system using attenuated *Salmonella typhimurium* as a live carrier." *Immunology* 70:540-546.
Wahdan, M.H. et al. 1980 "A controlled field trial of live oral typhoid vaccine Ty21a." *Bull. WHO* 58:469-474.
Wall P.G. et al. 1995 "Transmission of multi-resistant strains of *Salmonella typhimurium* from cattle to man." *Vet. Rec.* 136:591-592.
Wang, J.Y. 2001 "Construction, genotypic and phenotypic characterization, and immunogenicity of attenuated Δ*guaBA Salmonella enterica* serovar Typhi strain CVD 915." *Infect. Immun.* 69:4734-4741.
Welkos, S.L. et al. 1988 "Comparative safety and efficacy against *Bacillus anthracis* of protective antigen and live vaccines in mice." *Microb. Pathog.* 5:127-139.
Xu, D. et al. 2002 "Molecular cloning and characterization of genes for *Shigella sonnei* form I O polysaccharide: proposed biosynthetic pathway and stable expression in a live *Salmonella* vaccine vector." *Infect. Immun.*70:4414-4423.
Zegers, N. D. et al. 1999 "Expression of the protective antigen of *Bacillus anthracis* by *Lactobacillus casei*: towards the development of an oral vaccine against anthrax." *J. Appl. Microbiol.* 87:309-314.
Bhattacharyya, S.P. et al. 2003 "Construction of a live, attenuated *Salmonella typhi* TY21A vector expressing anthrax protective antigen." ASM Conference on *Salmonella*, poster presentation 154(A), Sep. 23, 2003, Alghero, Sardinia, Italy.
Chatfield, S.N. et al. 1992 "Use of the nirB promoter to direct the stable expression of heterologous antigens in *Salmonella* oral vaccine strains: development of a single-dose oral tetanus vaccine." *Biotechnology* 10: 888-892.
Coulson N.M. et al. 1994 "*Bacillus anthracis* protective antigen, expressed in *Salmonella typhimurium* SL 3261, affords protection against anthrax spore challenge." *Vaccine* 12: 1395-1401.
Curtiss, R., III. 2002 "Bacterial infectious disease control by vaccine development." *J. Clin. Invest.* 110: 1061-1066.
Database EMBL Accession No. A00198, Jan. 28, 1993.
Database EMBL Accession No. AE008791, Oct. 29, 2001.
Database EMBL Accession No. AE008807, Oct. 29, 2001.
Database EMBL Accession No. AE008808, Oct. 29, 2001.
Database EMBL Accession No. AE008836, Oct. 29, 2001.
Database EMBL Accession No. AF044668, Jul. 2, 1998.
Database EMBL Accession No. AF095415, Mar. 11, 1999.
Database EMBL Accession No. AF306778, Oct. 20, 2000.
Database Geneseq Accession No. ACA49473, Jun. 19, 2003.
Database Geneseq Accession No. ACA50818, Jun. 19, 2003.
Database Geneseq Accession No. ACA51177, Jun. 19, 2003.
Database Geneseq Accession No. ACA51493, Jun. 19, 2003.
Database Geneseq Accession No. ACH96763, Jul. 29, 2004.
European Patent Office Communication dated Apr. 10, 2007, pursuant to European Patent No. 0480769.5.
Formal, S.B. et al. 1981 "Construction of a potential bivalent vaccine strain: introduction of *Shigella sonnei* Form I antigen genes into the galE *Salmonella typhi* TY21a typhoid vaccine strain." *Infec. Immun.* 34: 746-750.
Giri, C.P. et al. 2003 "Development of a Promotertrap, bacterial expression system to identify *Salmonella typhimurium* DT104 genes that are induced specifically during invasion into INT407 cells." ASM Conference on *Salmonella*, poster presentation 153(C), Sep. 23, 2003, Alghero, Sardinia, Italy.
Gupta, P. et al. 1999 "Expression and Purification of the Recombinant Protective Antigen of *Bacillus anthracis." Protein Express. Purif.* 16: 369-376.
Lu, Z. et al. 1989 "The Nucleotide Sequence of *Escherichia coli* Genes for L-fucose Dissimilation." *Nucleic Acids Res.* 17: 4883-4884.
McCelland, M. et al. 2001 "Complete genome sequence of *Salmonella enterica* serovar Typhimurium LT2." *Nature* 413: 852-856.
Phillips, G.J. et al. 1987 "Determination of the Nucleotide Sequence for the Exonuclease I Structural Gene sbcB of *Escherichia coli* K12." *J. Biol. Chem.* 262: 455-459.
Price, L.B. et al. 1999 "Genetic diversity in the protective antigen gene of *Bacillus anthracis." J. Bacteriol.* 181: 2358-2362.
Sulavik, M.C. et al. 1997 "The *Salmonella typhimurium* mar locus: molecular and genetic analyses and assessment of its role in virulence." *J. Bacteriol.* 179: 1857-1866.
Turnbull, P.C.B. 1991 "Anthrax Vaccines: Past, Present and Future." *Vaccine* 9: 533-539.
Valdivia, R.H. et al. 1996 "Bacterial Genetics by Flow Cytometry: Rapid Isolation of *Salmonella typhimurium* Acid-Inducible Promoters by Differential Fluorescence Induction." *Mol. Microblol.* 22: 367-378.

Yu, G-Q et al. 1986 "Identification and Nucleotide Sequence of the Activator Gene of the Externally Induced Phosphoglycertate Transport System of *Salmonella typhimurium.*" *Gene* 45: 51-58.

Galen et al. "Adaptation of the Endogenous *Salmonella enterica* Serovar Typhi *clayA*-Encoded Hemolysin for Antigen Export Enhances the Immunogenicity of Anthrax Protective Antigen Domain 4 Expressed by the Attenuated Live-Vector Vaccine Strain CVD 908-*htrA*." Infection and Immunity. 72(12):7096-7106 (2004).

Osorio, Manuel et al, "Anthrax Protective Antigen Delivered by *Salmonella enterica* Serovar Typhi Ty21a Protects Mice from a Lethal Anthrax Spore Challenge," Infection and Immunity, 2009, vol. 77, pp. 1475-1482.

\* cited by examiner

*Infection of INT407 cells with S. typhimurium DT104 genomic library in pCG101*

1. Infection for 1-3 hrs.
2. Gentamicin added at 100 ug/ml, 1hr. to kill extracellular bacteria
3. Chloramphenicol added at 100 ug/ml for 16 hrs. to kill uninduced CAT bacteria
4. FACS-selection of GFP⁺ induced bacteria
5. Growth in nutrient medium oveernight and FACS-selection of only GFP bacteria

*S. typhimurium pCG101-promoter fragment clones that upregulate reporter genes intracellularly*

Repeat 3 times the above double-selection (i.e. for intracellular expression of CAT and GFP)

Highly enriched library of promoter fragments that are activated intracellularly

*FIG. 3*

*Infection of J774.A3 cells with S. typhimurium DT104 genomic library in pCG101*

⬇

1. Infection for 1-2 hrs.
2. Gentamicin added at 100 ug/ml, 1hr. to kill extracellular bacteria
3. Host cells were lyzed with 0.5% Triton X-100 10 min., 37°C to release bacteria.
4. FACS-selection of GFP$^+$ induced bacteria
5. Growth in nutrient medium oveernight and FACS-selection of only GFP bacteria

*S. typhimurium pCG101-promoter fragment clones that upregulate reporter genes intracellularly*

⬇ *Repeat 4 times the above double-selection (i.e. for intracellular expression of GFP)*

Highly enriched library of promoter fragments that are activated intracellularly

1. >Promoter Fragment Insert in pCG301 (689 bp) (SEQ ID NO: 1)

```
TGGGCACAACTCCCAGTGAAAAGTTCTTCCTCCTTTACGCATGCCTTAATTTCTCCTCTTT
AATTCTAGGTACCCGGGGATCATTTTAGTATTTTGTACTCACCATCGCATGTACGAACATT
AGCAACAATATCAATTGGTGTACAAATACAATCAATCAACGACAAAATAAAAGAATAAAAT
ATTTCATATACATATAACATCAGGCGTGTACATCAAGTGACAGTTAAAAACGACAGCATAC
AGAGCACATTCCTCTTCCACGATTACGAAACCTTCGGTACGCATCCAGCCCTCGACAGACC
TGCGCAATTCGCCGCGCTCCGTACGGATAACGACTTCAACGTTATTGGCGAGCCGGAGGTG
TTTTATTGCAAACCCGCCGATGATTATCTACCGCAGCCCGGCGCGGTGCTGATTACCGGCA
TCACGCCGCAGGAAGCGCGTGAGAAAGGAGAAAACGAAGCCGCTTTCGCCAGACGCATTCA
TGCGCTGTTCACCGTTCCTAAAACCTGCGTTGTGGGCTACAACAATGTGCGCTTTGATGAT
GAAGTCACGCGCAATATTTTTTATCGCAACTTTTACGATCCTCTAGAGTCGACCTGCAGCG
CTTCCTCGCTCACTGACTCGCTGCGCTCGGTCGTTCGGCTGCGGCGAGCGGTTACAGCTCA
CTTCAAAGGCGGTAATAC
```

*2. >Promoter Fragment Insert in pCG316 (971 bp) (SEQ ID NO: 2)*

CCGTATCCGCCTTGATAGCTTGTAACCGTCCGCCGTCACCGAACGACCGCAGCGCAGCGAG
TCAGTGAGTCGAGGAAGCGCTGCAGGTCGACTCTAGAGGATCAAGCGCACCCAGCGGAATG
ATTTCATTGAACAGATCACTGGTGCTTTTCAAAATGGTTGCCCCGGCAAGTAATTAATTTC
GTCAGATACTATTGCCCAGGCAAGTATAAGTCAACTAAATGAATTGGCCGATGCCACGATT
TGCTAAAAGGCGTCCGGGGTATTGTGCTGTGATAACTTGTAACTAATTGATAATTACAGGT
TATAGGTTGTAGAGGATATTAACTTGCACACTGGCGAAATGGCGCGCCTGGGCAATTTCAC
TTTATACTTCCGGTTCATGAAACGCTGATGGGTAAGAGATAGTATTATGATGGATTTGTTT
AAAGCGATTGGATTGGGGCTGGTCGTACTGCTCCCGTTAGCCAATCCGCTAACCACCGTGG
CGCTGTTTCTTGGCCTTGCGGGCAATATGAATAGTGCGGAACGCAACCGGCAGTCCTATAT
GGCTTCGGTTTATGTCTTCGCTATTATGATGGTGGCGTACTACGCCGGGCAGTTAGTCATG
AACACCTTCGGTATTTCGATTCCAGGGCTACGGATCGCCGGGGGGTTAATCGTGGCGTTTA
TCGGCTTCAGAATGCTTTTCCCGCAGCAGAAGGCGCATGAGTCGCCGGAAGCGAAAAGCAA
ATCGGAGGAGCTGGCAGACGAACCGACGGCCAATATTGCGTTTGTTCCACTGGCTATGCCA
AGCACCGCAGGACCGGGGACCATCGCAATGATCATCAGTTCCGCTTCCACGGTGCGTCATG
GCGGCGAGTTTCCCGACTGGGTCATTATGGTCGCGCCGCCGATTATTTTTCTTGCCGTGGC
GGTGATCCCCGGGTACCTGAATTAAGAGAGGAAAATTGACTGCGTAGAAGAGAAAC

*3. >Promoter Fragment Insert in pCG322 (1468 bp)(SEQ ID NO: 3)*

TGATACCGCTCGCCGCAGCCGAACGACCGAGCGCAGCGAGTCAGTGAGCGAGGAAGCGCTG
CAGGTCCGACTTCAGAGGATTCGATGACGCTTGTTTCATGCAGGATGACGATCAACTGCCA
TTTTATTGTTACCGGACTGGCGATGTACCGATGGCGGTTGTAGCGGAGAAAAAGGGCGCCT
GGGATTTTCTGCAAAAACCCGTCGATCCGGGCAAGCTTTTTGATATTAATTGAAGACGCGC
TACGCCAGCGCCGGTTCGGTATTGCACGGCGGCAATATTGCCAGCAGACGTTACAGGTTTG
AACTGATTGGGCGCAGCGAGTGGATGAATCAGTTTCGACAACGGTTACAACAACTGGCGGA
AACGGACATTGCCGTATGGTTTTACGGTTGAGCATGGCACTCGGACGTATGACTCGGCGCC
CGTTATCTCCTCAACTGGGGCGTAACGCGAAAGGGCCGTTTGTACGCTATGAACTTACGCC
GGAGAATGCCGGGCAGTTGGAGACATTCATCGACCAGGCGCAAGGAGGCACGCTGGTGTTG
AGTCATCCCGAATATCTGACACGCGAACAGCAGCACCATCTGGCGCGTTTACAAAGCCTGG
AGCATCGGCCTTTTCGTTTGGTGGGCGTTGGCAGCGCTTCGCTGGTGGAGCAGGCGGCAGC
TAACCAGATTGCAGCCGAGCTTTACTACTGTTTCGCCATGACCCAAATCGCCTGCCAGTCT
CTTTCTCAGCGACCGGATGATATCGAGCCGTTATTTCGCCATTATCTTCGAAAAGCCTGCC
TGCGACTCAATCATCCAGTGCCGGAAATAGCGGGGGAATTACTGAAAGGAATAATGCGACG
CGCCTGGCCTAGCAATGTGCGCGAACTGGCTAATGCGGCAGAGCTTTTGCTGTTGGCGTG
CTGCCGCTGGCGGAAACGGTCAACCCGCAGTTGCTTCTTCAGGAGCCGACCCCGCTTGACC
GGCGCGTTGAAGAGTATGAGCGACAAATCATTACCGAAGCATTAAATATTCATCAGGGACG
AATTAATGAAGTGGCGGAGTACCTGCAAATTCCCCGTAAAAAACTTTATCTGCGCATGAAA
AAAATAGGTCTAAGTAAAAAGCATTATAAATTCTGATATTACAGTTACTTTCAATCTGGCT
GACAACATCAGCAACGATGTCGTTAGCCAGATAACGTCGCATCACCGTAAGGTAAATCATT
CCATCATGATTATAGATTGCTTATTATTCACCTGGGCATCAAATTCTATTTCTTAACTTCA
ATATAGGTAAAAGCGTCAAGTTCTCTGGCGTAATAAATGTACTCTTGTCCGACGATTTGA
CAAGATGAAAACTTCATCCCCTCTCCAGATTACATCTGAATATGAGGACAAGAGAAATGAA
AAAACATGCTATTGCAGTAATGATGATCCCCGGGTACCTAGAATTAAGAGGAGAAATGAAA
AATT

*FIG. 8B*

*4. >Promoter Fragment Insert in pCG433 (837 bp)(SEQ ID NO: 4)*

TGGGACAACTCCAGTGAAAAGTTCTTCTCCTTTACGCATGCTTAATTTCTCCTCTTTAATT
CTAGGTACCCGGGGATCGTCATTCAAAATTCGAAGCGACAACATTTGCAGGCGCGCTAAAA
CGTTCTCCATACGCCGCCTCAAGCACAGGAATAATTTTAGTGCCCGTGTCGATTCCTACCT
CATCCAAAAGTTGGATTGGCCCCACCGGAAAACCAAATTTTACCAGGGCGGCGTCAATATG
TTCGACGCGTTCGCCTTCAGTCAGCATCCGAATCGCCTCATTGATATATGGCGCAAGAATT
CGGTTAACATAAAACCCGGCTTTATCACTGACGACTATCGGGGTTTTACCCTGTTTTTTCG
CCAGCTTAACGGTCGTGGCGATGGTCTGCGCGGAAGTAGACGCATGAGGAATAACCTCAAC
CAGCGGCATTTTTTCGACCGGGCTAAAAAAGTGCAATCCAATCACCTGTTCCGGTCTGGCC
GCATTCGCCGCAATATCGCCAATCGGCAGGGAAGAAGTATTGGAGGCAAAAATGGTGTGAG
CAGCGCAATTTTGCTCCACTTCCGCCACCATCTGTTGTTTTAACGGCAGATCTTCAAACAC
CGCTTCAATGACCAGATCACGATGACTGAAACCACGGTAATCGGTCGAACCTGATATCAAC
GCCAACTGTTTATCGCGTTCGCTGGCTTTGATATGGCGGCGGCGTACTTTTGTTTCAAGCA
GATCCTCTAGAGTCGACCTGCAGCGCTTCCTCGCTCACTGACTCGCTGCGCTCGGTCGTTC
GGCTGCGGCGAGCGGTTACAGCTCACTCAAAGGCGGTAATACGG

*5. >Promoter Fragment Insert in pCG307 (577 bp)(SEQ ID NO: 5)*

TGGGACAACTCCCAGTGAAAAGTTCTTCTCCTTTACGCATGCTTAATTTCTCCTCTTTAAT
TCTAGGTACCCGGGGATCATATCCCAGAGCCGCAGAAGCTTCAGCAAACGTTTCTTCTACG
ATAGGGTAATTTGCCGCCATCTCGGCCAACATCCCAACGCTCTGAGAACCCTGACCGGGGA
ACACAAATGCAAATTGCGTCATGTTTAAATCCTTATACTAGAAACGAATCAGCGCGGAGCC
CCAGGTGAATCCACCCCCGAAGGCTTCAAGCAATACCAGCTGACCGGCTTTAATTCGCCCG
TCACGCACGGCTTCATCCAGCGCGCACGGCACAGAAGCCGCGGAGGTATTGCCGTGCCTGT
CCAGCGTGACGACGACATTGTCCATCGACATGCCGAGTTTTTTCGCTGTCGCGCTAATGAT
ACGCAGGTTAGCCTGATGCGGCACCAGCCAATCGAGTTCTGAGCGATCCTCTAGAGTCGAC
CTGCAGCGCTTCCTCGCTCACTGACTCGCTGCGCTCGGTCGTTCGGCTTGCGGCGAGCGGA
ATCAGCTCACTCAAAGGCGGTAATACGA

*6. >Promoter Fragment Insert in pCG502 (689 bp)(SEQ ID NO: 6)*

GCAGCCGAACGACCGAGCGCAGCGAGTCAGTGAGCGAGGAAGCGCTGCAGGTCGACTCTAG
AGGAGCTGGTGCTGACCTGTACCGACAACCAGTCGCGCAACCGTCGTTTTGGCATGATGCT
TGGCCAGGGCATGGACGTTAAAGGCGCGCAGGATAAGATTGGCCAGGTGGTCGAAGGCTAT
CGCAATACGAAAGAAGTTCGTGAATTGGCGCACCGTTTTGGTGTTGAAATGCCAATAACCG
AGGAAATTTATCAAGTATTGTATTGCGGAAAAAACGCGCGCGAGGCAGCATTAACGTTATT
AGGTCGCGCCCGCAAGGAAGAGCTGAGTCGCCACTAGCCGTAAGGAACTGTTTGCTATAAC
GACCCAACCCGCACAGAACGGGTTGGTCGTTTTCTGCCCGTCTGGAGTAAGCCATGCCGTG
TGAAGAACTGGAAATCGTCTGGAAGAATATTAAAGCTGAAGCCCGCGCTTTAGCTGACTGT
GAGCCTATGTTGGCCAGTTTTTATCACGCCACGCTACTCAAGCATGAAAATCTGGGCAGTG
CGCTGAGCTATATGCTGGCAAATAAACTGGCTTCGCCCATCATGCCCGCTATCGCTATCCG
TGAAGTAGTTGAAGAAGCCTATGCCGCCGTACCCGGAAATGATCCCCGGGTACCTAGAATT
AAAGAGGAGAAATTAAGC

*FIG. 8C*

*7. >Promoter Fragment Insert in pCG501 (979 bp – Forward) (SEQ ID NO: 7)*

TCGTAACCCGTCCGCCGCAGTCCGAACGACACGAGCCGCAGCGAGTCAGTGAGTCGAGGAA
GCGCTGCAGGTCGACTTCAGAGGATCGCTGACGCTAAGACCATCGGCGCGAATCACCTGCG
GGCCCAGGCTATGCGCGGGAAAGTGAGCGTCGGAAAAAATGATTTCGTCCCCGTGGCCCAT
CTCGGCCAGCACTTTGAGCAGTGTCGGGGAAATTAACGGTGAAATGGTTTTTAGCTTTCAT
ACTCCCTCAATAATTTCAGGTTCGGTTTGCGGCCAGAAATAACGATACTGATAATTGACCT
GCGCGCGCGCCTGTTCCGGGCTACTAAATTCGCCTACGCCGTACCAGCCAAACATGGCAGC
GCCGGCCACGGTGGTTTTCGCGTCGTCCAGCACTTTGATAGGGATATCAAGCTGATTCGCT
TTAATTTGATTCCTAAAGCGTTAGCGACTGCCGCCGCCAACCAGTAACAGTTCTGTGGCGT
TAAAATGGCCGATTTTCTCCAGCGTGCGCAGATTACGCTGAAGTTGCGCCGTCAGGCCTTC
CAGCGCGGCGCGATAGAAATGGCCGCGGGTGGTATTGAGCGTCACGCCCTGCCAGCCTGCA
TTTTGGCAGGCGAGCAGATCGCACTGCATCCGACGCCTTCCGCGCCAGCGGGAATAGCGCG
CGCTTCGTCGATCAGCGTTTGCCATGGCGTTCCGGCGTCCACAGCAGTTTCGTACCCATTC
GAGTACACCGGAGGCCAGCCACTGCATTCCGGGGTTATAAAGCCCCGACTGACTGTTCAGT
TACAGGTCAGCCCGATACTGACTGAGCAGCGAGGTATCCACTTGACCGCTGCGCACCATCA
GATCTCCATGTTCCGGAGGAGAGCACCGTTACCCTGCTGCGCGCCAGCGCCGATAACGCGA
ACTCGAGTATCCGTCGCCAGAAATACCATTAAGGCATCCGGAATTAATATATTGCCGCCAG
GCC

*8. >Promoter Fragment Insert in pCG501 (864 bp – Reverse) (SEQ ID NO: 8)*

ACAATTTCCTCATCTTAATTTCAGGTACCCGGGGATCCGGGTACTATAGAGCCCAATCCAA
CACGGGGAAGTGTTCGTTACTGAAGACGGCGCTGAAACCGACCTGGACCTGGGGCACTACG
AGCGTTTCATCCGCACCAAGATGTCTCGCCGCAACAACTTTCACGACTGGCCGCATCTACT
CCGACGTTCTGCGTAAAGAACGCCGTGGCGACTATCTGGGCGCAACCGTACAGGTCATCCC
TCACATCACTAACGCGATTAAAGAGCGCGTGCTGGAAGGTGGCGAAGGCCACGATGTGGTA
CTGGTGGAAATCGGCGGTACCGTCGGTGATATCGAATCGCTGCCGTTTCTTGAGGCGATTC
GTCAATTGGCGGTAGATATTCGGTCGTGAACACGCGCTGTTTATGCACCTGACGCTGGTAC
CTTACCTGGCGGCTGCGGGCGAAGTGAAAACTAAACCGACTCAGCACTCCGTGAAAGAGCT
GCTGTCTATCGGTATTCAGCCCGATATTCTGATTTGTCGTTCCGATCGCGCGGTTCCTGCC
AACGAGCGTGCAAAAATTGCATTGTTCTGTAATGTGCCGGAAAAAGCCGTTATTTCAATGA
AAGATGTCGATTCCATTTATAAAATTCCGGGCCTGTTGAAATCTCAGGGGCTTGATGATTA
TATTTGTAAACGATTCAGCTTGAACTGTCCGGAAGCTAACCTGTCTGAATGGGAACAGGTC
ATTTACGAAGAAGCGAACCCGGCAGGCGAAGTGACTATCGGCATGGTCGGCAAATATATTT
GAACTGCCGGATGCCTATAAGTCGGTGATCTCTGCCGGACACGATACTCAGTTCGCGTTAT
TCGCGCTGGC

*FIG. 8D*

Anthrax Protective Antigen (PA) gene was amplified from cloned wild-type PA gene by PA-BglII-Start: 5'- GGAAGATCTTAATCATCCACAGGAGACTTTCTGATGGAAGTTAAAACAGGAA-3'
and PA-BamHI-Stop: 5'- CGGGATCCCGGTTAAAACATACTCTCC-3'

PCR product digested with BglII/BamHI

Ligated and transformed into *E.coli* and *Salmonella* Typhi Ty21a pGB2/P$_{nirB}$/PA EcoRI
Rep
Spc$^R$/Sm$^R$ P$_{nirB}$
PA

DNA Sequences Coding for *B. anthracis* Protective Antigen

*Native codon PA sequence (SEQ ID NO: 9):* atggaagttaaacaggagaaccggttattaaatgaatcagaatcaagttcccaggggttactaggatactattttagtgatttgaattttc
aagcacccatggtggttacctcttctactacaggggatttatctattcctagttctgagttagaaaatattccatcggaaaaccaatatttt
caatctgctatttggtcaggatttatcaaagttaagaagagtgatgaatatacatttgctacttccgctgataatcatgtaacaatgtgggt
agatgaccaagaagtgattaataaagcttctaattctaacaaaatcagattagaaaaaggaagattatatcaaataaaaattcaatatca
acgagaaaatcctactgaaaaaggattggatttcaagttgtactggaccgattctcaaaataaaaaagaagtgatttctagtgataactt
acaattgccagaattaaaacaaaaatcttcgaactcaagaaaaaagcgaagtacaagtgctggacctacggttccagaccgtgaca
atgatggaatccctgattcattagaggtagaaggatatacggttgatgtcaaaaataaaagaactttttctttcaccatggatttctaatatt
catgaaaagaaaggattaaccaaatataaatcatctcctgaaaaatggagcacggcttctgatccgtacagtgatttcgaaaaggtta
caggacggattgataagaatgtatcaccagaggcaagacacccccttgtggcagcttatccgattgtacatgtagatatggagaata
ttattctctcaaaaaatgaggatcaatccacacagaatactgatagtcaaacgagaacaataagtaaaaatacttctacaagtaggac
acatactagtgaagtacatggaaatgcagaagtgcatgcgtcgttctttgatattggtgggagtgtatctgcaggatttagtaattcgaa
ttcaagtacggtcgcaattgatcattcactatctctagcaggggaaagaacttgggctgaaacaatgggtttaaataccgctgataca
gcaagattaaatgccaatattagatatgtaaatactgggacggctccaatctacaacgtgttaccaacgacttcgttagtgttaggaaa
aaatcaaacactcgcgacaattaaagctaaggaaaaccaattaagtcaaatacttgcacctaataattattatccttctaaaaaacttggc
gccaatcgcattaaatgcacaagacgatttcagttctactccaattacaatgaattacaatcaatttcttgagttagaaaaaacgaaaca
attaagattagatacggatcaagtatatgggaatatagcaacatacaattttgaaaatggaagagtgagggtggatacaggctcgaa
ctggagtgaagtgttaccgcaaattcaagaaacaactgcacgtatcatttttaatggaaaagatttaaatctggtagaaaaggcggata
gcggcggttaatcctagtgatccattagaaacgactaaaccggatatgacattaaaagaagcccttaaaatagcatttggatttaacg
aaccgaatggaaacttacaatatcaagggaaagacataaccgaatttgattttaatttcgatcaacaaacatctcaaaatatcaagaat
cagttagcgaattaaacgcaactaacatatatactgtattagataaaatcaaattaaatgcaaaaatgaatatttaataagagataaa
cgtttcattatgatagaaataacatagcagttggggcggatgagtcagtagttaaggaggctcatagagaagtaattaattcgtcaac
agagggattattgttaaatattgataaggatataagaaaaatattatcaggttatattgtagaaattgaagatactgaagggcttaaaga
agttataaatgacagatatgatatgttgaatatttctagtttacggcaagatggaaaaacatttatagattttaaaaaatataatgataaatt
accgttatatataagtaatcccaattataaggtaaatgtatatgctgttactaaagaaaacactattattaatcctagtgagaatggggat
actagtaccaacgggatcaagaaaattttaatcttttctaaaaaaggctatgagataggataa

DNA Sequences Coding for *B. anthracis* Protective Antigen

*Codon-modified PA sequence (SEQ ID NO: 10):* gaagttaaacaggagaaccgtctgctgaatgaatcagaatcaagttcccagggtctgctgggctactattttagtgatctgaattttca
agcaccgatggtggttacttcttctactacaggtgatctgtctattccgagttctgagctggaaaatattccgtcggaaaaccaatatttt
caatctgctatttggtcaggctttatcaaagttaagaagagtgatgaatatacatttgctacttccgctgataatcatgtaacaatgtgggt
agatgaccaagaagtgattaataaagcttctaattctaacaaaatccgcctggaaaaaggccgcctgtatcaaatcaaaattcaatatc
aacgtgaaaatccgactgaaaaaggcctggatttcaagctgtactggaccgattctcaaaataaaaaagaagtgatttctagtgataa
cctgcaactgccggaactgaaacaaaaatcttcgaactcaagcaacaaggagagtacaagtgctggtccgacggttccggaccgt
gacaatgatggtatcccggattcactggaggtagaaggttatacggttgatgtcaaaaataaacgtacttttctgtcaccgtggatttct
aatattcatgaaaagaaaggcctgaccaaatataaatcatctccggaaaaatggagcacggcttctgatccgtacagtgatttcgaaa
aggttacaggccgtattgataagaatgtatcaccggaggcacgccaccgctggtggcagcttatccgattgtacatgtagatatgg
agaatattattctgtcaaaaaatgaggatcaatccacacagaatactgatagtgaaacgcgcacaatcagtaaaaatacttctacaagt
cgtacacatactagtgaagtacatggtaatgcagacgtgcatgcgtcggatattggtggcagtgtatctgcaggttttagtaattcgaa
ttcaagtacggtcgcaattgatcattcactgtctctggcaggcgaacgtacttgggctgaaacaatgggtctgaataccgctgataca
gcacgcctgaatgccaatattcgttatgtaaatactggcacggctccgatctacaacgtgctgccgacgacttcgctggtgctgggta
aaaatcaaacactggcgacaattaaagctaaggaaaaccaactgagtcaaatcctggcaccgaataattattatccgtctaaaaacct
ggcgccgatcgcactgaatgcacaagacgatttcagttctactccgattacaatgaattacaatcaatttctggagctggaaaaaacg
aaacaactgcgtctggatacggatcaagtatatggcaatatcgcaacatacaattttgaaaatggtcgcgtgcgtgtggatacaggct
cgaactggagtgaagtgctgccgcaaattcaagaaacaactgcacgtatcatttttaatggtaaagatctgaatctggtagaacgtcg
cattgcggcggttaatccgagtgatccgctggaaacgactaaaccggatatgacactgaaagaagccctgaaaatcgcatttggttt
taacgaaccgaatggcaacctgcaatatcaaggcaaagacattaccgaatttgattttaatttcgatcaacaaacatctcaaaatatca
agaatcagctggcggaactgaacgcaactaacatctatactgtactggataaaatcaaactgaatgcaaaaatgaatattctgattcg
cgataaacgttttcattatgatcgtaataacattgcagttggcgcgcggatgagtcagtagttaaggaggctcatcgcgaagtaattaattc
gtcaacagagggcctgctgctgaatattgataaggatatccgcaaaatcctgtcaggttatattgtagaaattgaagatactgaaggc
ctgaaagaagttattaatgaccgctatgatatgctgaatatttctagtctgcgccaagatggtaaaacatttatcgattttaaaaaatataa
tgataaactgccgctgtatatcagtaatccgaattataaggtaaatgtatatgctgttactaaagaaaacactattattaatccgagtgag
aatggcgatactagtaccaacggcatcaagaaaattctgatcttttctaaaaaaaggctatgagattggctaa

*FIG. 23B*

SEQUENCE LISTING

<160> NUMBER OF SEQ ID NOS: 36

<210> SEQ ID NO 1
<211> LENGTH: 689
<212> TYPE: DNA
<213> ORGANISM: Salmonella Typhimurium

<400> SEQUENCE: 1
tgggcacaac tcccagtgaa aagttcttcc tcctttacgc atgccttaat ttctcctctt 60
taattctagg tacccgggga tcattttagt attttgtact caccatcgca tgtacgaaca 120
ttagcaacaa tatcaattgg tgtacaaata caatcaatca acgacaaaat aaaagaataa 180
aatatttcat atacatataa catcaggcgt gtacatcaag tgacagttaa aaacgacagc 240
atacagagca cattcctctt ccacgattac gaaaccttcg gtacgcatcc agccctcgac 300
agacctgcgc aattcgccgc gctccgtacg gataacgact tcaacgttat tggcgagccg 360
gaggtgtttt attgcaaacc cgccgatgat tatctaccgc agcccggcgc ggtgctgatt 420
accggcatca cgccgcagga agcgcgtgag aaaggagaaa acgaagccgc tttcgccaga 480
cgcattcatg cgctgttcac cgttcctaaa acctgcgttg tgggctacaa caatgtgcgc 540
tttgatgatg aagtcacgcg caatattttt tatcgcaact tttacgatcc tctagagtcg 600
acctgcagcg cttcctcgct cactgactcg ctgcgctcgg tcgttcggct gcggcgagcg 660
gttacagctc acttcaaagg cggtaatac 689

<210> SEQ ID NO 2
<211> LENGTH: 971
<212> TYPE: DNA
<213> ORGANISM: Salmonella Typhimurium

<400> SEQUENCE: 2

```
ccgtatccgc cttgatagct tgtaaccgtc cgccgtcacc gaacgaccgc agcgcagcga      60
gtcagtgagt cgaggaagcg ctgcaggtcg actctagagg atcaagcgca cccagcggaa     120
tgatttcatt gaacagatca ctggtgcttt tcaaaatggt tgccccggca agtaattaat     180
ttcgtcagat actattgccc aggcaagtat aagtcaacta aatgaattgg ccgatgccac     240
gatttgctaa aaggcgtccg gggtattgtg ctgtgataac ttgtaactaa ttgataatta     300
caggttatag gttgtagagg atattaactt gcacactggc gaaatggcgc gcctgggcaa     360
tttcacttta tacttccggt tcatgaaacg ctgatgggta agagatagta ttatgatgga     420
tttgtttaaa gcgattggat tggggctggt cgtactgctc ccgttagcca atccgctaac     480
caccgtggcg ctgtttcttg gccttgcggg caatatgaat agtgcggaac gcaaccggca     540
gtcctatatg gcttcggttt atgtcttcgc tattatgatg gtggcgtact acgccgggca     600
gttagtcatg aacaccttcg gtatttcgat tccagggcta cggatcgccg ggggggttaat     660 cgtggcgttt atcggcttca gaatgctttt cccgcagcag aaggcgcatg agtcgccgga     720
agcgaaaagc aaatcggagg agctggcaga cgaaccgacg gccaatattg cgtttgttcc     780
actggctatg ccaagcaccg caggaccggg gaccatcgca atgatcatca gttccgcttc     840
cacggtgcgt catggcggcg agtttcccga ctgggtcatt atggtcgcgc cgccgattat     900
ttttcttgcc gtggcggtga tccccgggta cctgaattaa gagaggaaaa ttgactgcgt     960
agaagagaaa c                                                          971

<210> SEQ ID NO 3
<211> LENGTH: 1468
<212> TYPE: DNA
<213> ORGANISM: Salmonella Typhimurium

<400> SEQUENCE: 3
tgataccgct cgccgcagcc gaacgaccga gcgcagcgag tcagtgagcg aggaagcgct      60
gcaggtccga cttcagagga ttcgatgacg cttgtttcat gcaggatgac gatcaactgc     120
cattttattg ttaccggact ggcgatgtac cgatggcgga tgtagcggag aaaaagggcg     180
cctgggattt tctgcaaaaa cccgtcgatc cgggcaagct ttttgatatt aattgaagac     240
gcgctacgcc agcgccggtt cggtattgca cggcggcaat attgccagca gacgttacag     300
gtttgaactg attgggcgca gcgagtggat gaatcagttt cgacaacggt tacaacaact     360
ggcggaaacg gacattgccg tatggtttta cggttgagca tggcactcgg acgtatgact     420
cggcgcccgt tatctcctca actggggcgt aacgcgaaag ggccgtttgt acgctatgaa     480
cttacgccgg agaatgccgg gcagttggag acattcatcg accaggcgca aggaggcacg     540
ctggtgttga gtcatcccga atatctgaca cgcgaacagc agcaccatct ggcgcgttta     600
caaagcctgg agcatcggcc ttttcgtttg gtgggcgttg gcagcgcttc gctggtggag     660
caggcggcag ctaaccagat tgcagccgag ctttactact gtttcgccat gacccaaatc     720
gcctgccagt ctcttttctca gcgaccggat gatatcgagc cgttatttcg ccattatctt     780
cgaaaagcct gcctgcgact caatcatcca gtgccggaaa tagcggggga attactgaaa     840
ggaataatgc gacgcgcctg gcctagcaat gtgcgcgaac tggctaatgc ggcagagctt     900
tttgctgttg gcgtgctgcc gctggcggaa acggtcaacc cgcagttgct tcttcaggag     960
ccgaccccgc ttgaccggcg cgttgaagag tatgagcgac aaatcattac cgaagcatta    1020
aatattcatc agggacgaat taatgaagtg gcggagtacc tgcaaattcc ccgtaaaaaa    1080
```

-continued

```
ctttatctgc gcatgaaaaa aataggtcta agtaaaaagc attataaatt ctgatattac   1140
agttactttc aatctggctg acaacatcag caacgatgtc gttagccaga taacgtcgca   1200
tcaccgtaag gtaaatcatt ccatcatgat tatagattgc ttattattca cctgggcatc   1260
aaattctatt tcttaacttc aatataggta aaaagcgtca agttctctgg cgtaataaat   1320
gtactcttgt ccgacgattt gacaagatga aaacttcatc ccctctccag attacatctg   1380
aatatgagga caagagaaat gaaaaaacat gctattgcag taatgatgat ccccgggtac   1440
ctagaattaa gaggagaaat gaaaaatt                                      1468
```

<210> SEQ ID NO 4
<211> LENGTH: 837
<212> TYPE: DNA
<213> ORGANISM: Salmonella Typhimurium

<400> SEQUENCE: 4

```
tgggacaact ccagtgaaaa gttcttctcc tttacgcatg cttaatttct cctctttaat     60
tctaggtacc cggggatcgt cattcaaaat tcgaagcgac aacatttgca ggcgcgctaa    120
aacgttctcc atacgccgcc tcaagcacag gaataatttt agtgcccgtg tcgattccta    180
cctcatccaa aagttggatt ggccccaccg gaaaaccaaa ttttaccagg gcggcgtcaa    240
tatgttcgac gcgttcgcct tcagtcagca tccgaatcgc tcattgata tatgcgcaa     300 gaattcggtt aacataaaac ccggctttat cactgacgac tatcggggtt ttaccctgtt    360
ttttcgccag cttaacggtc gtggcgatgg tctgcgcgga agtagacgca tgaggaataa    420
cctcaaccag cggcattttt tcgaccgggc taaaaaagtg caatccaatc acctgttccg    480
gtctggccgc attcgccgca atatcgccaa tcggcaggga agaagtattg gaggcaaaaa    540
tggtgtgagc agcgcaattt tgctccactt ccgccaccat ctgttgtttt aacggcagat    600
cttcaaacac cgcttcaatg accagatcac gatgactgaa accacggtaa tcggtcgaac    660
ctgatatcaa cgccaactgt ttatcgcgtt cgctggcttt gatatggcgg cggcgtactt    720
ttgtttcaag cagatcctct agagtcgacc tgcagcgctt cctcgctcac tgactcgctg    780
cgctcggtcg ttcggctgcg gcgagcggtt acagctcact caaaggcggt aatacgg      837
```

<210> SEQ ID NO 5
<211> LENGTH: 577
<212> TYPE: DNA
<213> ORGANISM: Salmonella Typhimurium

<400> SEQUENCE: 5

```
tgggacaact cccagtgaaa agttcttctc ctttacgcat gcttaatttc tcctctttaa     60
ttctaggtac ccggggatca tatcccagag ccgcagaagc ttcagcaaac gtttcttcta    120
cgatagggta atttgccgcc atctcggcca acatcccaac gctctgagaa ccctgaccgg    180
ggaacacaaa tgcaaattgc gtcatgttta atccttata ctagaaacga atcagcgcgg     240
agccccaggt gaatccaccc ccgaaggctt caagcaatac cagctgaccg gctttaattc    300
gcccgtcacg cacggcttca tccagcgcgc acggcacaga agccgcggag gtattgccgt    360
gcctgtccag cgtgacgacg acattgtcca tcgacatgcc gagttttttc gctgtcgcgc    420
taatgatacg caggttagcc tgatgcggca ccagccaatc gagttctgag cgatcctcta    480
gagtcgacct gcagcgcttc ctcgctcact gactcgctgc gctcggtcgt tcggcttgcg    540
gcgagcggaa tcagctcact caaaggcggt aatacga                             577
```

<210> SEQ ID NO 6
<211> LENGTH: 689
<212> TYPE: DNA
<213> ORGANISM: Salmonella Typhimurium

<400> SEQUENCE: 6

| | | | | | |
|---|---|---|---|---|---|
| gcagccgaac | gaccgagcgc | agcgagtcag | tgagcgagga | agcgctgcag | gtcgactcta | 60 |
| gaggagctgg | tgctgacctg | taccgacaac | cagtcgcgca | accgtcgttt | tggcatgatg | 120 |
| cttggccagg | gcatggacgt | taaaggcgcg | caggataaga | ttggccaggt | ggtcgaaggc | 180 |
| tatcgcaata | cgaaagaagt | tcgtgaattg | gcgcaccgtt | ttggtgttga | aatgccaata | 240 |
| accgaggaaa | tttatcaagt | attgtattgc | ggaaaaaacg | cgcgcgaggc | agcattaacg | 300 |
| ttattaggtc | gcgcccgcaa | ggaagagctg | agtcgccact | agccgtaagg | aactgtttgc | 360 |
| tataacgacc | caacccgcac | agaacgggtt | ggtcgttttc | tgcccgtctg | gagtaagcca | 420 |
| tgccgtgtga | agaactggaa | atcgtctgga | agaatattaa | agctgaagcc | cgcgctttag | 480 |
| ctgactgtga | gcctatgttg | gccagttttt | atcacgccac | gctactcaag | catgaaaatc | 540 |
| tgggcagtgc | gctgagctat | atgctggcaa | ataaactggc | ttcgcccatc | atgcccgcta | 600 |
| tcgctatccg | tgaagtagtt | gaagaagcct | atgccgccgt | acccgaaaat | gatccccggg | 660 |
| tacctagaat | taaagaggag | aaattaagc | | | | 689 |

<210> SEQ ID NO 7
<211> LENGTH: 979
<212> TYPE: DNA
<213> ORGANISM: Salmonella Typhimurium

<400> SEQUENCE: 7

| | | | | | |
|---|---|---|---|---|---|
| tcgtaacccg | tccgccgcag | tccgaacgac | acgagccgca | gcgagtcagt | gagtcgagga | 60 |
| agcgctgcag | gtcgacttca | gaggatcgct | gacgctaaga | ccatcggcgc | gaatcacctg | 120 |
| cgggcccagg | ctatgcgcgg | gaaagtgagc | gtcggaaaaa | atgatttcgt | ccccgtggcc | 180 |
| catctcggcc | agcactttga | gcagtgtcgg | ggaaattaac | ggtgaaatgg | ttttagctt | 240 |
| tcatactccc | tcaataattt | caggttcggt | ttgcggccag | aaataacgat | actgataatt | 300 |
| gacctgcgcg | cgcgcctgtt | ccgggctact | aaattcgcct | acgccgtacc | agccaaacat | 360 |
| ggcagcgccg | gccacggtgg | ttttcgcgtc | gtccagcact | ttgatagggga | tatcaagctg | 420 |
| attcgcttta | atttgattcc | taaagcgtta | gcgactgccg | ccgccaacca | gtaacagttc | 480 |
| tgtggcgtta | aaatggccga | ttttctccag | cgtgcgcaga | ttacgctgaa | gttgcgccgt | 540 |
| caggccttcc | agcgcggcgc | gatagaaatg | gccgcgggtg | gtattgagcg | tcacgccctg | 600 |
| ccagcctgca | ttttggcagg | cgagcagatc | gcactgcatc | cgacgccttc | gcgccagcg | 660 |
| ggaatagcgc | gcgcttcgtc | gatcagcgtt | tgccatggcg | ttccggcgtc | cacagcagtt | 720 |
| tcgtacccat | tcgagtacac | cggaggccag | ccactgcatt | ccggggttat | aaagccccga | 780 |
| ctgactgttc | agttacaggt | cagcccgata | ctgactgagc | agcgaggtat | ccacttgacc | 840 |
| gctgcgcacc | atcagatctc | catgttccgg | aggagagcac | cgttaccctg | ctgcgcgcca | 900 |
| gcgccgataa | cgcgaactcg | agtatccgtc | gccagaaata | ccattaaggc | atccggaatt | 960 |
| aatatattgc | cgccaggcc | | | | | 979 |

<210> SEQ ID NO 8
<211> LENGTH: 864
<212> TYPE: DNA
<213> ORGANISM: Salmonella Typhimurium -continued

```
<400> SEQUENCE: 8
acaatttcct catcttaatt tcaggtaccc ggggatccgg gtactataga gcccaatcca      60
acacggggaa gtgttcgtta ctgaagacgg cgctgaaacc gacctggacc tggggcacta     120
cgagcgtttc atccgcacca agatgtctcg ccgcaacaac tttcacgact ggccgcatct     180
actccgacgt tctgcgtaaa gaacgccgtg gcgactatct gggcgcaacc gtacaggtca     240
tccctcacat cactaacgcg attaaagagc gcgtgctgga aggtggcgaa ggccacgatg     300
tggtactggt ggaaatcggc ggtaccgtcg gtgatatcga atcgctgccg tttcttgagg     360
cgattcgtca attggcggta gatattcggt cgtgaacacg cgctgtttat gcacctgacg     420
ctggtacctt acctggcggc tgcgggcgaa gtgaaaacta aaccgactca gcactccgtg     480
aaagagctgc tgtctatcgg tattcagccc gatattctga tttgtcgttc cgatcgcgcg     540
gttcctgcca acgagcgtgc aaaaattgca ttgttctgta atgtgccgga aaaagccgtt     600
atttcaatga agatgtcga ttccatttat aaaattccgg gcctgttgaa atctcagggg     660
cttgatgatt atatttgtaa acgattcagc ttgaactgtc cggaagctaa cctgtctgaa     720
tgggaacagg tcatttacga agaagcgaac ccggcaggcg aagtgactat cggcatggtc     780
ggcaaatata tttgaactgc cggatgccta agtcggtg atctctgccg gacacgatac     840
tcagttcgcg ttattcgcgc tggc                                           864

<210> SEQ ID NO 9
<211> LENGTH: 2211
<212> TYPE: DNA
<213> ORGANISM: Bacillus Anthracis

<400> SEQUENCE: 9
atggaagtta acaggagaa ccggttatta atgaatcag atcaagttc ccaggggtta       60 ctaggatact attttagtga tttgaatttt caagcaccca tggtggttac ctcttctact     120 acagggatt tatctattcc tagttctgag ttagaaaata ttccatcgga aaaccaatat     180
tttcaatctg ctatttggtc aggatttatc aaagttaaga agagtgatga atatacattt     240
gctacttccg ctgataatca tgtaacaatg tgggtagatg accaagaagt gattaataaa     300
gcttctaatt ctaacaaaat cagattagaa aaaggaagat tatatcaaat aaaaattcaa     360
tatcaacgag aaaatcctac tgaaaaagga ttggatttca gttgtactg gaccgattct     420 caaaataaaa agaagtgat ttctagtgat aacttacaat tgccagaatt aaaacaaaaa     480
tcttcgaact caagaaaaa gcgaagtaca agtgctggac ctacggttcc agaccgtgac     540
aatgatggaa tccctgattc attagaggta gaaggatata cggttgatgt caaaaataaa     600 agaactttc ttccaccatg gatttctaat attcatgaaa agaaaggatt aaccaaatat     660
aaatcatctc ctgaaaatg gagcacggct tctgatccgt acagtgattt cgaaaaggtt     720
acaggacgga ttgataagaa tgtatcacca gaggcaagac accccttgt ggcagcttat     780 ccgattgtac atgtagatat ggagaatatt attctctcaa aaatgagga tcaatccaca     840 cagaatactg atagtcaaac gagaacaata agtaaaata cttctacaag taggacacat     900
actagtgaag tacatggaaa tgcagaagtg catgcgtcgt tctttgatat tggtgggagt     960
gtatctgcag gatttagtaa ttcgaattca agtacggtcg caattgatca ttcactatct    1020
ctagcagggg aaagaacttg ggctgaaaca atggggttta aataccgctga tacagcaaga    1080 ttaaatgcca atattgagata tgtaaatact gggacggctc caatctacaa cgtgttacca    1140
acgacttcgt tagtgttagg aaaaaatcaa acactcgcga caattaaagc taaggaaaac    1200
```

| caattaagtc aaatacttgc acctaataat tattatcctt ctaaaaactt ggcgccaatc | 1260 |
| gcattaaatg cacaagacga tttcagttct actccaatta caatgaatta caatcaattt | 1320 |
| cttgagttag aaaaaacgaa acaattaaga ttagatacgg atcaagtata tgggaatata | 1380 |
| gcaacataca attttgaaaa tggaagagtg agggtggata caggctcgaa ctggagtgaa | 1440 |
| gtgttaccgc aaattcaaga aacaactgca cgtatcattt ttaatggaaa agatttaaat | 1500 |
| ctggtagaaa ggcggatagc ggcggttaat cctagtgatc cattagaaac gactaaaccg | 1560 |
| gatatgacat aaaagaagc ccttaaaata gcatttggat ttaacgaacc gaatggaaac | 1620 |
| ttacaatatc aagggaaaga cataaccgaa tttgatttta atttcgatca acaaacatct | 1680 |
| caaaatatca gaatcagtt agcggaatta aacgcaacta acatatatac tgtattagat | 1740 |
| aaaatcaaat taaatgcaaa aatgaatatt ttaataagag ataaacgttt tcattatgat | 1800 |
| agaaataaca tagcagttgg ggcggatgag tcagtagtta aggaggctca tagagaagta | 1860 |
| attaattcgt caacagaggg attattgtta aatattgata aggatataag aaaaatatta | 1920 |
| tcaggttata ttgtagaaat tgaagatact gaagggctta agaagttat aaatgacaga | 1980 |
| tatgatatgt tgaatatttc tagtttacgg caagatggaa aaacatttat agatttaaa | 2040 |
| aaatataatg ataaattacc gttatatata agtaatccca attataaggt aaatgtatat | 2100 |
| gctgttacta agaaaacac tattattaat cctagtgaga tgggatac tagtaccaac | 2160 |
| gggatcaaga aatttaat cttttctaaa aaaggctatg agataggata a | 2211 |

<210> SEQ ID NO 10
<211> LENGTH: 2202
<212> TYPE: DNA
<213> ORGANISM: Artificial Sequence
<220> FEATURE:
<223> OTHER INFORMATION: codon-modified sequence for B. anthracis protective antigen

<400> SEQUENCE: 10

| gaagttaaac aggagaaccg tctgctgaat gaatcagaat caagttccca gggtctgctg | 60 |
| ggctactatt ttagtgatct gaattttcaa gcaccgatgg tggttacttc ttctactaca | 120 |
| ggtgatctgt ctattccgag ttctgagctg gaaaatattc cgtcggaaaa ccaatatttt | 180 |
| caatctgcta tttggtcagg ctttatcaaa gttaagaaga gtgatgaata cattttgct | 240 |
| acttccgctg ataatcatgt aacaatgtgg gtagatgacc aagaagtgat taataaagct | 300 |
| tctaattcta caaaatccg cctggaaaaa ggccgcctgt atcaaatcaa aattcaatat | 360 |
| caacgtgaaa atccgactga aaaggcctg gatttcaagc tgtactggac cgattctcaa | 420 |
| aataaaaaag aagtgattc tagtgataac ctgcaactgc ggaactgaa acaaaaatct | 480 |
| tcgaactcaa gcaacaagga gagtacaagt gctggtccga cggttccgga ccgtgacaat | 540 |
| gatggtatcc cggattcact ggaggtagaa ggttatacgg ttgatgtcaa aaataaacgt | 600 |
| acttttctgt caccgtggat ttctaatatt catgaaaaga aaggcctgac caaatataaa | 660 |
| tcatctccgg aaaaatggag cacggcttct gatccgtaca gtgatttcga aaaggttaca | 720 |
| ggccgtattg ataagaatgt atcaccggag gcacgccacc cgctggtggc agcttatccg | 780 |
| attgtacatg tagatatgga aatattatt ctgtcaaaaa atgaggatca atccacacag | 840 |
| aatactgata gtgaaacgcg cacaatcagt aaaaatactt ctacaagtcg tacacatact | 900 |
| agtgaagtac atggtaatgc agacgtgcat gcgtcggata ttggtggcag tgtatctgca | 960 |
| ggttttagta attcgaattc aagtacggtc gcaattgatc attcactgtc tctggcaggc | 1020 |

```
gaacgtactt gggctgaaac aatgggtctg aataccgctg atacagcacg cctgaatgcc    1080
aatattcgtt atgtaaatac tggcacggct ccgatctaca acgtgctgcc gacgacttcg    1140
ctggtgctgg gtaaaaatca aacactggcg acaattaaag ctaaggaaaa ccaactgagt    1200
caaatcctgg caccgaataa ttattatccg tctaaaaacc tggcgccgat cgcactgaat    1260
gcacaagacg atttcagttc tactccgatt acaatgaatt acaatcaatt tctggagctg    1320
gaaaaaacga aacaactgcg tctggatacg gatcaagtat atggcaatat cgcaacatac    1380
aattttgaaa atggtcgcgt gcgtgtggat acaggctcga actggagtga agtgctgccg    1440
caaattcaag aaacaactgc acgtatcatt tttaatggta aagatctgaa tctggtagaa    1500
cgtcgcattg cggcggttaa tccgagtgat ccgctggaaa cgactaaacc ggatatgaca    1560
ctgaaagaag ccctgaaaat cgcatttggt tttaacgaac gaatggcaa cctgcaatat    1620 caaggcaaag acattaccga atttgatttt aatttcgatc aacaaacatc tcaaaatatc    1680
aagaatcagc tggcggaact gaacgcaact aacatctata ctgtactgga taaaatcaaa    1740
ctgaatgcaa aaatgaatat tctgattcgc gataaacgtt ttcattatga tcgtaataac    1800
attgcagttg gcgcggatga gtcagtagtt aaggaggctc atcgcgaagt aattaattcg    1860
tcaacagagg gcctgctgct gaatattgat aaggatatcc gcaaaatcct gtcaggttat    1920
attgtagaaa ttgaagatac tgaaggcctg aaagaagtta ttaatgaccg ctatgatatg    1980
ctgaatattt ctagtctgcg ccaagatggt aaaacattta tcgattttaa aaatataat    2040 gataaactgc cgctgtatat cagtaatccg aattataagg taaatgtata tgctgttact    2100
aaagaaaaca ctattattaa tccgagtgag aatggcgata ctagtaccaa cggcatcaag    2160
aaaattctga tcttttctaa aaaaggctat gagattggct aa                       2202

<210> SEQ ID NO 11
<211> LENGTH: 134
<212> TYPE: DNA
<213> ORGANISM: Artificial Sequence
<220> FEATURE:
<223> OTHER INFORMATION: promoter-less GFP mut3.1 sequence

<400> SEQUENCE: 11
atgaccatga ttacgccaag cttgcatgcc tgcaggtcga ctctagagga tccccgggta    60
cctagaatta agaggagaa attaagcatg cgttaagctt aattagctga cctactagtc    120
ggccgtacgg gccc                                                       134

<210> SEQ ID NO 12
<211> LENGTH: 103
<212> TYPE: DNA
<213> ORGANISM: Artificial Sequence
<220> FEATURE:
<223> OTHER INFORMATION: synthetic nirB promoter

<400> SEQUENCE: 12
gaattcaggt aaatttgatg tacatcaaat ggtacccctt gctgaatcgt taaggtaggc    60
ggtagggccc agatcttaat catccacagg agactttctg atg                      103

<210> SEQ ID NO 13
<211> LENGTH: 59
<212> TYPE: DNA
<213> ORGANISM: Artificial Sequence
<220> FEATURE:
<223> OTHER INFORMATION: synthetic oligonucleotide
```

```
<400> SEQUENCE: 13
gaattccgct ctagagcggt aaatttgatg tacatcaaat ggtacccctt gctgaatcg        59

<210> SEQ ID NO 14
<211> LENGTH: 58
<212> TYPE: DNA
<213> ORGANISM: Artificial Sequence
<220> FEATURE:
<223> OTHER INFORMATION: synthetic oligonucleotide

<400> SEQUENCE: 14
cccccgggtt aagatctggg ccctaccgcc taccttaacg attcagcaag gggtacca         58

<210> SEQ ID NO 15
<211> LENGTH: 52
<212> TYPE: DNA
<213> ORGANISM: Artificial Sequence
<220> FEATURE:
<223> OTHER INFORMATION: synthetic primer

<400> SEQUENCE: 15
ggaagatctt aatcatccac aggagacttt ctgatggaag ttaaaacagg aa               52

<210> SEQ ID NO 16
<211> LENGTH: 28
<212> TYPE: DNA
<213> ORGANISM: Artificial Sequence
<220> FEATURE:
<223> OTHER INFORMATION: synthetic primer

<400> SEQUENCE: 16
cgggatcccg gtttaaaaca tactctcc                                          28

<210> SEQ ID NO 17
<211> LENGTH: 20
<212> TYPE: DNA
<213> ORGANISM: Artificial Sequence
<220> FEATURE:
<223> OTHER INFORMATION: synthetic primer

<400> SEQUENCE: 17
cgtattaccg cctttgagtg                                                   20

<210> SEQ ID NO 18
<211> LENGTH: 20
<212> TYPE: DNA
<213> ORGANISM: Artificial Sequence
<220> FEATURE:
<223> OTHER INFORMATION: synthetic primer

<400> SEQUENCE: 18
gggacaactc cagtgaaaag                                                   20

<210> SEQ ID NO 19
<211> LENGTH: 60
<212> TYPE: DNA
<213> ORGANISM: Artificial Sequence
<220> FEATURE:
<223> OTHER INFORMATION: synthetic promoter

<400> SEQUENCE: 19
ggaattccgc tctagagcgg taaatttgat gtacatcaaa tggtacccct tgctgaatcg       60

<210> SEQ ID NO 20
<211> LENGTH: 59
```

<212> TYPE: DNA
<213> ORGANISM: Artificial Sequence
<220> FEATURE:
<223> OTHER INFORMATION: synthetic promoter

<400> SEQUENCE: 20
tcccccgggt aagatctgg gccctaccgc ctaccttaac gattcagcaa ggggtacca          59

<210> SEQ ID NO 21
<211> LENGTH: 20
<212> TYPE: DNA
<213> ORGANISM: Artificial Sequence
<220> FEATURE:
<223> OTHER INFORMATION: synthetic promoter

<400> SEQUENCE: 21
ggaattccgc tctagagcgg          20

<210> SEQ ID NO 22
<211> LENGTH: 20
<212> TYPE: DNA
<213> ORGANISM: Artificial Sequence
<220> FEATURE:
<223> OTHER INFORMATION: synthetic promoter

<400> SEQUENCE: 22
tcccccggga ttaagatctg          20

<210> SEQ ID NO 23
<211> LENGTH: 42
<212> TYPE: DNA
<213> ORGANISM: Artificial Sequence
<220> FEATURE:
<223> OTHER INFORMATION: synthetic primer

<400> SEQUENCE: 23
ctggtggtgc cgttctatag ccatagcgaa gttaaacagg aa          42

<210> SEQ ID NO 24
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 24
cgggatcccg tcacctagaa ttacc          25

<210> SEQ ID NO 25
<211> LENGTH: 39
<212> TYPE: DNA
<213> ORGANISM: Artificial Sequence
<220> FEATURE:
<223> OTHER INFORMATION: synthetic primer

<400> SEQUENCE: 25
atgaaaaaac tgctgttcgc gattccgctg gtggtgccg          39

<210> SEQ ID NO 26
<211> LENGTH: 48
<212> TYPE: DNA
<213> ORGANISM: Artificial Sequence
<220> FEATURE:
<223> OTHER INFORMATION: synthetic primer

<400> SEQUENCE: 26

```
ggaagatctt aatcatccac aggagacttt ctgatgaaaa aactgctg          48
```

\<210\> SEQ ID NO 27
\<211\> LENGTH: 23
\<212\> TYPE: DNA
\<213\> ORGANISM: Artificial Sequence
\<220\> FEATURE:
\<223\> OTHER INFORMATION: synthetic primer

\<400\> SEQUENCE: 27

```
ggctggcttt tcttgttat cgc                                      23
```

\<210\> SEQ ID NO 28
\<211\> LENGTH: 24
\<212\> TYPE: DNA
\<213\> ORGANISM: Artificial Sequence
\<220\> FEATURE:
\<223\> OTHER INFORMATION: synthetic primer

\<400\> SEQUENCE: 28

```
ctaatgcacc cagtaaggca gcgg                                    24
```

\<210\> SEQ ID NO 29
\<211\> LENGTH: 29
\<212\> TYPE: DNA
\<213\> ORGANISM: Artificial Sequence
\<220\> FEATURE:
\<223\> OTHER INFORMATION: synthetic promoter

\<400\> SEQUENCE: 29

```
gcgcaagctt tggactttg taaagatgg                                29
```

\<210\> SEQ ID NO 30
\<211\> LENGTH: 35
\<212\> TYPE: DNA
\<213\> ORGANISM: Artificial Sequence
\<220\> FEATURE:
\<223\> OTHER INFORMATION: synthetic promoter

\<400\> SEQUENCE: 30

```
gggcatatgt cctctcctta aaattgctgt gtacg                        35
```

\<210\> SEQ ID NO 31
\<211\> LENGTH: 42
\<212\> TYPE: DNA
\<213\> ORGANISM: Artificial Sequence
\<220\> FEATURE:
\<223\> OTHER INFORMATION: synthetic primer

\<400\> SEQUENCE: 31

```
cggttttcct gtttaacttc gctatggcta tagaacggca cc                42
```

\<210\> SEQ ID NO 32
\<211\> LENGTH: 41
\<212\> TYPE: DNA
\<213\> ORGANISM: Artificial Sequence
\<220\> FEATURE:
\<223\> OTHER INFORMATION: synthetic promoter

\<400\> SEQUENCE: 32

```
gggtggcata tgaaagtctc ctgtggatga ttaagatctg g                 41
```

\<210\> SEQ ID NO 33
\<211\> LENGTH: 27
\<212\> TYPE: DNA
\<213\> ORGANISM: Artificial Sequence

```
<220> FEATURE:
<223> OTHER INFORMATION: synthetic oligonucleotide

<400> SEQUENCE: 33
cctccatatg aaaaaactgc tgttcgc                                          27

<210> SEQ ID NO 34
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 34
gataaagatg gccgggtcat cacaccagat tccc                                  34

<210> SEQ ID NO 35
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 35
cctccaccgg atccttaacg ctcatgtaaa c                                     31

<210> SEQ ID NO 36
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 36
cctccgccgt gatgcatagc caatctcata gcc                                   33
```

DNA PROMOTERS AND ANTHRAX VACCINES

RELATED APPLICATIONS

This application is a continuation of International Patent Application No.: PCT/US2004/030616, filed Sep. 20, 2004, designating the U.S. and published in English on Mar. 24, 2005 as WO 2005/026203, which claims the benefit of U.S. Provisional Application No. 60/504,504, filed Sep. 18, 2003, and U.S. Provisional Application No. 60/504,505, filed Sep. 18, 2003, all of which are hereby incorporated by reference in their entireties.

BACKGROUND OF THE INVENTION

There is a need for identifying intracellularly induced bacterial DNA promoters and for developing vaccines against *Bacillus anthracis*.

SUMMARY OF THE INVENTION

The invention is related to intracellularly induced bacterial DNA promoters and vaccines against *Bacillus anthracis*.

(SEQ ID NO: 11)
ATGACCATGATTACGCCAAGCTTGCATGCCTGCAGGTCGACTCTAGAGGAT

CCCCGGGTACCTAGAATTAAAGAGGAGAAATTAAGCATGCGTTAAGCTTAA

TTAGCTGACCTACTAGTCGGCCGTACGGGCCC.

Figure 2:
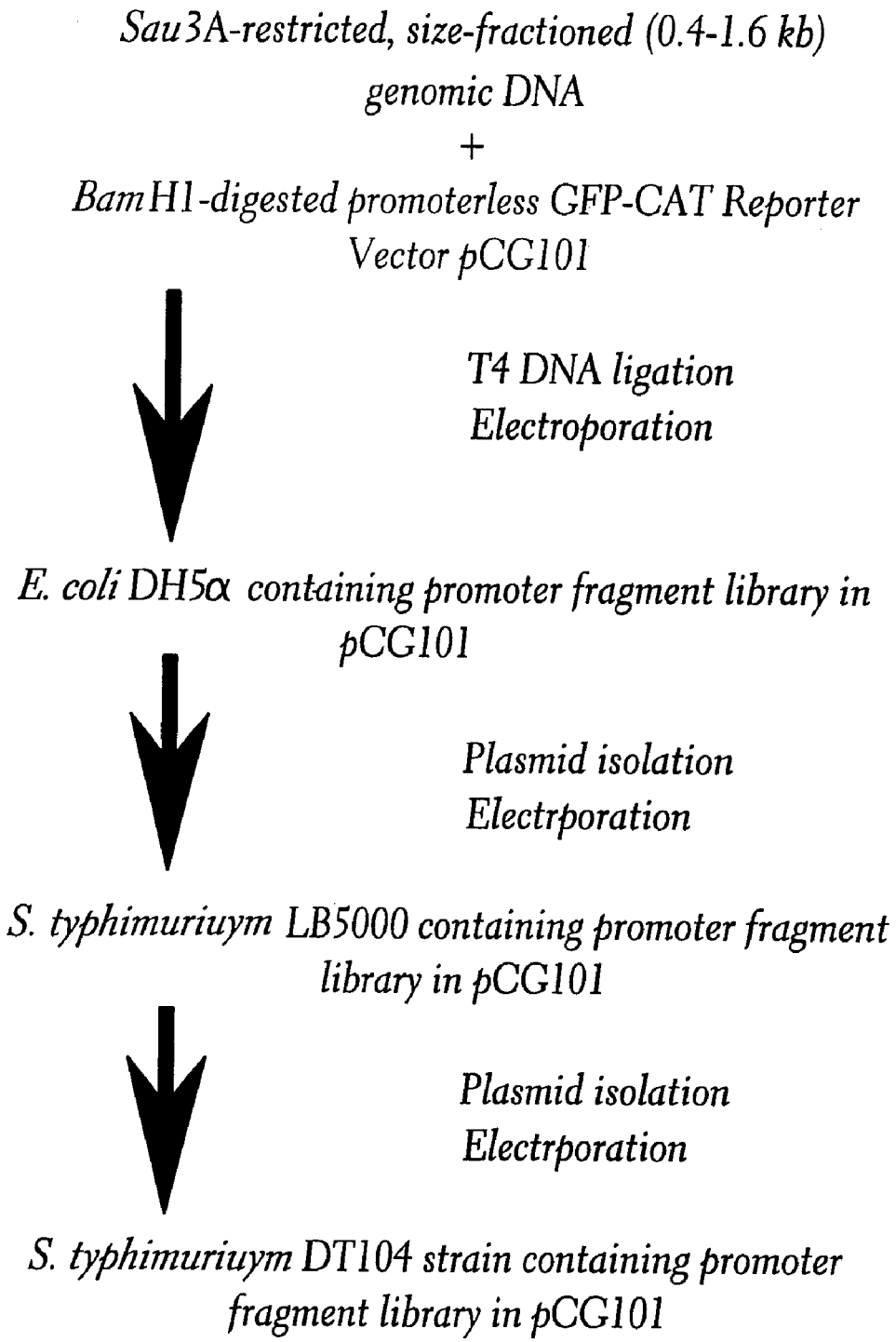
Figure 4A:
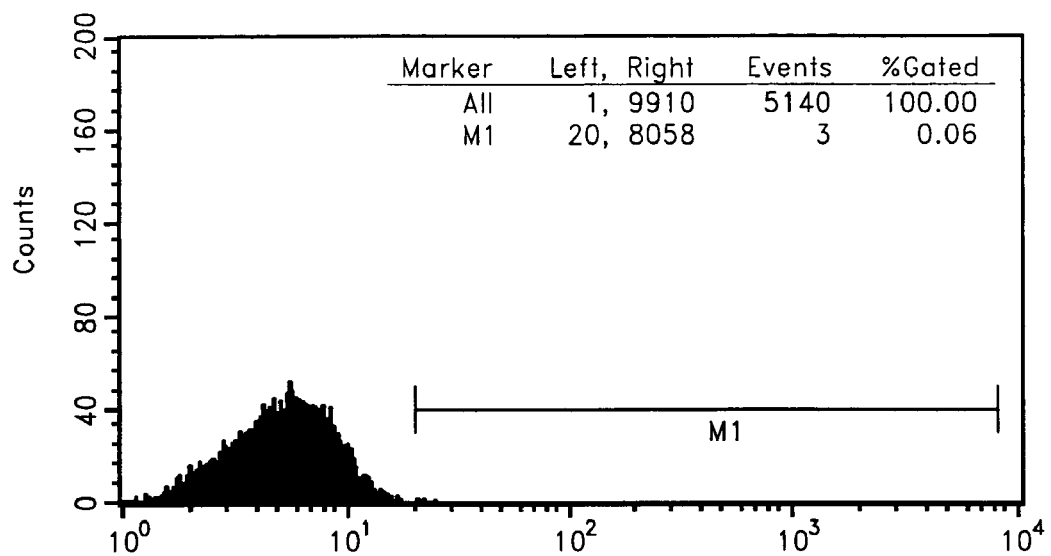
Figure 4B:
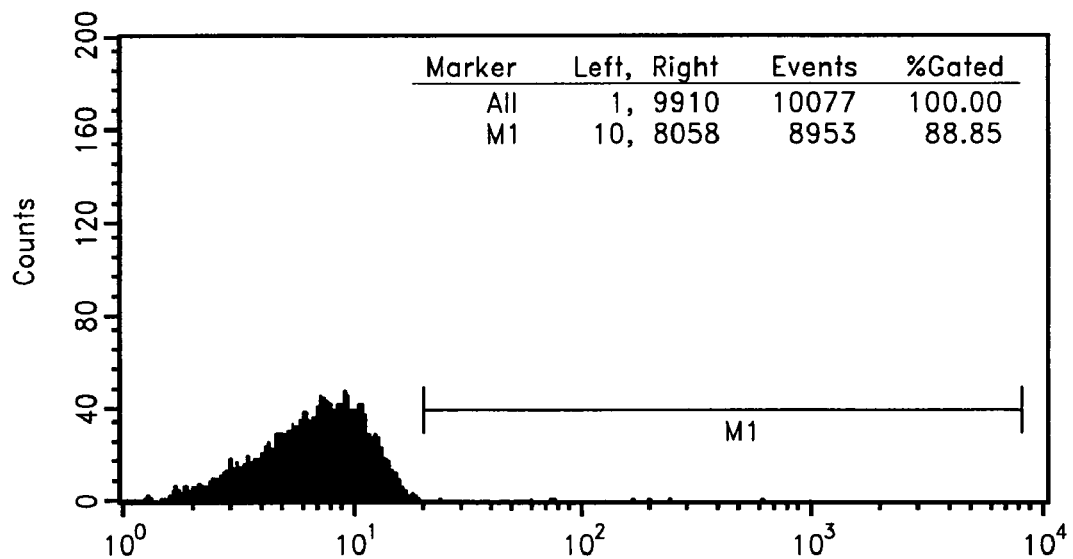
Figure 4C:
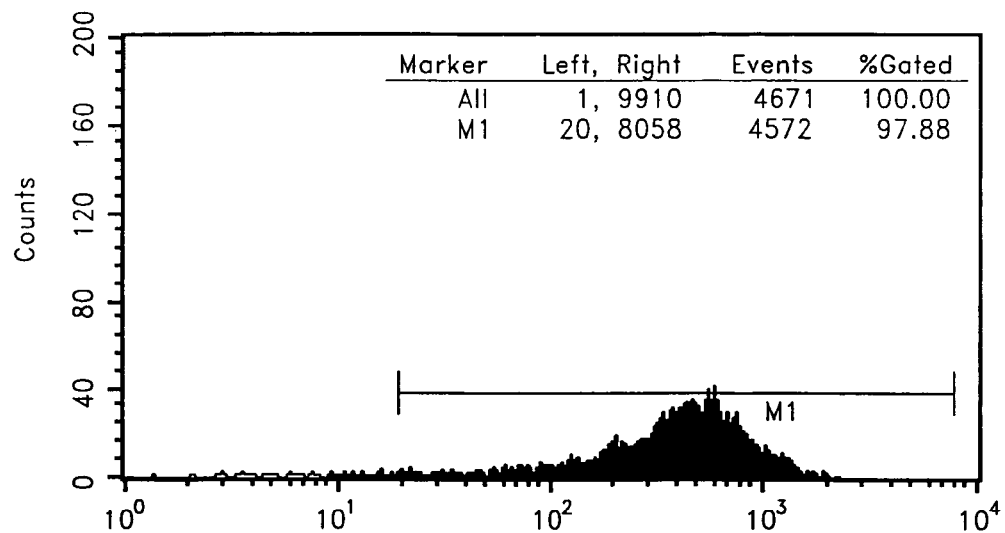
Figure 4D:
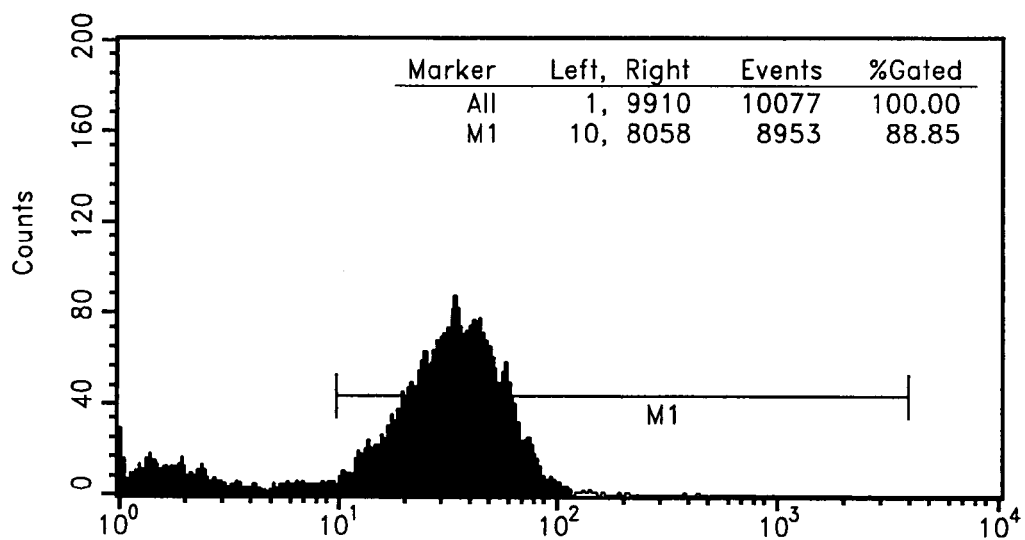

FIG. 2. Construction of *S. Typhimurium* DT104 genomic promoter fragment library in promoter trap vector pCG101.

FIG. 3. Double-selection strategy to enrich for intracellularly-activated promoter clones in INT407 epithelial cells.

FIG. 4 A-D. FACS analyses of experimental control plasmids.

Figure 5A:
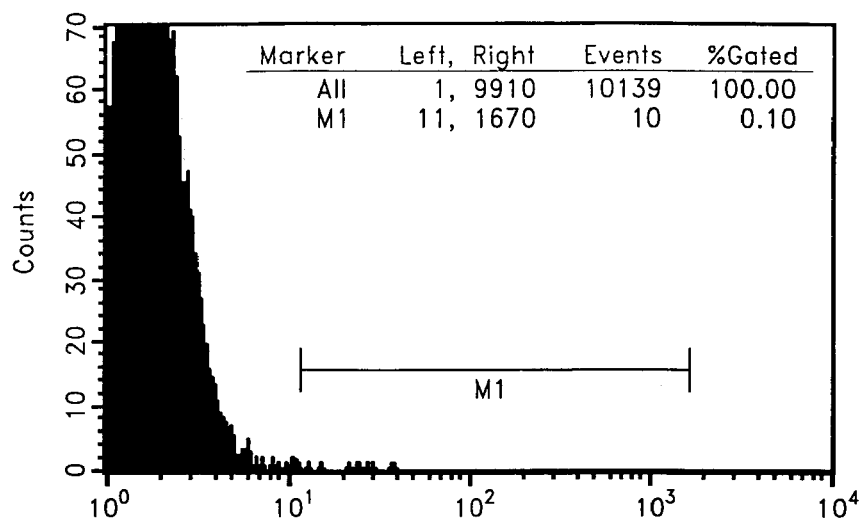
Figure 5B:
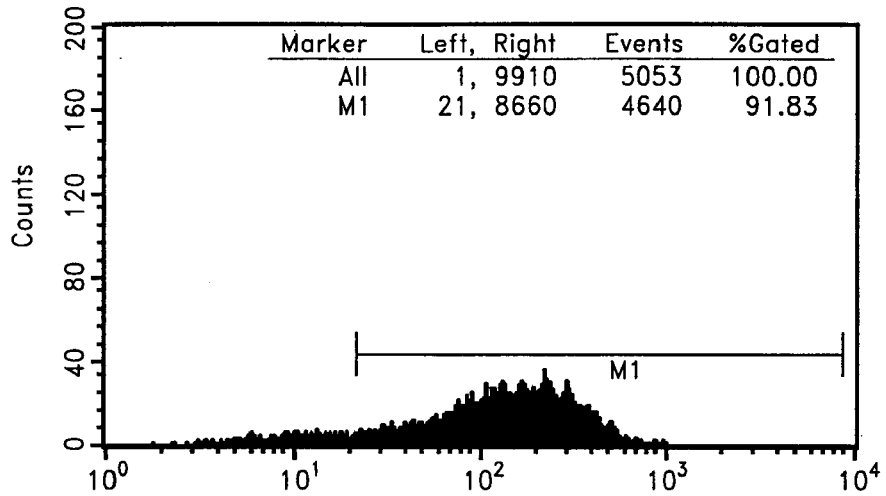
Figure 5C:
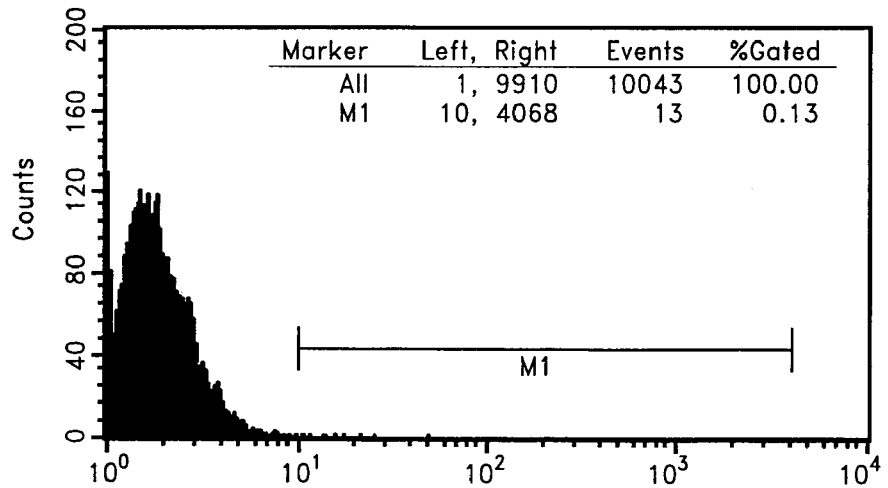

FIG. 5 A-C. FACS analyses of genomic library before and after intracellular induction.

Figure 6:
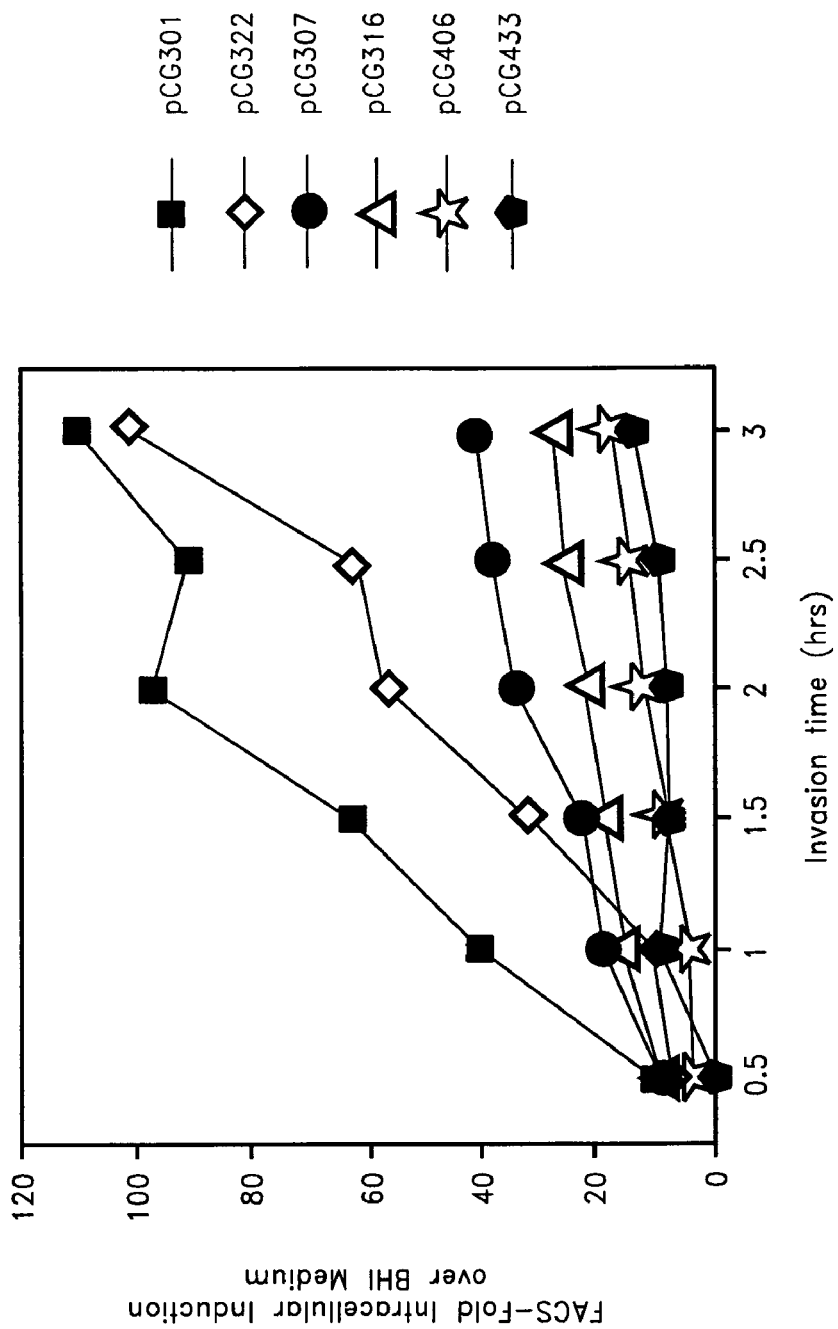

FIG. 6. Representative kinetic analyses of Fluorescence-induction mediated by promoter-fragment inserts in pCG101.

FIG. 7. Selection strategy to enrich for intracellularly-activated promoter clones in J774 macrophage cells.

FIG. 8 A-D. Intracellularly-activated promoter fragments.

Figure 9A:
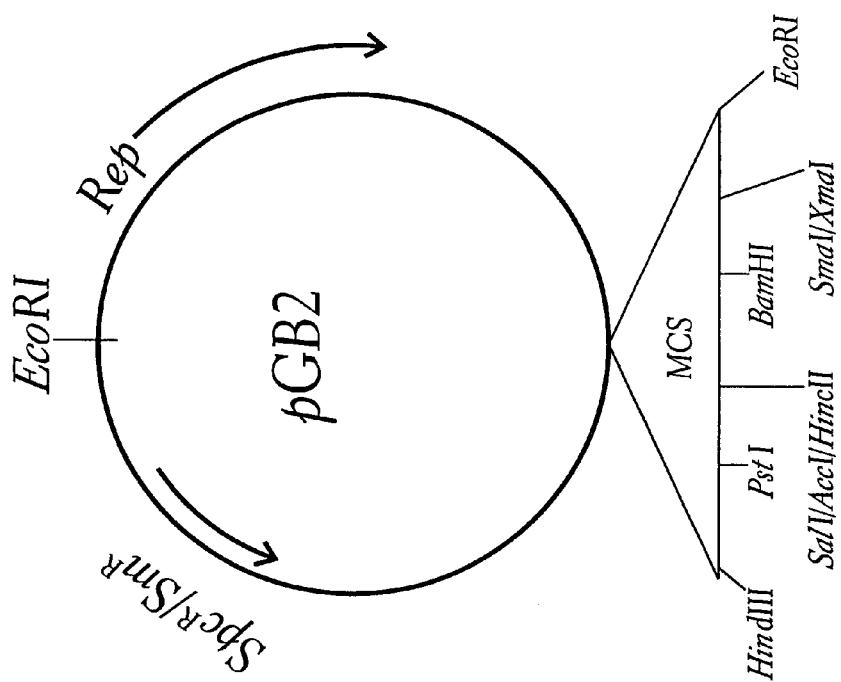
Figure 9B:
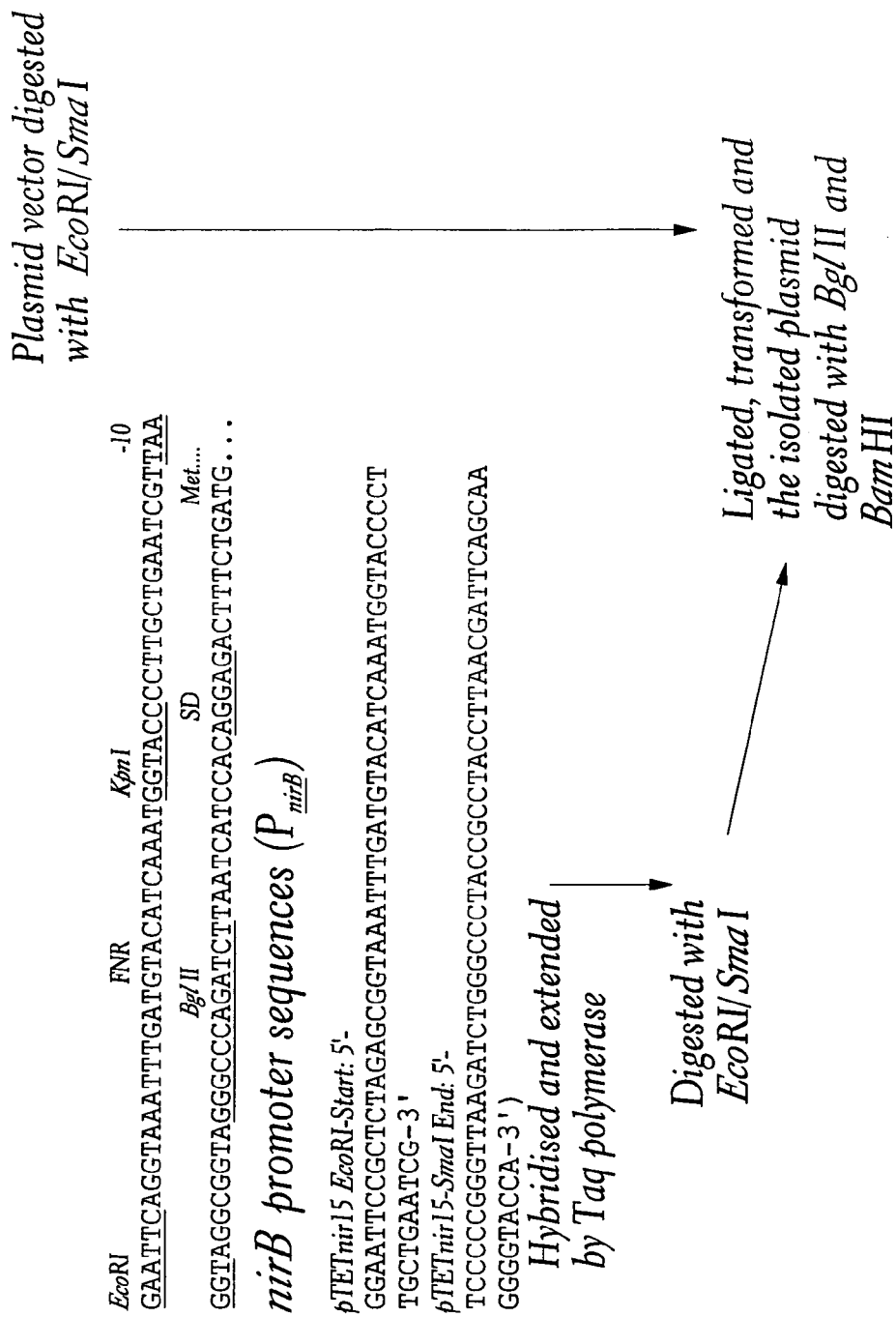

FIG. 9 A-C. Construction of pGB2/$P_{nirB}$/PA plasmid vector.

nirB Promoter Sequences:

(SEQ ID NO: 12)
GAATTCAGGTAAATTTGATGTACATCAAATGGTACCCCTTGCTGAATCGTT

AGGTAGGCGGTAGGGCCCAGATCTTAATCATCCACAGGAGACTTTCTGA

TG;

(SEQ ID NO: 13)
GAATTCCGCTCTAGAGCGGTAAATTTGATGTACATCAAATGGTACCCCTTG

CTGAATCG;

(SEQ ID NO: 14)
CCCCCGGGTTAAGATCTGGGCCCTACCGCCTACCTTAACGATTCAGCAAGG

GGTACCA.

PCR Amplification Primers for Wild Type PA:

(SEQ ID NO: 15)
GGAAGATCTTAATCATCCACAGGAGACTTTCTGATGGAAGTTAAAACAGGA

A;

(SEQ ID NO: 16)
CGGGATCCCGGTTTAAAACATACTCTCC.

Figure 10:
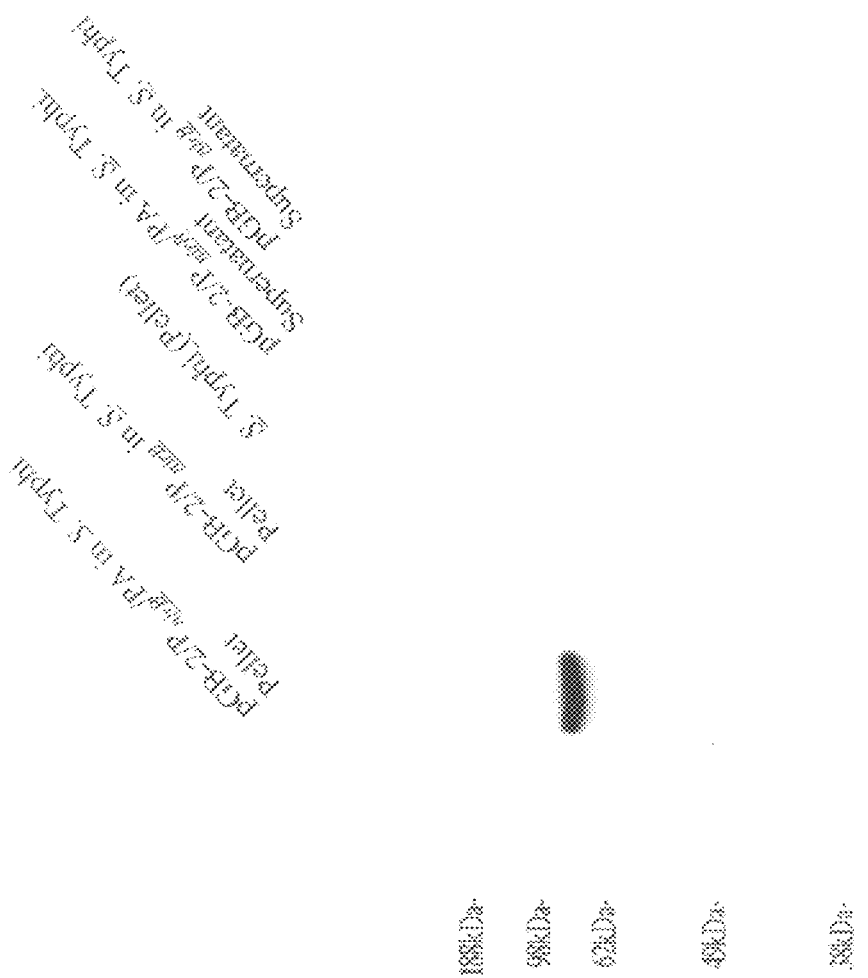

FIG. 10. Immunoblot analysis of PA expression in *S. Typhi* Ty21a.

Figure 11:
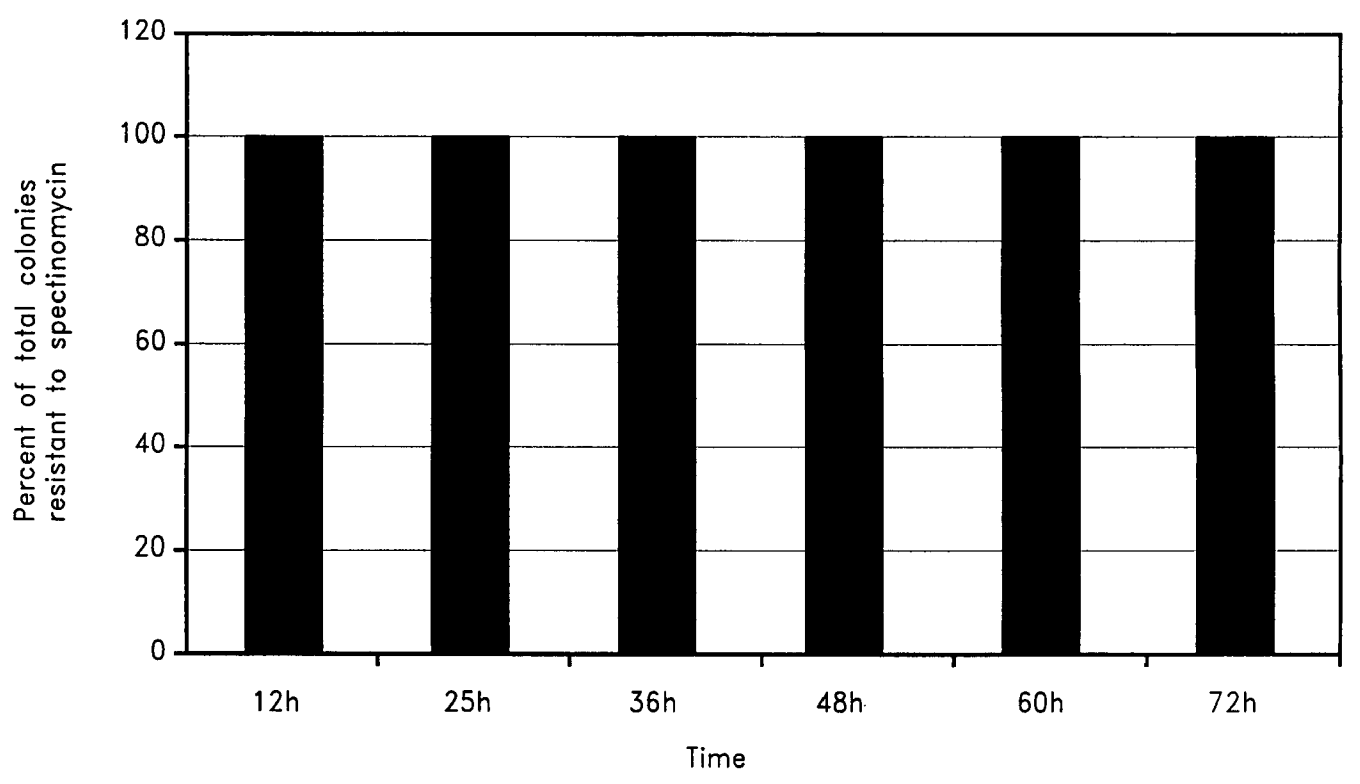

FIG. 11. Plasmid stability upon broth subculturing.

Figure 12:
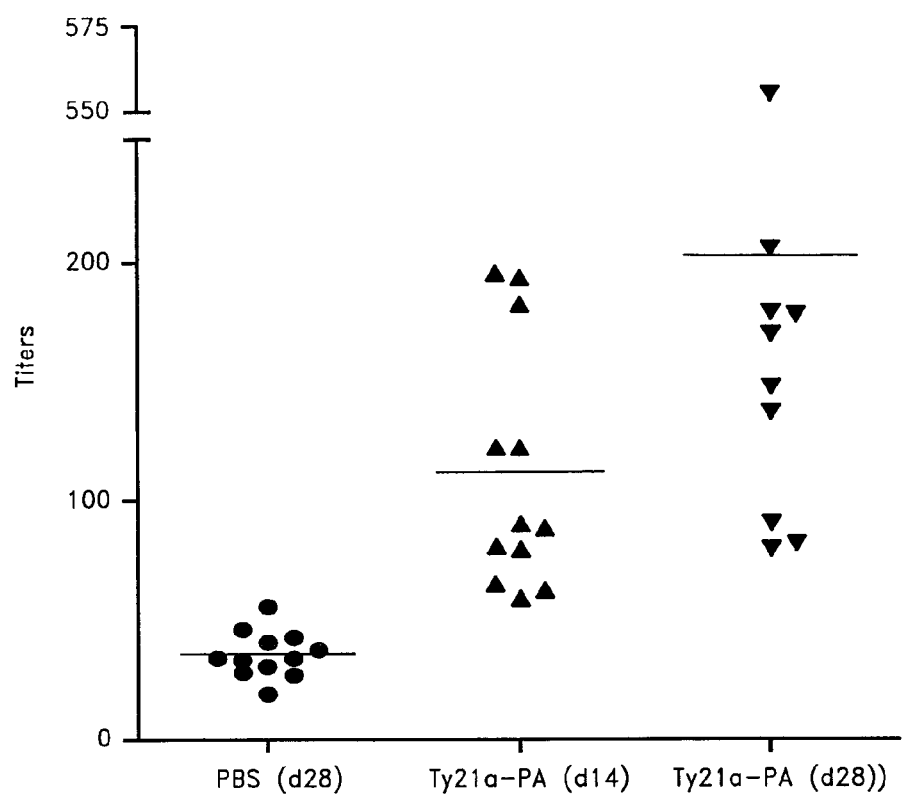

FIG. 12. Humoral anti-PA response in mice following IP immunization.

Figure 13:
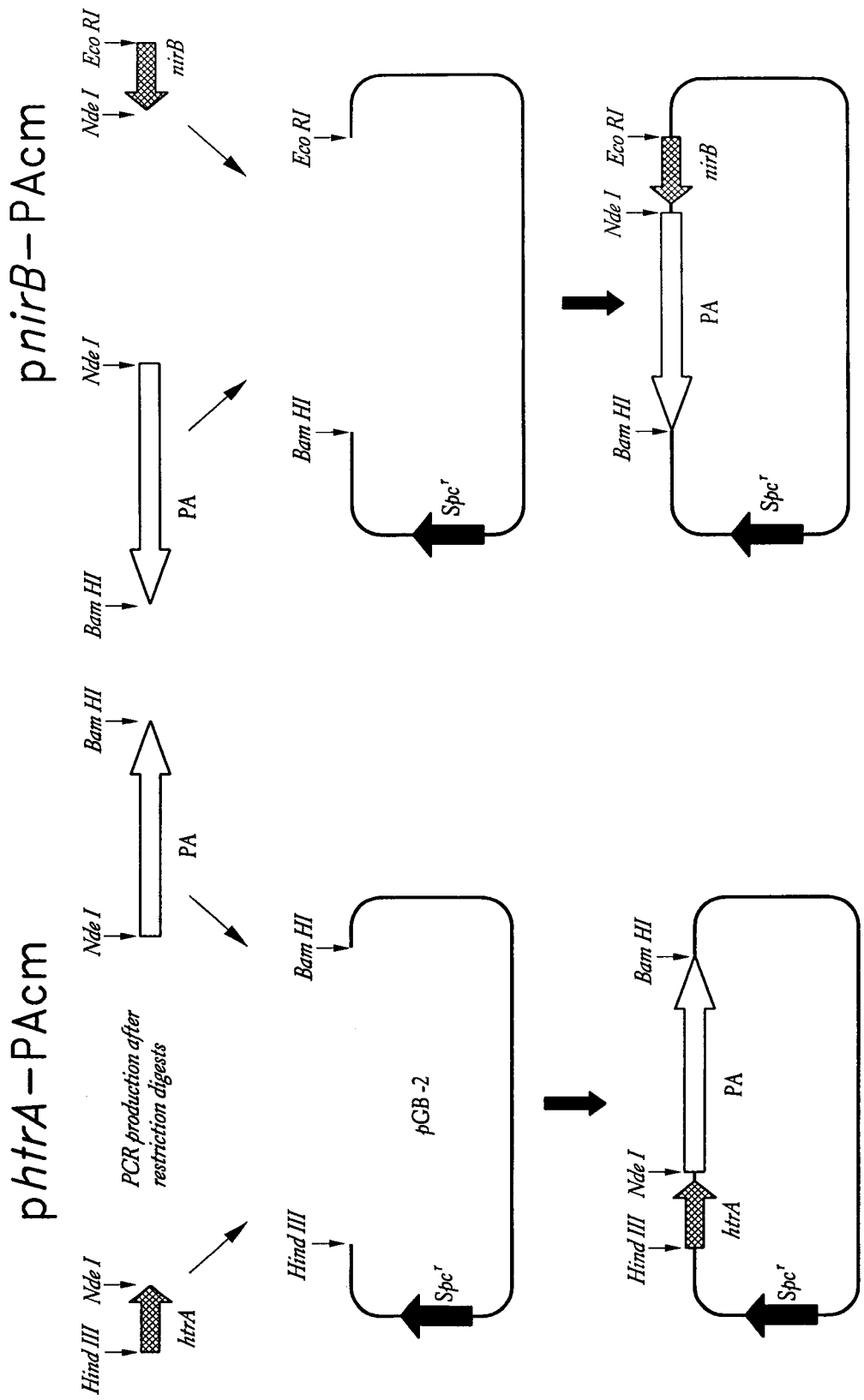

FIG. 13. Representative pGB-2 constructs with 2 promoters linked to wild type or codon-optimized PA genes.

Figure 14:
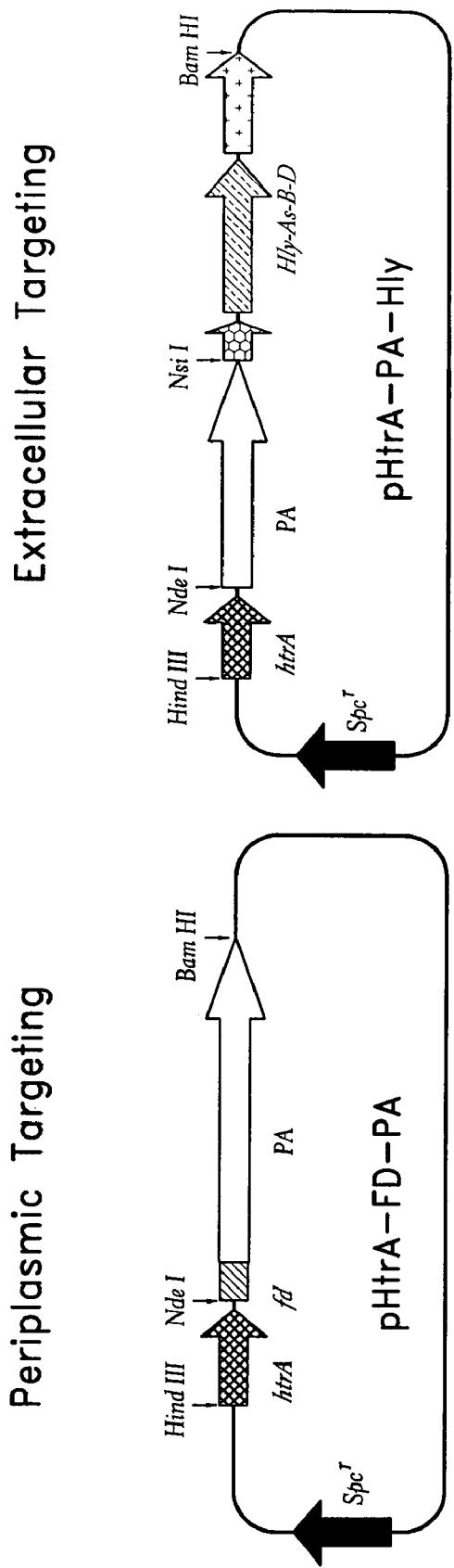

FIG. 14. Representative plasmids for periplasmic and extracellular secretion.

Figure 15:
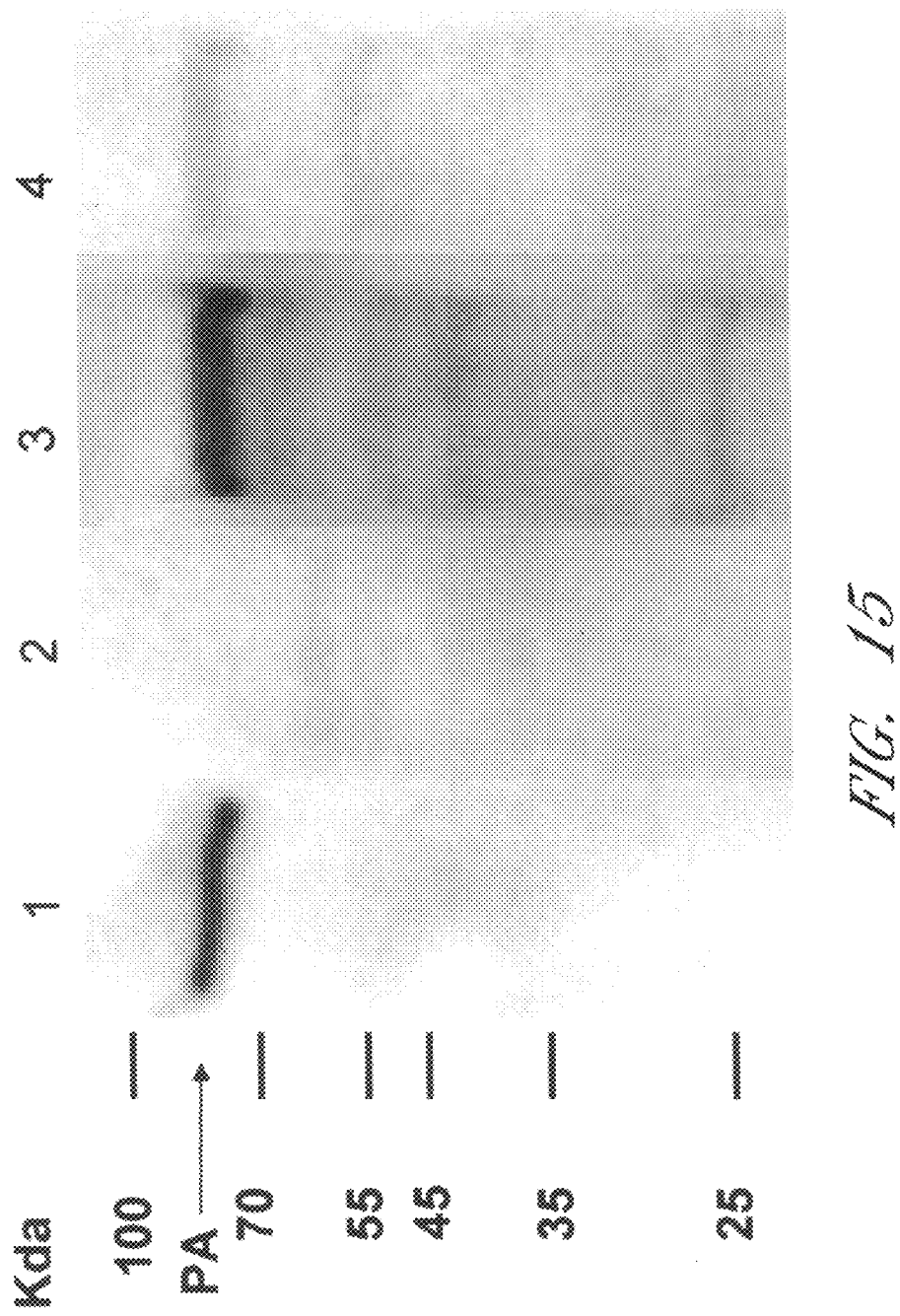

FIG. 15. Representative immunoblot of PA expression in *S. Typhi* Ty21a. Lanes (1) Purified PA 150 ng/land, (2) pGB-2 plasmid control ($10^8$ cfu), (3) phtrA-PAcm ($10^8$ cfu), (4) phtrA-PAwt ($10^8$ cfu).

Figure 16:
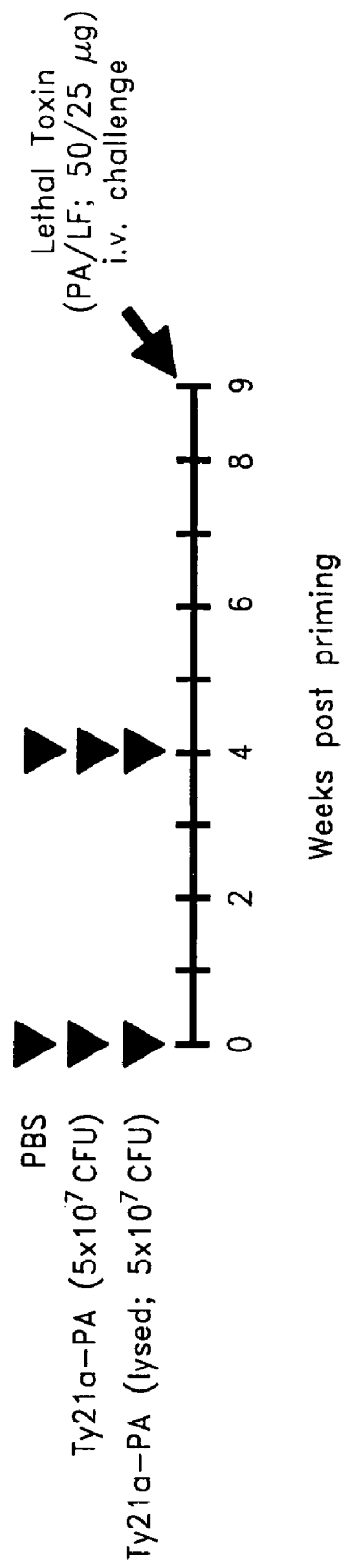

FIG. 16. Dosing and challenge schedule for Ty21a mice.

Figure 17:
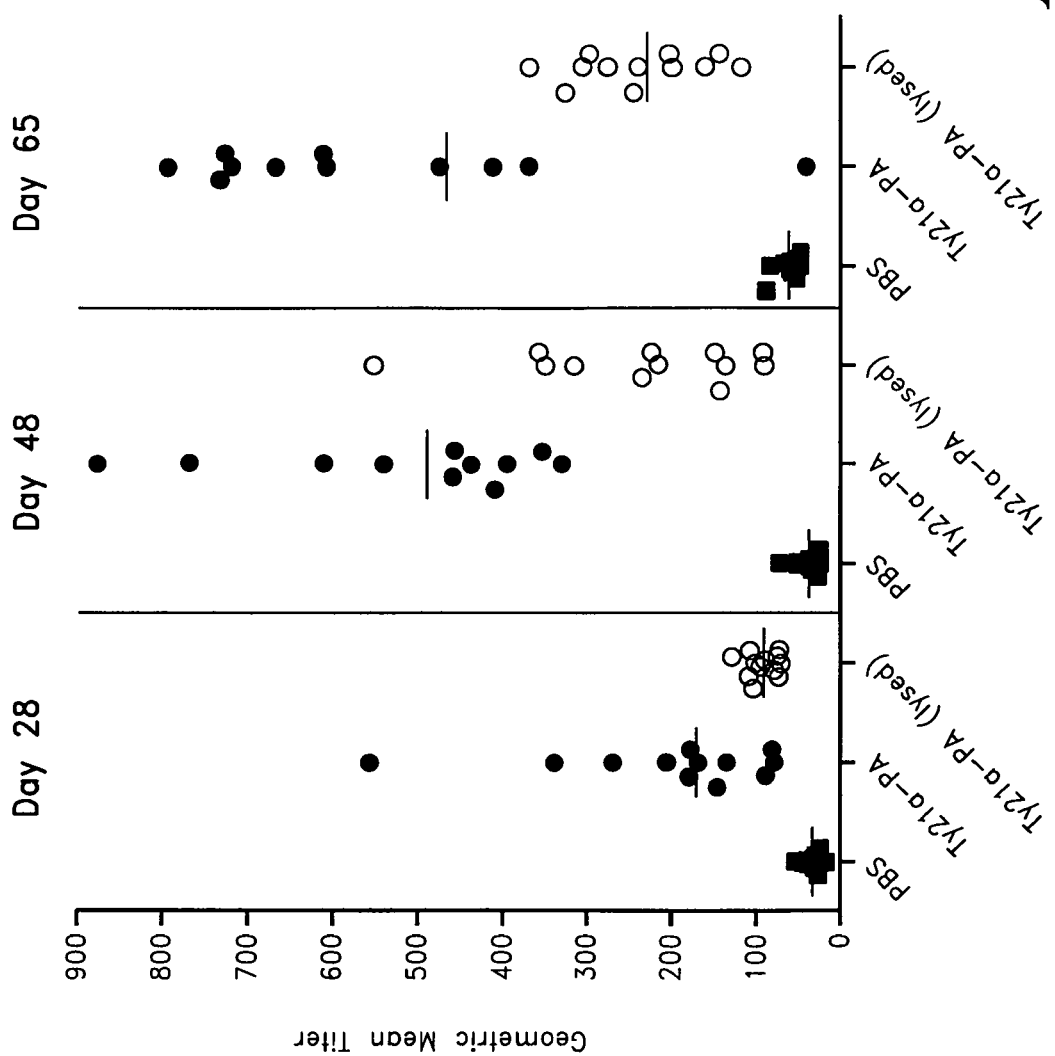

FIG. 17. Anti-PA geometric mean titer (GMT) in Ty21a-PAwt immunized mice.

Figure 18:
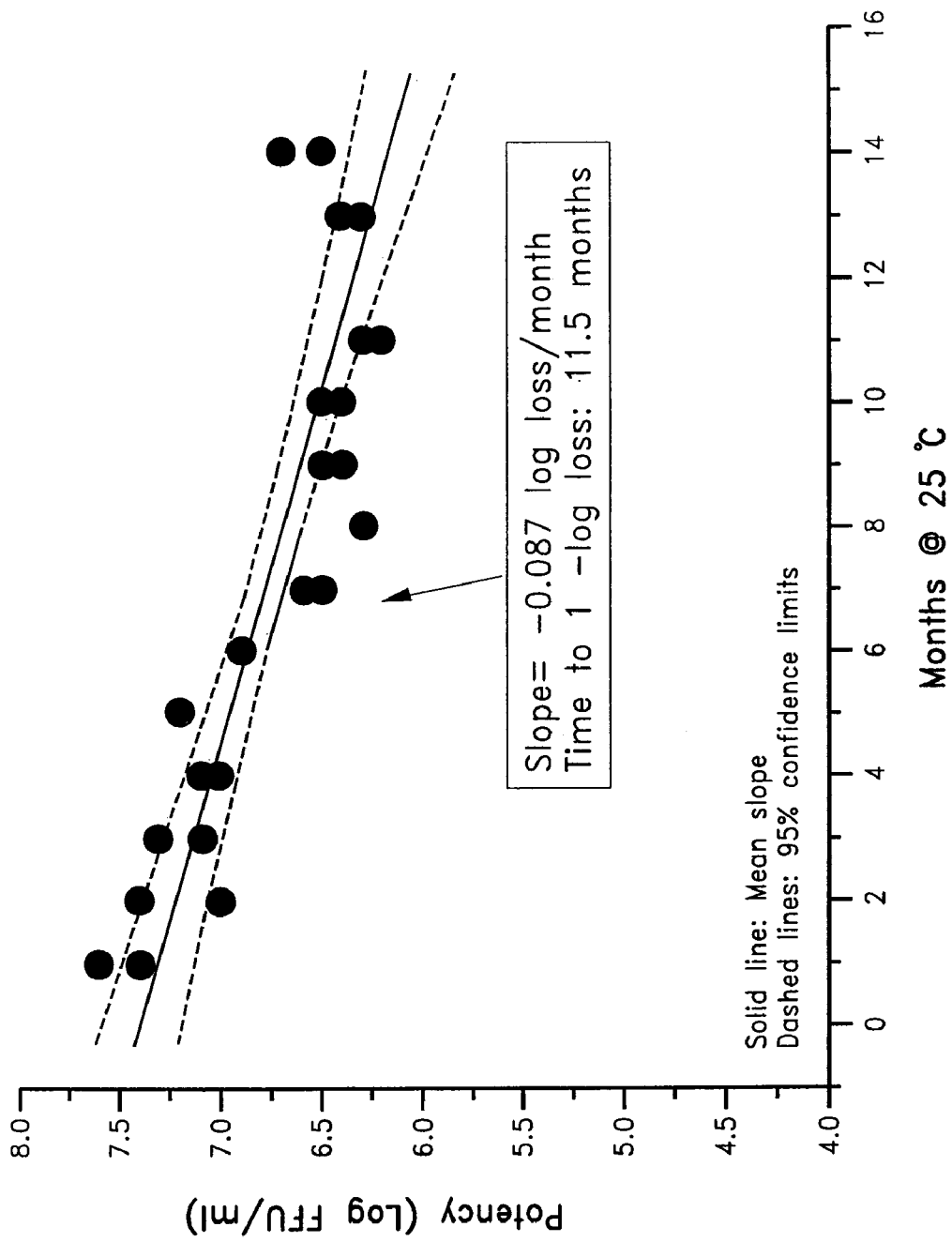

FIG. 18. Real time stability of B/Harbin live attenuated influenza virus vaccine formulated and spray dried. Shown are the mean slope and 95% confidence intervals.

Figure 19A:
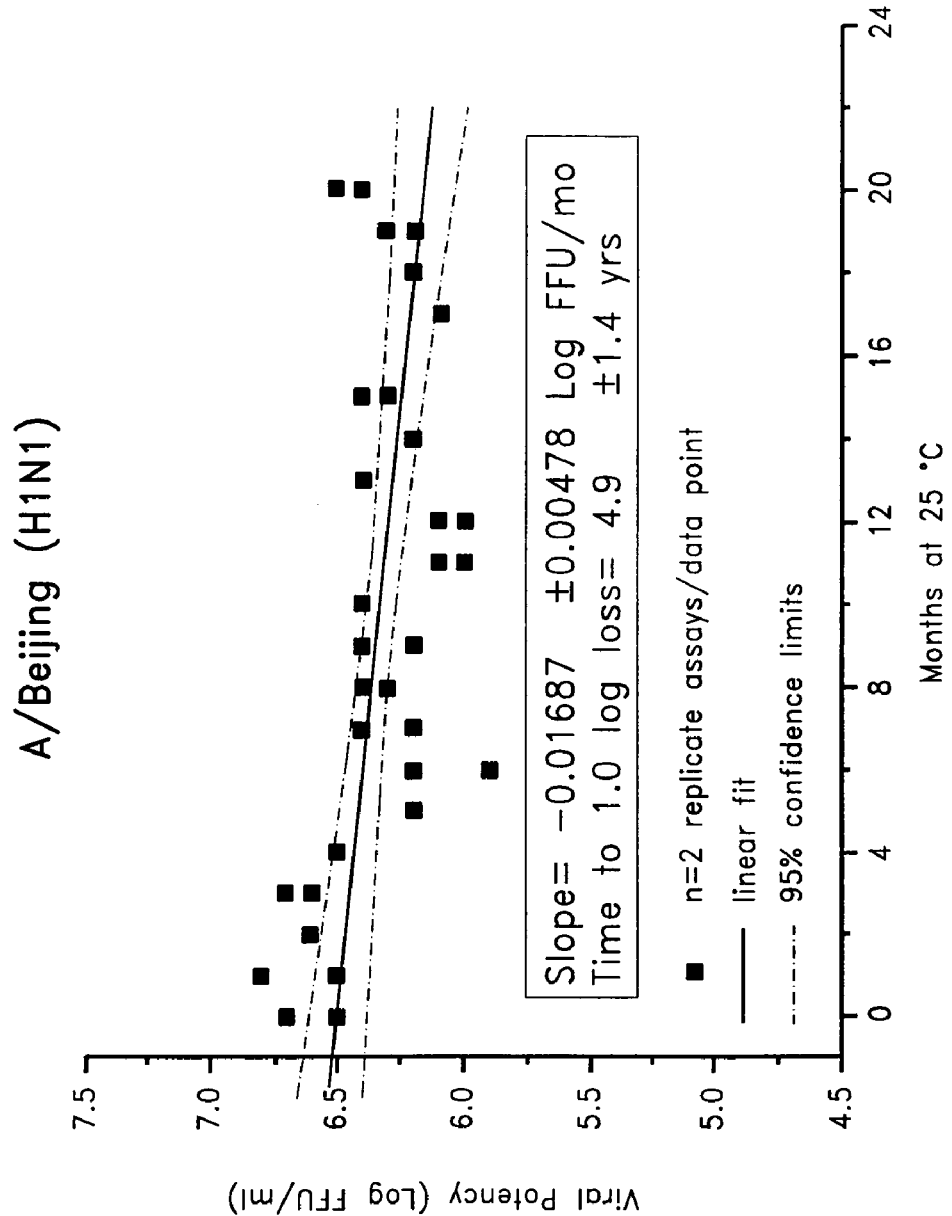
Figure 19B:
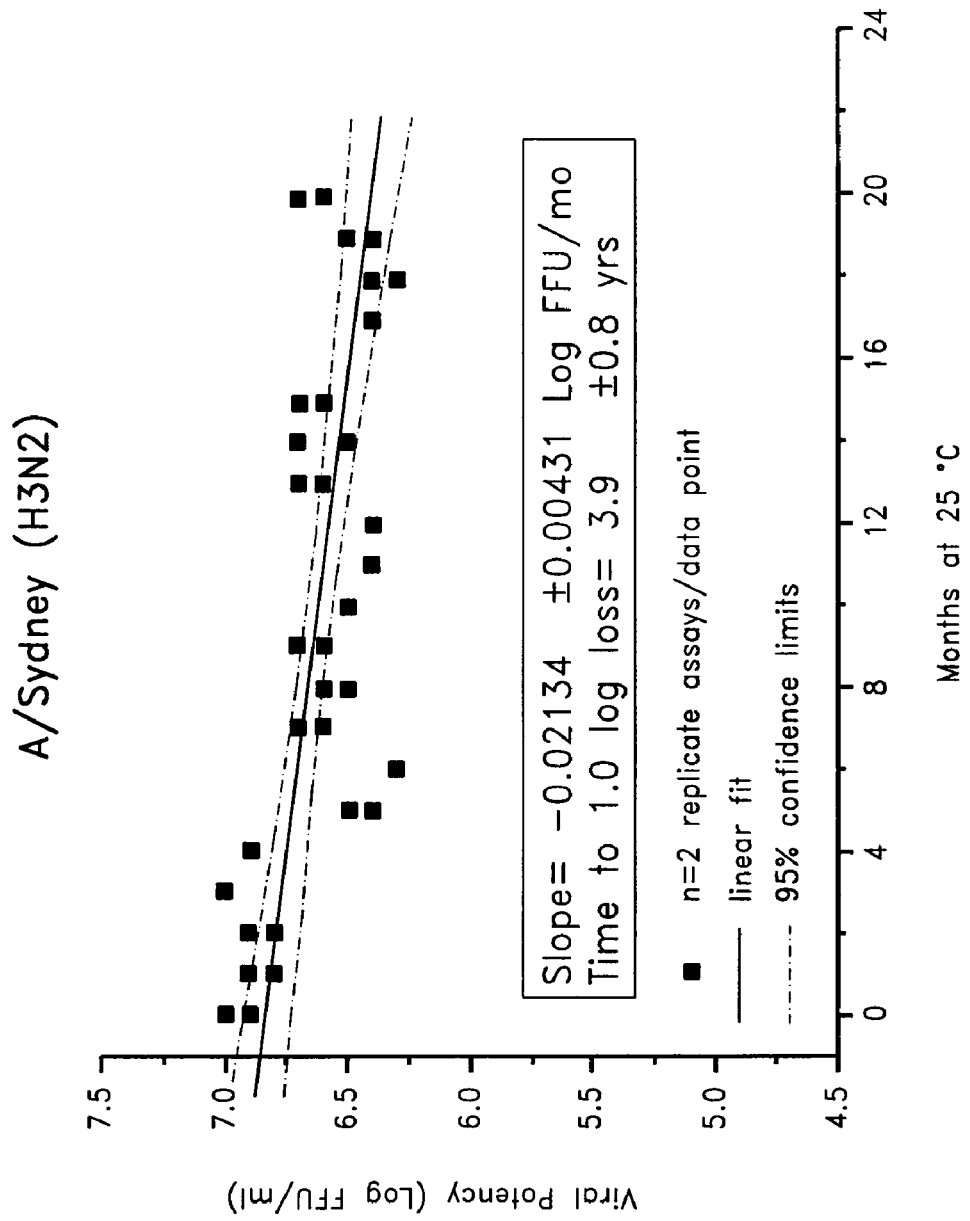
Figure 19C:
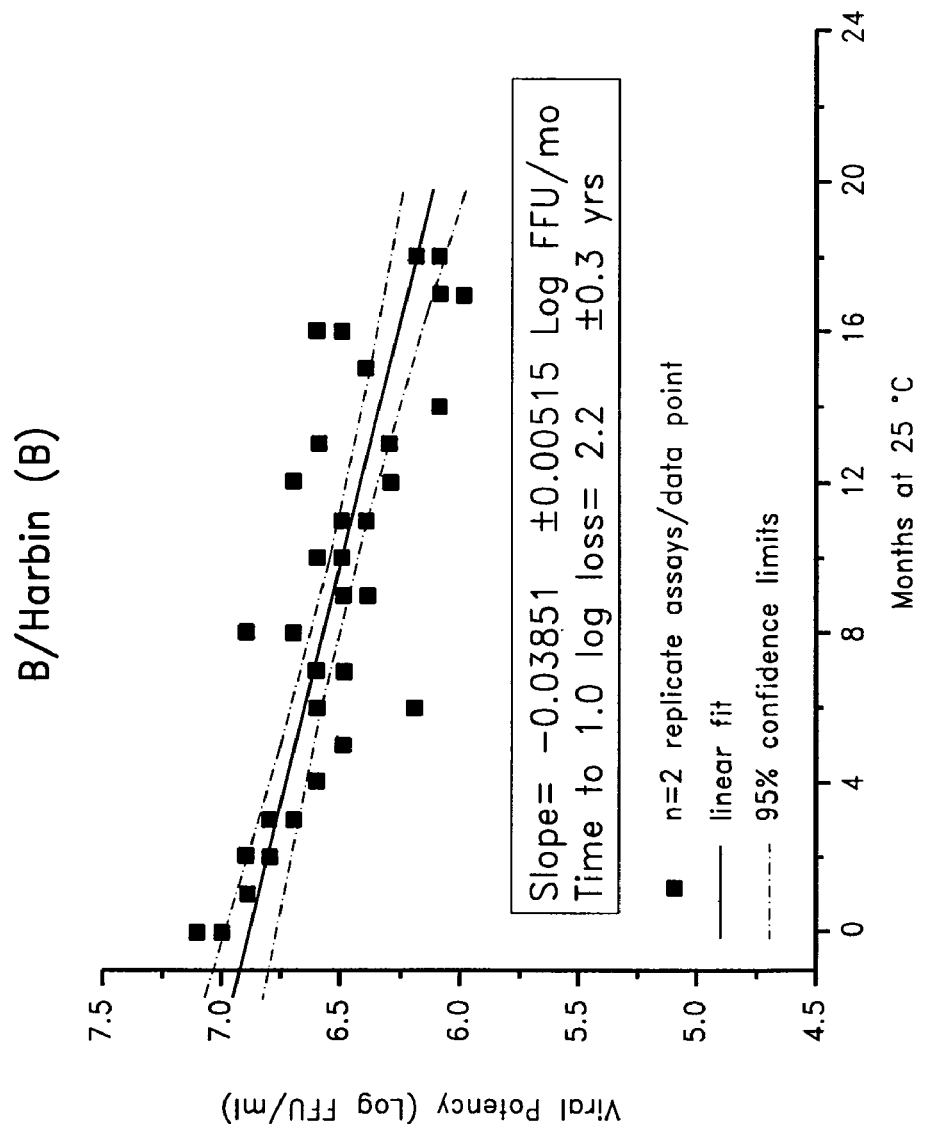

FIG. 19 A-C. Real time stability of live attenuated influenza virus formulated and freeze dry foamed. Shown are the mean slope and 95% confidence interval for three monovalent influenza strains (A) A/Beijing (H1N1 strain), (B) A/Sydney (H3N2 strain), and (C) B/Harbin (B strain).

FIG. 20 A-B. Production of stable dry powder particles with optimal size range for nasal deposition. (A) Placebo formulations were spray dried under different mass ratios of atomizer gas to liquid feed and then subjected to laser diffraction particle size analysis. (B) Foam dried formulation was mechanically recovered with a spatula then subjected to mechanical impact milling using a pin mill to produce fine dry powders.

Figures 21, 22:
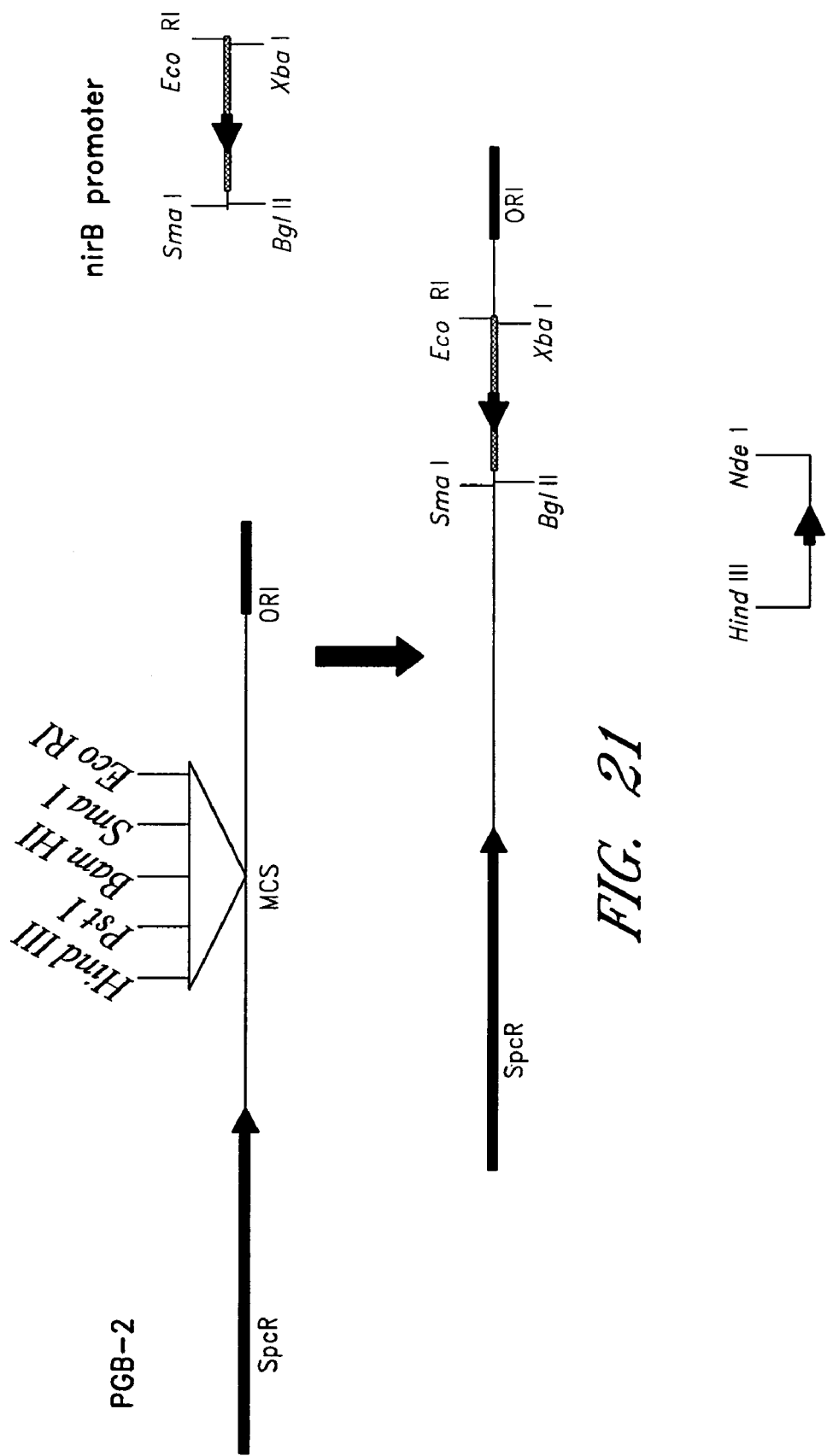

FIG. 21. pGB-2/nirBp.

FIG. 22. htrA promoter.

FIG. 23 A-B. DNA sequences coding for *B. anthracis* Protective Antigen.

Figure 24:
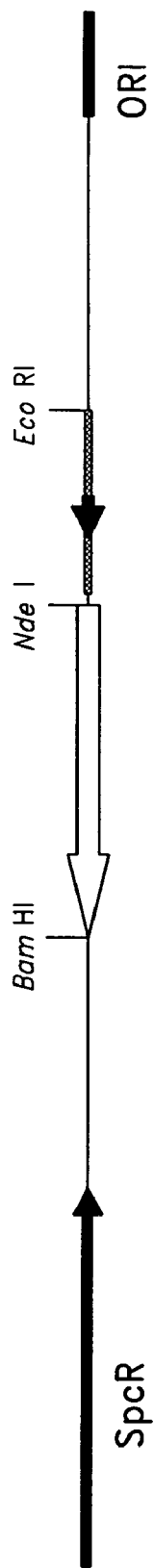

FIG. 24. pnirB-PA (PAcm).

Figure 25:
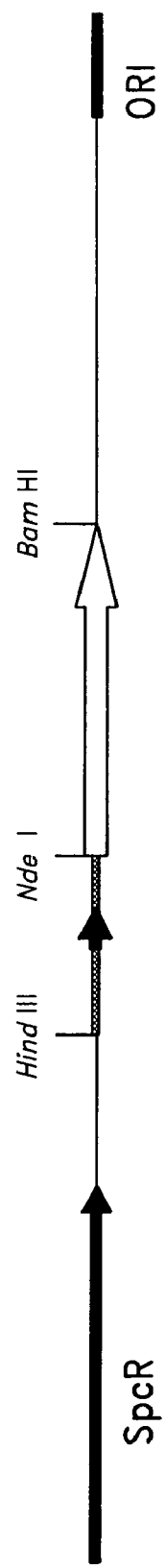

FIG. 25. phtrA-PA (PAcm).

Figure 26:
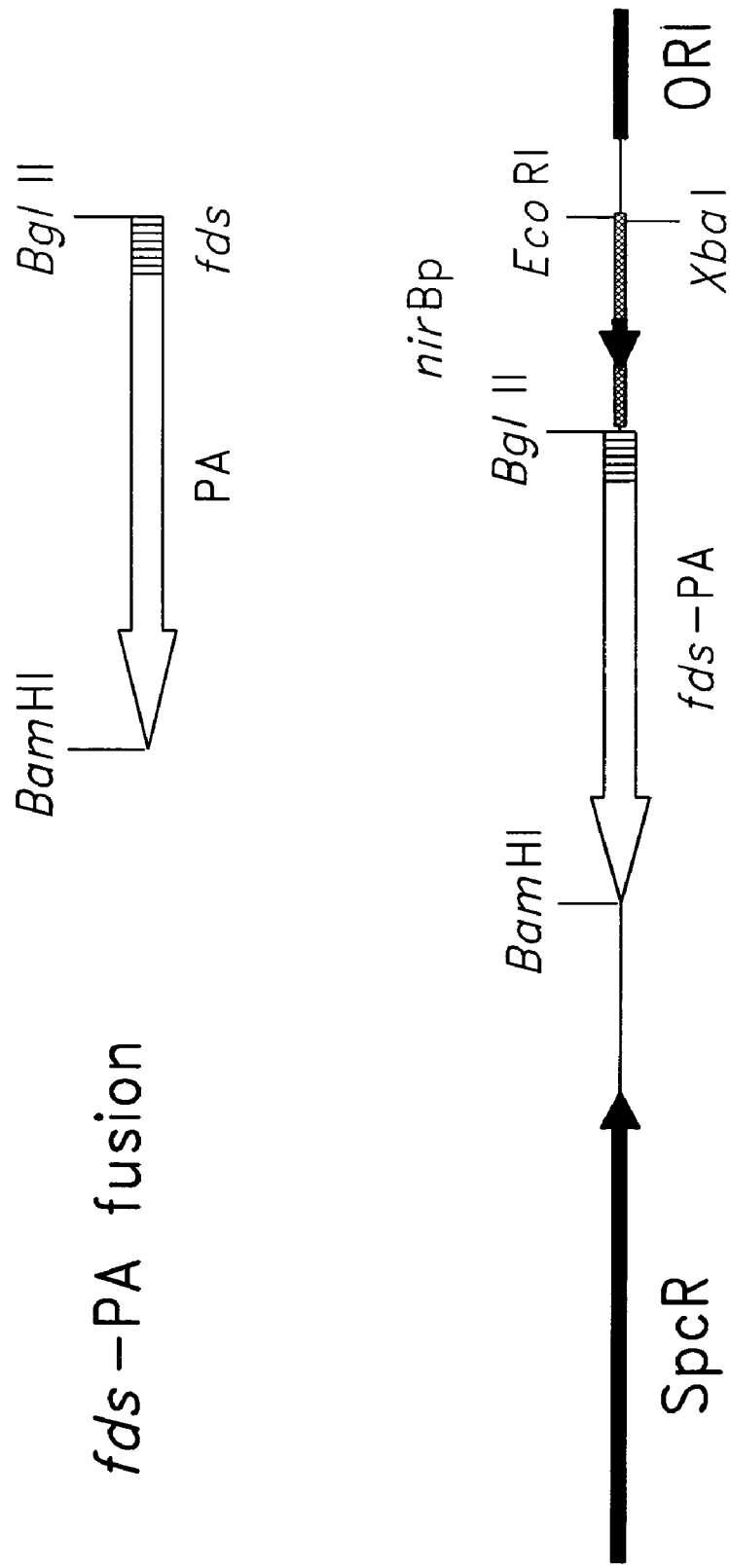

FIG. 26. pnirB-fds-PA.

Figure 27:
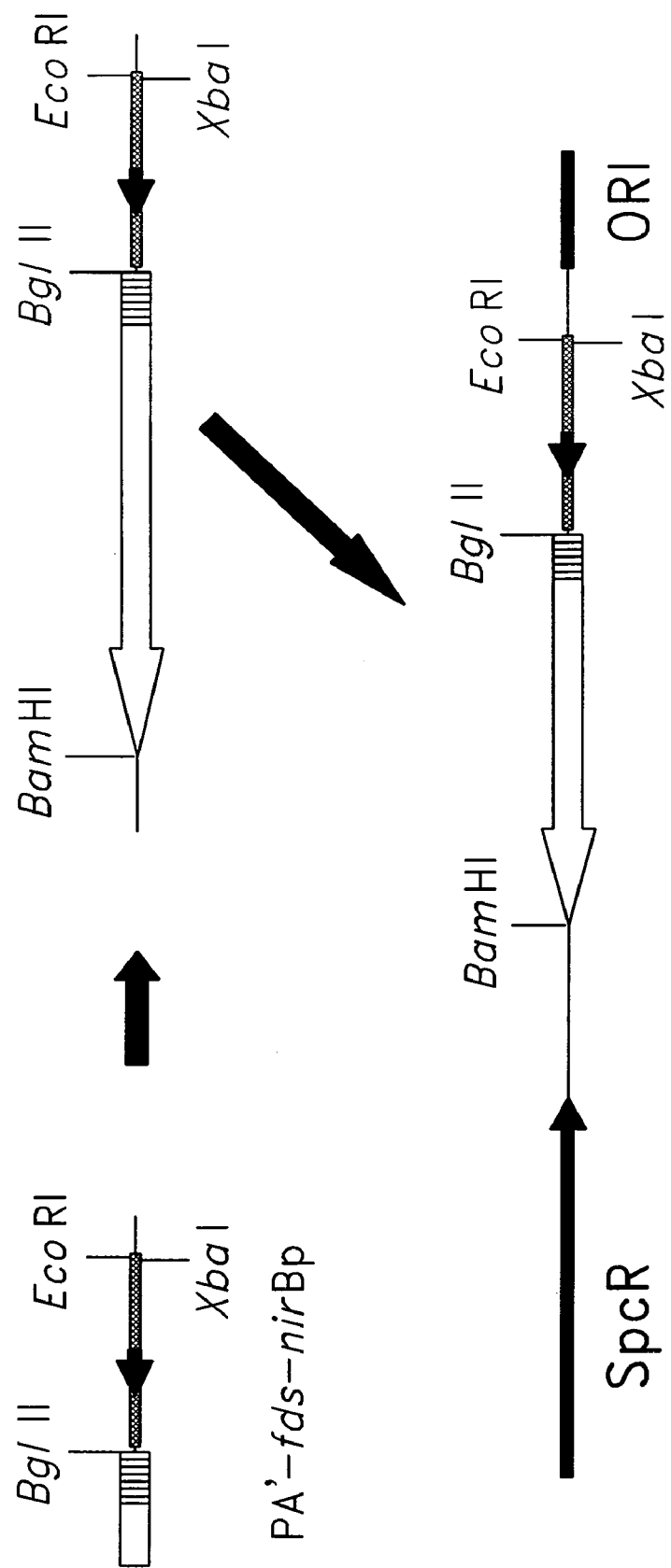

FIG. 27. pnirB-fds-PAcm.

Figure 28:
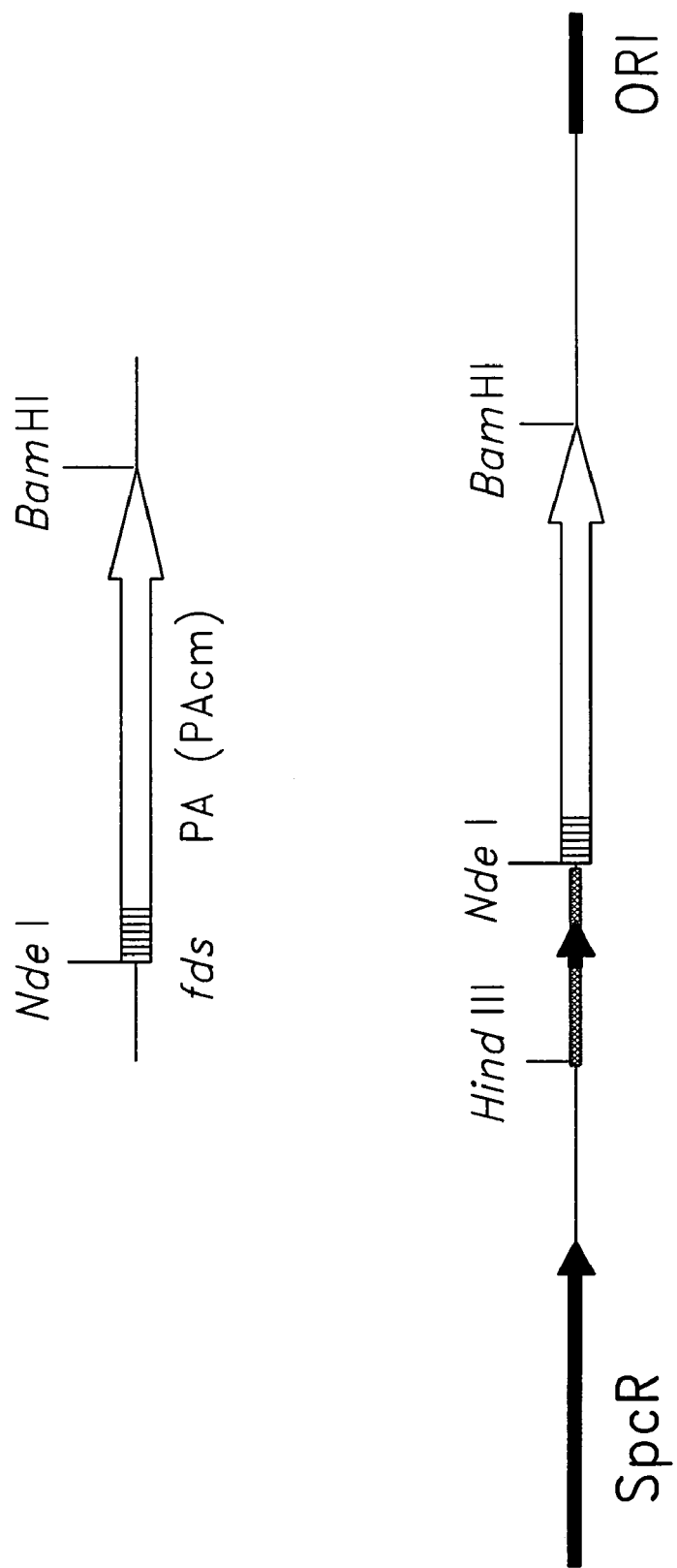

FIG. 28. phtrA-fds-PAcm.

Figure 29A:
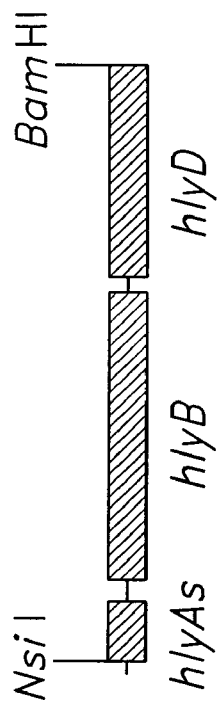
Figure 29B:
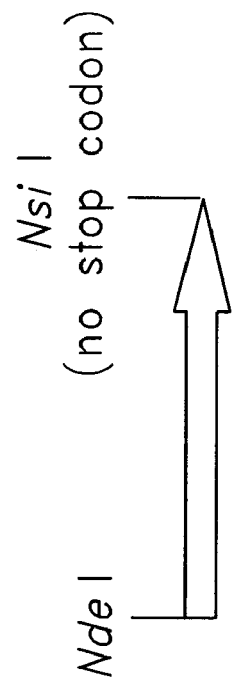

FIG. 29 A-C. Construction of phtrA-PA-Hly. (A) HlyAs-BD cassette, (B) PA without stop codon, (C) phtrA-PA-Hly.

Figure 30A:
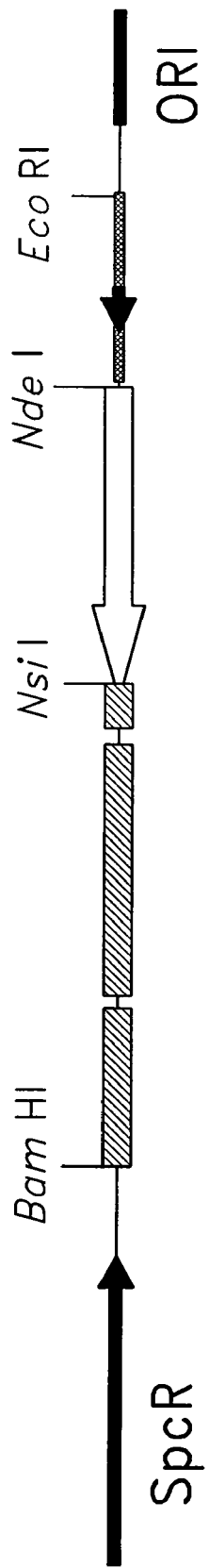
Figure 30B:
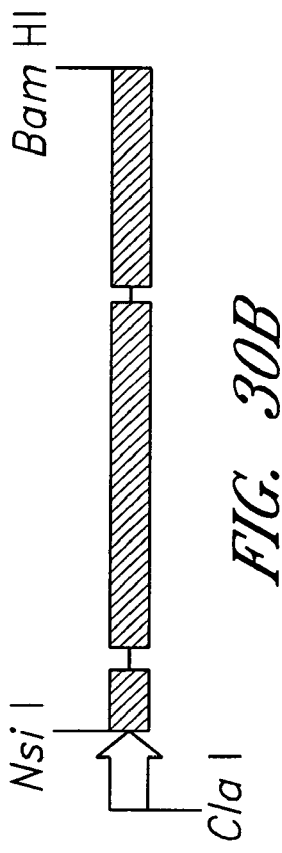
Figure 30C:
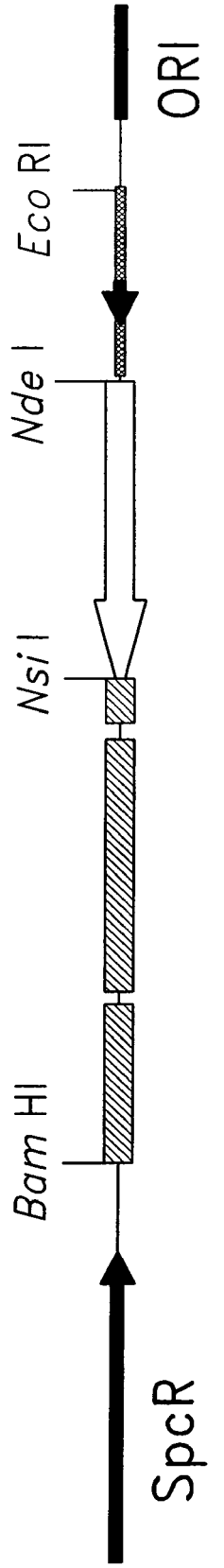

FIG. 30 A-C. Construction of pnirB-PA-Hly. (A) pnirB-PA-Hly, (B) PAcm-HlyAs fusion fragment, (C) pnirB-PAcm-Hly.

DETAILED DESCRIPTION OF THE PREFERRED EMBODIMENT

Part I A

DNA Promoters

*Salmonella enterica* serovar *Typhimurium* definitive phage type 104 (DT104) strains are emerging foodborne pathogens in several countries worldwide (Evans S. and Davies R. 1996 *Vet Rec* 139: 557-558; Hollingsworth J. and Kaplan B. 1997 *J Am Vet Med Assoc* 210:1712 & 1716; Gosek G. et al. 1996 *MMWR* 46:308-310). DT104 strains typically are multiply resistant to many commonly used antibiotics and have been isolated from poultry, swine, cattle, and other domestic and wild animals. First detected in the U.K. in 1984, this epidemic DT104 lineage has increased from 9% of total nontyphoid *Salmonella* isolates in 1990 to 33% of all isolates in 1996 in the U.S. (Besser T. E. et al. 1997 *Vet Res* 140:75). The mortality rate for clinically affected cattle with antibiotic resistant DT104 strains has been reported to be 40-60% in some outbreaks in the U.K. (Wall P. G. et al. 1995 *Vet Res* 136:591-592). In fact, the case-fatality rate in humans may be higher than with other nontyphoid *Salmonella* strains. In a study of. 83 DT104 cases in the U.K., 41% of patients were hospitalized and 3% died. In contrast, the case-fatality rate for other nontyphoid *Salmonella* infections is typically <0.1%.

There are presently no unique methods available for the control of DT104 strains in humans or animals, primarily because little is understood about the rapid emergence of these strains in nature. Hence, there is a need to study the molecular pathogenesis of DT104 strains in order to define unique virulence attributes which can be used to develop biomarkers for rapid identification of this pathogen. The current approach is part of a larger overall study aimed at using promoter-trap vectors and DNA microarray technology to search for genes that are uniquely expressed inside host cells by DT104 strains.

Materials and Methods

Bacterial Strains and Growth Conditions. The bacterial strains used in this study are listed in Table 1 and include the multiply restriction-minus, modification plus *Salmonella Typhimurium* strain LB5000, and *S. Typhimurium* DT104 strains (BT9 isolate from a clinical preschool outbreak in Hawaii, USA, source #H2662 Ms. Peggy Hayes, CDC; BT-19 isolate from cattle feces, source #30 Dr. Tom Humphrey, PHLS). Unless otherwise indicated, all bacterial strains were routinely grown in LB broth or agar containing 1% NaCl. Ampicillin and chloramphenicol were used at a final concentration of 100 µg/ml. Brain heart infusion broth was used for bacterial growth prior to invasion studies.

INT 407 Cell Invasion Studies. Young 1 day old monolayers of INT407 human epithelial cells were used in all experiments and were routinely maintained in minimum essential medium supplemented with 2 mM glutamine, nonessential amino acids, penicillin/streptomycin, and 10% fetal bovine serum (Life Technologies, Grand Island, N.Y.) in a 5% $CO_2$ atmosphere at 37° C. For invasion studies, cultures of bacteria were grown without aeration at 37° C. overnight in Brain-Heart Infusion medium supplemented with 0.3M NaCl. The monolayer cells were infected with mid-log phase bacteria at MOI's of 100-300. Following an invasion period of 1-3 hours at 37° C., the cells were washed with D-PBS. Remaining extracellular bacteria were killed by incubation for 1 hr in 100 µg/ml gentamicin added to the culture medium. To select for intracellular induction of cloned promoter fragments in the promoter-trap pCG101 vector, 100 µg/ml of chloramphenicol was added to the monolayer for 16 hours. Infected monolayers were lysed with 0.5% Triton X-100 over 15 minutes to release intracellular bacteria.

J774 Cell Invasion Studies. Young 1 day old monolayers of J774.A3 murine macrophage cells were used in all experiments and were routinely maintained in D-MEM supplemented with nonessential amino acids, penicillin/streptomycin, and 10% fetal bovine serum (Life Technologies, NY) in a 5% $CO_2$ atmosphere at 37° C. For invasion studies, bacterial cultures were grown without aeration at 37° C. overnight in BHI medium supplemented with 0.3M NaCl. The monolayer cells were infected with mid-log phase bacteria at ~100 MOI. Following a 2 hour invasion period at 37° C., the cells were washed with D-PBS. Remaining extracellular bacteria were killed by incubation with 100 µg/ml gentamicin added to the culture medium. The intracellular bacteria from infected cells were released by host cell lysis with 0.5% Triton X-100 in D-PBS.

Florescence-Activated-Cell-Sorting (FACS) Analyses. FACS analysis was performed using a FACSVantage SE flow cytometer/cell sorter (Becton Dickinson). For analysis of infected cells, cells were removed from monolayers by trypsin/EDTA treatment, washed by centrifugation, resuspended and filtered through fine mesh into 12×75 mm tubes. Forward light scatter (FCS) versus side scatter (SSC) gating was used to identify the viable cell population. Cells containing GFP-expressing bacteria were identified by log-amplified green fluorescence. Analysis of GFP-expressing bacteria was accomplished by lysing infected cells with Triton X-100 (0.1%), and filtration of cellular debris. For bacterial analysis, the threshold parameter was SSC. Sorting of GFP containing infected cells or bacteria was accomplished by creating a sorting gate based on green fluorescence intensity that was above the autofluorescence background.

Plasmids and Recombinant DNA Methods. Plasmids were isolated with QIAprep Spin Miniprep kits (Qiagen, Inc.). DNA fragments from agarose gels were isolated using QIAuick Gel Extraction kits (Qiagen, Inc.). All restriction and DNA modifying enzymes were procured from New England BioLabs.

Insert sizes from selected plasmid clones were determined by PCR amplification using primers on plus (5'-CGT ATT ACC GCC TTT GAG TG-3') (SEQ ID NO: 17) and minus (5'-GGG ACA ACT CCA GTG AAA AG-3') (SEQ ID NO: 18) strands, which flank the inserts cloned at the BamHI site in the promoter-trap plasmid expression vector, pCG101. All PCR reactions were carried out using the "hot-start" method (15 min at 95° C., 25 sec at 94° C., and 25 sec at 52° C. and 30 sec at 72° C. for a total of 35 cycles; Qiagen HotStart Taq MasterMix kit). The final elongation was done at 72° C. for 5 min. The amplified PCR inserts were size-analyzed by agarose gel electrophoresis using DNA molecular weight markers.

DNA Sequencing. DNA sequencing was performed with Ready Reactions DyeDeoxy Terminator cycle sequencing kits (Applied Biosystems) and an ABI model 373A automated sequencer. Sequences were assembled and analyzed by using the Vector NTI suite 6.0 software (Informax, Inc.). DNA homology searches were performed by using the Basic Local Alignment Search Tool (BLAST) of the National Center for Biotechnology Information. Bacterial putative promoter searches were conducted according to the Neural Network Promoter Prediction Model (fruitfly.org/seq_tools/promoter.html).

Results

Figure 1:
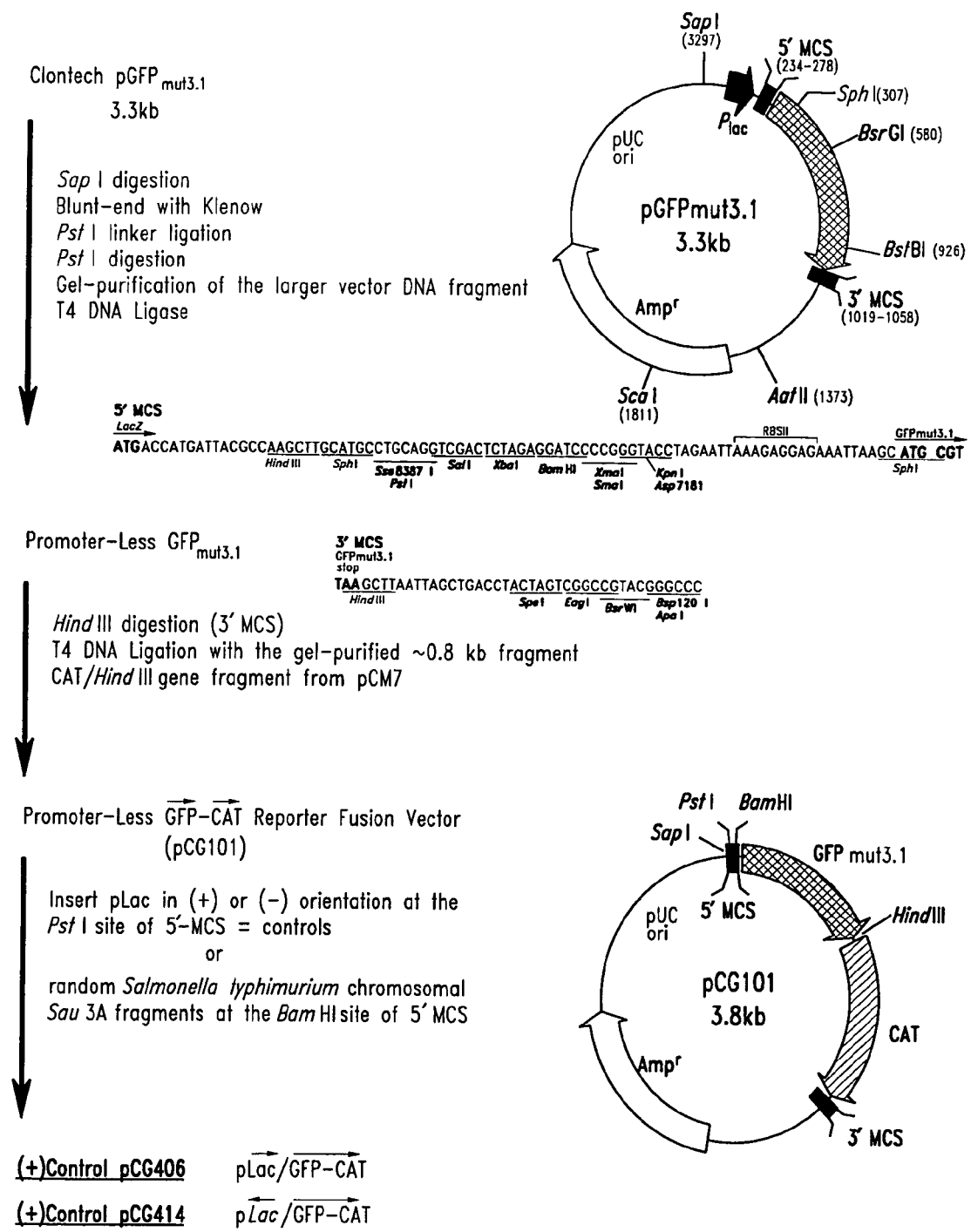
FIG. 1. Construction of promoter-trap GFP-CAT reporter plasmid vector. Promoterless GFPmut3.1 sequence.

Construction of the Promoter-trap Bacterial Expression Vector and DT104 Genomic Fragment Library. The promoter-trap plasmid was constructed from the 3.3 kb pGFPmut3.1 plasmid. pGFPmut$_{3.1}$ contains a pUC origin of replication, an ampicillin resistance gene (Ap$^r$), and the reporter gene GFP linked to P$_{lac}$ and a multiple cloning site (MCS). As shown in FIG. 1, the unique Sap1 site was converted, via linker ligation, to a Pst1 site. Pst1 digestion of the resulting plasmid effected the deletion of Plac, and created a promoter-less pGFPmut3.1. A chloramphenicol acetyltransferase (CAT) gene obtained from pCM7 on a HindIII fragment was ligated to the HindIII site at the C-terminal end of GFP to create pCG101. This Ap$^r$ "promoter-trap" bacterial expression plasmid pCG101 is a pUC replicon that contains a MCS in front of fused GFP and CAT reporter genes and was used to select for the insertion of random promoter fragments from the S. Typhimurium DT104 genome, as described below (see FIG. 1).

S. Typhimurium DT104 isolate BDT-9 genomic DNA was isolated, partially digested with Sau3a, and size-fractionated on an agarose gel to obtain 0.4-1.6 kb fragments. These selected fragments were randomly cloned into the BamH1-digested, pCG101 in front of the fused reporter genes (FIG. 2). Resulting plasmid recombinants were electroporated into E. coli DH5α and selected on media containing ampicillin. Population-isolated plasmids from DH5α were passed through S. Typhimurium strain LB5000 for DNA modification, before final electroporation into S. Typhimurium DT104 strain BDT-19. Positive and negative experimental control promoter plasmids contained the Plac sequence on a Pst1 fragment in the correct or opposite orientation, respectively, at the Pst1 site in front of the GFP gene (see FIG. 1). The resultant library of promoter-fragment clones consisted of ~40,000 recombinant plasmids and was used to enrich for intracellularly-activated promoters as described below.

Selection for Promoter-Fragments that are Activated Intracellularly in INT407 Epithelial Cells. A unique double-selection strategy was employed to enrich for intracellularly activated, cloned promoter DNA sequences (FIG. 3). The DT104 bacteria bearing the entire genomic fragment library in pCG101 were used to infect 1 day old INT407 cells at an MOI of ~200. Following a 1-3 hr. invasion period, remaining extracellular bacteria were killed in the presence of 100 µg/ml gentamicin over a 1 hr period. To select for intracellular induction of cloned promoter fragments in the promoter-trap pCG101 vector, 100 µg/ml of chloramphenicol was added to the monolayer for 16 hrs. Intracellularly-induced, surviving Cm$^r$ clones were additionally enriched for GFP expression by FACS analysis. FACS control studies using uninfected cells and pLac insert controls allowed for the establishment of fluorescence gate limits to detect GFP expression from promoter clones (FIG. 4). To eliminate the selection of constitutive promoters, the selected GFP+, Cm$^r$ isolates were grown in nutrient medium and FACS-selected for only GFP-bacteria. This double-selection strategy was repeated a total of three times to obtain highly enriched, intracellularly-activated promoters from the DT104 promoter fragment library (FIG. 5).

Analyses of Selected Promoter Fragments. From the enriched DT104 genomic promoter library, we randomly picked 150 clones following the 3 cycles of double-selection for intracellular expression. Each of these clones were used to infect INT407 cells, and intracellular fluorescence was quantitated by FACS. Kinetic analyses of fluorescence upregulation during INT407 cell infection showed a range of induction from ~10- to >100-fold over 3 hours (see FIG. 6).

DNA sequence analyses of a representative number of clones revealed that there are only 5 different promoter fragments represented in the 150 randomly selected recombinants (see Table 2 and FIG. 8, SEQ ID NOs: 1-5). These five unique intracellularly-expressed promoters exist on fragments ranging from ~0.5 to 1.5 kb and which include or are adjacent to the following identified S. Typhimurium genes: (a) sixA—a phosphohistidine phosphatase; (b) phsA, a thioglycolate reductase precursor; and (C) pgtE, a phosphoglycerate transport-associated outer membrane protease E precursor; (D), marC, multiple antibiotic resistance transporter; and (e) fabD, which is involved in acyl carrier protein synthesis.

Selection of Promoter-Fragments that are Activated Intracellularly in J774 Macrophage Cells. The above double selection strategy for promoter expression in INT407 cells utilizing chloramphenicol required 16 hrs treatment to kill Cm$^S$ bacteria. In order to detect promoters that are upregulated in a shorter period of time, a single FACS selection strategy was used after 3 hrs in J774 cells (FIG. 7). Four cycles of selection for GFP-expression under intracellular inducing conditions and GFP-nonexpression under broth growth conditions was used to select a final library of 52 clones for plasmid insert size analysis. Of these 52 inserts, only two different inserts sizes were found and these are described in Table 3 and FIG. 8 (SEQ ID NOs: 6-8).

SUMMARY

A promoter-trap plasmid vector has been constructed which contains tandem GFP and CAT reporter genes. This vector was utilized to develop a library of small DNA fragments representing the genome of S. Typhimurium DT104. Cloned promoter fragments were inserted into a recipient DT104 strain which was used to infect INT407 human cells. A stringent double-selection strategy was employed to select for intracellular reporter gene expression. Analysis of a representative set of selected promoter fragments revealed five unique inserts that exhibit a range of inducibility from 5- to >100-fold in eukaryotic cells. This same library of DT104 strain promoter fragments was screened in J774 macrophage cells for inserts that are upregulated intracellularly within 2 hours and two unique fragment inserts of 0.8 and 1.5 kb were detected. These 7 promoter regions have utility for use in live vector bacterial vaccines or in other production systems for the controlled expression of foreign antigens. These studies are part of a larger effort to search for unique virulence/growth activities of these rapidly emerging DT104 pathogenic Salmonellae.

TABLE 1

Bacterial Strains and Plasmids

| | Description | Source |
|---|---|---|
| Bacteria | | |
| Escherichia coli DH5α | | Clontech |
| Salmonella enterica serovar Typhimurium | Strain LB5000 hsdR−, hsdM+ | LESTD$^a$ collection |
| | DT104 isolate BT9, ampicillin resistant | CDC$^b$ |
| | DT104 isolate BT19, ampicillin-sensitive | PHLS$^c$ |

TABLE 1-continued

Bacterial Strains and Plasmids

| | Description | Source |
|---|---|---|
| Plasmids | | |
| pCM7 | Source of CAT gene | Pharmacia |
| pGFP mut$_{3.1}$ | Spc$^R$ | Clontech |
| pCG101 | Promoter-trap vector fused with GFP/CAT reporter genes | This study |
| pCG106 | pCG101 with plac transcriptionally linked to reporter genes | This study |
| pCG114 | pCG101 with plac in reverse linkage to reporter genes | This study |
| pCG301-503 | Individual inserts within pCG101 which were selected for intracellular expression of GFP-CAT reporter genes | This study |

$^a$LESTD = Laboratory of Enteric and Sexually Transmitted Diseases
$^b$CDC = Centers for Disease Control and Prevention
$^c$PHLS = Public Health Laboratory Service

TABLE 2

Characterization of promoter fragment inserts detected in INT407 cells

| Plasmid | Insert length (bp) | Avg. % G + C | # putative promoters |
|---|---|---|---|
| pCG301 | 689 | 48.33 | 4 |
| pCG316 | 971 | 51.08 | 7 |
| pCG322 | 1468 | 49.32 | 4 |
| pCG433 | 837 | 50.42 | 4 |
| pCG307 | 577 | 54.25 | 0 |

TABLE 3

Characterization of promoter fragment inserts detected in J774 macrophage cells.

| Plasmid | Insert Length (bp) | Avg. % G + C | # putative promoters |
|---|---|---|---|
| pCG501* | 1843 (979 + 864) | 54.48 | 10 |
| pCG502 | 689 | 53.96 | 0 |

*Sequencing revealed that two noncontiguous segments of the chromosome were cloned into pCG501 and incomplete sequencing resulted in two non-overlapping fragments of 979 and 864 bp Part I B Expression of Recombinant Proteins in Attenuated Bacteria This invention relates to attenuated bacteria capable of expressing a heterologous protein, to their preparation and to vaccines containing them.

Virulent strains of *Salmonella* can be attenuated by introducing specific mutations into genes required for survival and growth in vivo. Attenuated variants which establish self limiting, clinically insignificant infections can be considered as potential live oral vaccines against *Salmonella* infections. Ty21a is an attenuated variant of *Salmonella Typhi*, which harbors mutations in galE and other unknown attenuating lesions, and is licensed for use in many countries as a live oral typhoid vaccine.

More recently genetically defined *Salmonella* strains harboring individual specific mutants in different genes have been tested as experimental oral vaccines in several target species. For example, *Salmonella* aro mutants, which have an auxotrophic requirement for several aromatic compounds, have been shown to be effective oral vaccines in mice, sheep, cattle, chickens and more recently they have been shown to be attenuated and immunogenic in volunteers. *Salmonella* cya crp double mutants are also effective oral vaccines.

As well as being vaccines in their own right against salmonellosis, attenuated Salmonellae can be considered as carriers of heterologous antigens to the immune oral system. This is because Salmonellae can be delivered via the oral route and are potent immunogens being able to stimulate systemic and local cellular and antibody responses. Heterologous antigens from bacteria, viruses and parasites can be delivered to the host using *Salmonella* vaccines.

One potentially serious drawback in using these live vaccines for antigen delivery relates to problems with the stability of the foreign antigen expression in vivo. Unregulated expression of high levels of a foreign protein in bacteria from multiple copy plasmids usually results in rapid loss of the plasmid or expressed gene from the cells. This problem can be controlled in fermenters by using inducible promoter systems such as trp or lac to allow the controlled induction of gene expression when the appropriate biomass has been achieved. Obviously these promoters can not be induced by exogenously applied inducers such as PP or IPTG when bacteria are growing in host tissues during the self-limited growth following vaccination.

In vivo plasmid instability during vaccination with live bacterial vectors has in fact been reported by many workers (Maskell et al. 1987 *Microb Path* 2:295-305; Nakayama et al. *Biotechnology* 1988 6:693-697; Tire et al. 1990 *Immunology* 70:540-546). A number of approaches have been taken to overcome the problem including the use of integration systems for expression of the heterologous antigen from the bacterial chromosome (Hone et al. 1988 *Microbiol Path* 5:407-418; Strugnell et al. 1990 *Gene* 88:57-63). However, this approach is only suitable for use with some antigens since expression levels are often quite low (Maskell et al. 1987 *Microb Path* 2:295-305). Nakayama et al described the use of linking an essential gene to the expression plasmid for stabilizing in vivo expression. Although this is a highly effective approach, it does not prevent the generation of plasmid free variants but simply ensures they do not survive. Further stable but constitutive high level expression of a foreign antigen in a *Salmonella* vaccine strain could slow down the growth rate and hence potentially affect the immunogenicity of the live vaccine.

According to the present invention, there is provided an attenuated bacterium which is capable of expressing a heterologous protein, the expression of the heterologous protein being under the control of a promoter whose activity is induced by anaerobic conditions.

Stable expression of the heterologous protein can be obtained in vivo. The attenuated bacterium can therefore be used as a vaccine. Any suitable bacterium may be employed, for example a Gram-negative bacterium. Some Gram-negative bacteria such as *Salmonella* invade and grow within eukaryotic cells and colonize mucosal surfaces.

The attenuated bacterium may therefore be selected from the genera *Salmonella, Bordetella, Vibrio, Haemophilus, Neisseria* and *Yersinia*. Alternatively, the attenuated bacterium may be an attenuated strain of Enterotoxigenic *Escherichia coli*. In particular the following species can be mentioned: *S. Typhi*, the cause of human typhoid; *S. Typhimurium*, the cause of salmonellosis in several animal species; *S. enteritidis*, a cause of food poisoning in humans; *S. choleraesuis*, a cause of salmonellosis in pigs; *Bordetella pertussis*—the cause of whooping cough; *Haemophilus influenzae*—a cause of meningitis; *Neisseria gonorrhoeae*—the cause of gonorrhoea; and *Yersinia*—a cause of food poisoning.

The heterologous antigen which an attenuated bacterium is capable of expressing may for example comprise an antigenic determinant of a pathogenic organism. The antigen may be derived from a virus, bacterium, fungus, yeast or parasite. The heterologous protein therefore typically comprises an antigenic sequence derived from a virus, bacterium, fungus, yeast or parasite. More especially, the antigenic sequence may be derived from a type of human immunodeficiency virus (HIV) such as HIV-1 or HIV-2, hepatitis A or B virus, human rhinovirus such as type 2 or type 14, herpes simplex virus, poliovirus type 2 or 3, foot-and-mouth disease virus, influenza virus, coxsackie virus, the cell surface antigen CD4 and *Chlamydia trachomatis*. The antigen may comprise the CD4 receptor binding site from HIV, for example from HIV-1 or -2. Other useful antigens include the protective antigen (PA) of *B. anthracis*, *E. coli* heat labile toxin B subunit (LT-B), *E. coli* K88 antigens, P.69 protein from *B. pertussis*, tetanus toxin fragment C and antigens of flukes, mycoplasma, roundworms, tapeworms, rabies virus and rotavirus.

By deletion and mutational analysis the part of the promoter which responds functionally solely to anaerobisis or host intracellular conditions can be isolated.

An attenuated bacterium according to the present invention may be prepared by transforming an attenuated bacterium with a DNA construct comprising a promoter whose activity is induced by anaerobic conditions, such as the promoter sequences identified in FIG. 8 and in SEQ ID NOs: 1-8 or functional fractions thereof. Any suitable transformation technique may be employed, such as electroporation. In this way, an attenuated bacterium capable of expressing a protein heterologous to the bacterium may be obtained. A culture of the attenuated bacterium may be grown under aerobic conditions. A sufficient amount of the bacterium is thus prepared for formulation as a vaccine, with minimal expression of the heterologous protein occurring.

The DNA construct is typically a replicable expression vector comprising a promoter selected from FIG. 8 and in SEQ ID NOs: 1-8, or functional fractions thereof operably linked to a DNA sequence encoding the heterologous protein. The promoter may be inserted in an expression vector, which already incorporates a gene encoding the heterologous protein, in place of the existing promoter controlling expression of the protein. The expression vector should of course be compatible with the attenuated bacterium into which the vector is to be inserted.

The expression vector is provided with appropriate transcriptional and translational control elements including, besides the promoter, a transcriptional termination site and translational start and stop codons. An appropriate ribosome binding site is provided. The vector typically comprises an origin of replication and, if desired, a selectable marker gene such as an antibiotic resistance gene. The vector may be a plasmid.

An attenuated bacterium of the invention can be used as a vaccine. The vaccine comprises a pharmaceutically acceptable carrier or diluent and, as active ingredient, the attenuated bacterium.

The vaccine is advantageously presented in a lyophilized form, for example in a capsular form, for oral administration to a patient. Such capsules may be provided with an enteric coating comprising, for example, Eudragate "S", Eudragate "L", Cellulose acetate, cellulose phthalate or hydroxypropylmethyl cellulose. These capsules may be used as such, or alternatively, the lyophilized material may be reconstituted prior to administration, e.g. as a suspension. Reconstitution is advantageously effected in a buffer at a suitable pH to ensure the viability of the organisms. In order to protect the attenuated bacteria and the vaccine from gastric acidity, a sodium bicarbonate preparation is advantageously administered before each administration of the vaccine. Alternatively, the vaccine may be prepared for parenteral administration, intranasal administration or intramammary.

The attenuated bacterium of the invention may be used in the prophylactic treatment of a host, particularly a human host but also possibly an animal host. An infection caused by a microorganism, especially a pathogen, may therefore be prevented by administering an effective dose of an attenuated bacterium according to the invention. The bacterium then expresses a heterologous protein capable of raising antibody to the microorganism. The dosage employed will be dependent on various factors including the size and weight of the host, the type of vaccine formulated and the nature of the heterologous protein. However, for attenuated *S. Typhi* a dosage comprising the oral administration of from $10^9$ to $10^{11}$ *S. Typhi* organisms per dose is generally convenient for a 70 kg adult human host.

Part II A

Anthrax Vaccines

*Bacillus anthracis* is a gram-positive spore-forming bacterium that causes the disease anthrax. The disease is typically initiated by introduction of *Bacillus anthracis* endospores into the body and protection is afforded by an antibody response against the protective antigen (PA) component of anthrax toxin. Recent terrorist activities in Washington D.C. involving the mailing of anthrax spores have now shown that anthrax can serve as an effective bio-terrorist weapon. The only FDA-approved anthrax vaccine is toxoid-based, requires multiple doses to stimulate immunity and causes moderate adverse effects. Clearly, there is a need for new anthrax vaccine approaches. We have chosen to test the feasibility of using an attenuated, *Salmonella Typhi* strain expressing PA to induce an immune response to PA and thus protect against anthrax exposure. The advantages of live attenuated vaccines are: (i) limited multiplication in vivo (aborted infection), thereby inducing an immune response resembling that seen after natural infection; (ii) the need for only one or a few doses to confer long-lasting immunity against certain diseases; (iii) the ability of orally-administered live, attenuated carrier strains such as *Salmonella Typhi* to stimulate both humoral and cellular arms of the immune response; and (iv) self-administration of vaccine, eliminating the need/expense of administration by skilled health care personnel. In these studies, the anthrax PA was cloned behind an inducible promoter in a genetically stable low copy plasmid vector. The live attenuated *Salmonella* vector containing the PA plasmid construct expresses PA intracellularly and under conditions of oxygen limitation. The anthrax PA is expressed at high levels in this system as demonstrated by western blot analysis using a polyclonal anti-PA antibody. Preliminary mouse studies have shown PA-specific immune stimulation. Currently, dosing schedules and administration methods are being optimized. Given the safety record of attenuated *Salmonella* vaccine vectors in humans, a vaccine construct that induces a strong response to PA is envisioned as forming the basis of a safe and effective vaccine against anthrax.

Introduction

*Bacillus anthracis* is a gram-positive spore-forming bacterium that causes the disease anthrax. Anthrax is typically initiated by introduction of *Bacillus anthracis* endospores into the body. Endospores have a high affinity for the regional macrophages and are efficiently and rapidly phagocytosed in vivo. After spore germination and local multiplication within the macrophage (i.e. intracellular events), vegetative bacteria kill the macrophage and are released into the blood stream, where they live as extracellular pathogens and reach high numbers. The vegetative bacilli respond to host signals of physiological body temperature and $CO_2$ levels in order to transcriptionally activate the genes for virulence factors (e.g., capsule and toxins). The anthrax toxin is composed of three subunits: (i) lethal factor (LF), a zinc-metalloprotease, is the toxin component thought to kill host cells by disrupting the mitogen-activated protein kinase pathway; (ii) edema factor (EF), an adenylate cyclase that causes edema in the infected host; and (iii) protective antigen (PA), which binds to eukaryotic cell surface proteins, forms homoheptamers, and then binds to and internalizes EF and LF. LF acts upon macrophages in the body and causes the release of pro-inflammatory cytokines responsible for sudden and fatal shock. The first overt sign of disease is often death itself, which can occur as early as 1-7 days post exposure. Considerable evidence exists to show that antibodies to PA alone can protect against anthrax infection.

Recent events have shown that anthrax can serve as a weapon of choice for bioterrorists. The only FDA-approved anthrax vaccine is toxoid-based, requires multiple doses to stimulate immunity, and causes moderate adverse effects. Clearly, there is a need for new anthrax vaccine approaches.

The majority of available vaccines are composed of: (1) inactivated components, such as formalinized toxoids; (2) inactivated whole virus or bacteria; or (3) purified bacterial antigens, such as capsular polysaccharides. Another class of vaccines consists of live, attenuated strains of bacteria or viruses. The advantages of live attenuated vaccines are: (i) the hi levels of protection obtained from limited multiplication in vivo i.e. an aborted infection), thereby inducing an immune response resembling that seen after natural infection; (ii) the need for only one or a few doses to confer long-lasting immunity against certain diseases; and (iii) the ability of orally-administered live, attenuated carrier strains such as *Salmonella Typhi* to stimulate the humoral, mucosal and cellular arms of the immune response. The simplicity of administering oral vaccines (without the need for a skilled health care specialist) and the potential for low cost manufacturing makes this approach very attractive.

Construction of Plasmid Vector. Anthrax protective antigen (PA) was cloned under the control of the nirB promoter in the low copy plasmid, pGB-2 and the sequence was verified (FIG. 9).

Western Blot of *S. Tyhpi* Ty21a Lysates. Western blot of auxotrophic *S. Typhi* Ty21a cell lysates and culture supernatants separated by SDS-PAGE and probed with polyclonal anti-PA antibody (FIG. 10). *S. Typhi* and *S. Typhi* containing the empty vector and vector +PA were cultured separately overnight at 37° C. in Luria broth (LB) and LB containing spectinomycin, respectively. Then the cultures were grown anaerobically in an air tight jar in presence of GasPack (BBL) catalyst for about 4 hours at 37° C. Harvested cells and supernatants were normalized to similar CFUs per milliliter and lysed in NuPage LDS Sample Buffer, loaded on a NuPage BisTris gel, transferred to a PVDF membrane, and blotted with polyclonal anti-PA antibody.

Plasmid Stability Upon Broth Subculturing. One colony of *S. Typhi* Ty21a expressing PA was grown in LB without antibiotic for 12 hours and the culture was diluted 100 fold and grown again for another 12 hours and this process was continued up to 72 hours. At each-time point of 12, 24, 36, 48, 60 and 72 hours the culture was serially diluted up to $1 \times 10^{-6}$ and plated on LB plates. After 24 hours >100 colonies from each LB plates were replica-plated to LB containing spectinomycin and the percentage of spectinomycin resistant colonies at different time points were calculated (FIG. 11).

Humoral Anti-PA Response in Mice Following IP Immunization. Twelve, 6-8 week old, female BALB/c mice were immunized i.p. with a single dose of $5 \times 10^7$ cells (Ty21a-PA) or 0.5 ml of PBS. Blood samples were collected from the tail vein of all animals on days 14 and 28 after immunization and analyzed by ELISA to determine PA-specific IgG antibody titers. The ELISA assay was conducted by standard procedures using 96-well plates coated with 1 µg/well of purified PA. The endpoint titer is defined as the maximum serum dilution having an optical density (405 nm) of greater than 0.2. Each plot point represents an individual mouse (FIG. 12). The horizontal bars represent mean values.

SUMMARY

Anthrax protective antigen (PA) was cloned under the control of the nirB promoter in the low copy plasmid, pGB-2 and the sequence was verified. The recombinant plasmid containing PA and the empty vector (pGB-2/PnirB) were transformed into *E. coli* and *S. Typhi* Ty21a. The cultures were induced anaerobically for about 4 hours at 37° C. Immunoblot of the cultures with PA specific antibody indicated high level expression of PA in *S. Typhi* Ty21a. This recombinant plasmid containing PA is quite stable during growth in the absence of spectinomycin. Immunization of mice by the IP route with *S. Typhi* expressing PA resulted in a significant rise in anti-PA antibodies.

Part II B

Development of a Vaccine Candidate

A. Specific Aims

Vaccines represent a proven and effective approach for assuring widespread protection of large populations and can reduce the number of susceptible individuals prior to or immediately following a bioterrorism attack. The goal of this project is to address two significant problems that are raised by current bioterrorism threats: 1) the need for an easy method of mass vaccination and 2) the shortcomings of the current anthrax vaccine which requires injection by health professionals for administration, vaccine refrigeration, an extended vaccination schedule for protection (6 doses over 18 months) and the concern over transient side effects. In this context we propose the use of technologies to develop a live, attenuated *Salmonella enterica* serovar *Typhi* strain Ty21a carrying the recombinant protective antigen (rPA) gene of *Bacillus anthracis* on a genetically stable bacterial plasmid. A storage-stable vaccine will be processed into a powder that will be suitable for self-administration by oral or nasal delivery and used to protect against anthrax disease.

The rationale underlying this approach is to exploit the extensive safety record of the existing live, oral Ty21 a vaccine by utilizing it as a vector to develop a live attenuated vaccine carrier stably expressing rPA. Ty21a is envisioned as the vaccine carrier because of the proven safety profile of the licensed Ty21a vaccine, the ability of Ty21a to express PA, and because Ty21a itself triggers long-term protection against typhoid fever. We propose utilizing existing expertise to formulate this vaccine to be stable without refrigeration and in a form for easy oral or nasal administration.

B. Background and Significance

Through the inhalational and gastrointestinal routes, the gram-positive anthrax *Bacillus* causes a disease that starts with mild generalized symptoms and abruptly develops into a systemic, difficult-to-treat form with massive bacteremia, toxemia and fatal shock-like symptoms including sepsis and respiratory failure (Dixon, T. C. et al. 1999 *New Engl J Med* 341:815-826; Mock, M. and Fouet, A. 2001 *Annu Rev Microbiol* 55:647-671). Since 2001 the primary disease concern has been the use of *B. anthracis* spores as a bioterrorist weapon, particularly administered via the inhalational route. Anthrax spores exhibit a high degree of physical stability and can be readily processed into an inhalable powder. It is listed as a NIH category A agent indicating the highest priority for developing effective and rapid medical interventions.

Vaccination is capable of preventing infectious diseases such as smallpox and is likely to be one of the most effective counter measures against a weaponized anthrax attack, because it is the most efficient way to reduce the number of susceptible individuals prior to or immediately following an attack. Most importantly, for widespread use a vaccine must be safe and efficacious. Ideally, the vaccine would also be simple and inexpensive to store and distribute and could be administered easily to large populations over a relatively short time period. One approach is an oral or nasal vaccine delivered without lengthy reconstitution procedures (thus dispensing with the need for syringes/needles and skilled health care professionals) in fewer than the current 6 doses, that could withstand storage and distribution for prolonged periods outside the cold chain (i.e., at room temperature and above). Currently, stockpiling sufficient Anthrax vaccine for emergency uses is a major challenge, because of its strict temperature requirement (refrigeration) and relatively rapid expiration. The proposed format would facilitate vaccine storage, stockpiling and mass immunization in a manageable timeframe whether in a civilian biodefense setting or the military.

Anthrax vaccine development has focused on the major virulence factors of *B. anthracis*, which are plasmid encoded toxin production and capsule formation (Mock, M. and Fouet, A. 2001 *Annu Rev Microbiol* 55:647-671; Dixon, T. C. et al. 1999 *New Engl J Med* 341:815-826). The toxin-gene complex produces three secreted components, protective antigen (PA) lethal factor (LF) and edema factor (EF). These three factors form two binary toxins, lethal toxin (LT) composed of PA and LF and edema toxin (ET) consisting of PA and EF. The anthrax vaccine in the United States, which is similar to the vaccine in the United Kingdom, is an aluminum hydroxide adsorbed vaccine consisting of PA-containing supernatant material from fermenter cultures of a non-encapsulated, toxigenic strain of *B. anthracis*, V770-NP1—R (Anthrax Vaccine Adsorbed, AVA, currently sold as Biothrax). Although no human clinical efficacy data is available with the current vaccine, a less potent precursor was shown to be protective in placebo-controlled clinical trials (Friedlander, A. M. et al. 2002 *Curr Top Microbiol Immunol* 271:33-60). One of the drawbacks of this vaccine is that multiple immunizations are required over a prolonged period, e.g., AVA is administered subcutaneously in a 6 dose regimen at 0, 2 and 4 weeks and then at 6, 12 and 18 months. This would clearly not be appropriate for a post-exposure vaccine and is problematic when trying to achieve a high level of compliance in large populations. In addition, compliance is likely to improve simply by developing a more convenient oral dosage form. Although the US vaccine is safe, a less reactogenic vaccine would significantly improve its acceptability in recipients (Larkin, M. 2002 *Lancet* 359:951).

Early cloning and expression of PA in *B. subtilis* demonstrated that PA alone was sufficient for protective immunity (Ivins, B. E. and Welkos, S. L. 1986 *Infect Immun* 54:537-542; Ivins, B. E. et al. 1998 *Vaccine* 16:1141-1148). Since then, various expression systems have been explored as a potential source of purified PA for use as a vaccine including a plasmid-free, asporogenic *B. anthracis* strain (Farchaus, J. W. et al. 1998 *Appl Environ Microbiol* 64:982-991). In order to increase the immunogenicity and efficacy of protein vaccines, adjuvants and microsphere-associated rPA have been tested with mixed success (Friedlander, A. M. et al. 2002 *Curr Top Microbiol Immunol* 271:33-60; Flick-Smith, H. C. et al. 2002 *Infect Immun* 70:2022-2028). Alternatively, by chemically conjugating PA to capsular poly($\gamma$-D-glutamic acid) a dually active anthrax vaccine that may protect against bacilli and toxins was recently constructed (Rhie, G-E et al. 2003 *Proc Natl Acad Sci USA* 100:10925-10930; Schneerson, R. et al. 2003 *Proc Natl Acad Sci USA* 100:8945-8950).

One significant advantage of live-attenuated vaccines over purified protein vaccines is the potential to circumvent the use of needles for administration by a trained health care professional. In addition, live-attenuated anthrax vaccines have often demonstrated broader protection in animal models with fewer doses, faster immune response and longer lived immunity (Friedlander, A. M. et al. 2002 *Curr Top Microbiol Immunol* 271:33-60). Several vaccine candidates have shown promise in early animal studies, but will require further optimization before human studies can be considered (Welkos, S. L. and Friedlander, A. M. 1988 *Microbial Pathogenesis* 5:127-139; Zegers, N. D. et al. 1999 *J Appl Microbiol* 87:309-314).

Attenuated strains of *Salmonella enterica* serovars *Typhimurium* and *Typhi* offer a well tested vehicle for oral presentation of heterologous antigens to stimulate mucosal and cell mediated immunity, because of their ability to invade the gut via the lymphoid tissues (Friedlander, A. M. et al. 2002 *Curr Top Microbiol Immunol* 271:33-60; Garmory, H. S. et al. 2003 *Infect Immun* 71:3831-3836). In addition to *B. anthracis*, other bacterial antigens that have been delivered in this way include the following organisms: *S. sonnei*, *S. flexneri* 2A, *E. coli*, *V. cholera*, *F. tularensis*, *C. tetanus*, *B. pertussis*, *P. aeruginosa*, *N. meningiditis*, *S. mutans*, *S. sobrinus* and *S. pyogenes* (Schodel, F. 1992 *Adv Virus Res* 41:409-446). Similarly, viral antigens include the following viruses: dengue, hepatitis B virus, human papillomavirus, influenza and measles (Schodel, F. 1992 *Adv Virus Res* 41:409-446; Baud, D. et al. 2004 *Infect Immun* 72:750-756; Pasetti, M. F. et al. 2003 *J Virol* 77: 5209-5217). The current study is aimed at developing a live-attenuated vaccine using *S. enterica* serovar *Typhi* strain Ty21a carrying the rPA gene of *B. anthracis* on a stable bacterial plasmid. This study is based on the prior human efficacy data for Ty21a as a typhoid vaccine and the unrivaled safety record of this commercial vaccine (Vivotif Berna® Vaccine). There has never been a reported case of documented bacteremic dissemination of the highly attenuated Ty21a in a human. Also, there are no reports of postinfectious inflammatory arthritis (e.g., Reiter's syndrome) after vaccination with Ty21a, a potential problem with nontyphoid *Salmonella*, *Shigella*, and *Yersinia* vectors. Additionally, Ty21a generates long-lived immunity that does not require a booster vaccination for at least 5 years (Levine, M. M. et al. 1999 *Vaccine* 17:S22-S27). One research area over the past 20 years has been to develop attenuated *S. Typhi* strains with defined alterations, which have improved immunogenicity and potentially can be given in fewer doses than Ty21a (Hohmann, E. L. et al. 1996 *J Infect Dis* 173:1408-1414; Wang, J. Y. 2001 *Infect Immun* 69:4734-4741). However, these candidates not only lack the substantial clinical safety and efficacy data available for Ty21a, but the clinical development of many of these candidates has been slowed by difficulties in achieving the desired (but often elusive) balance between low reactogenicity and strong immunogenicity (Dilts, D. A. et al. 2000 *Vaccine* 18:1473-1484).

A significant issue with large-scale immunization programs is the stability of the vaccine during storage, shipment and administration. According to a US Army study, up to 15% of vaccine and immunologic drug shipments were subjected to unacceptable temperature conditions (Frank, K. J. 1999 *Am J Health-Syst Pharm* 56:2052-2055). Similarly, it is estimated by the WHO that the cost of cold chain failures worldwide is approximately $200 M annually. To address this issue, more suitable vaccines for rapid, large-scale distribution and immunization programs are needed with enhanced stability and delivery characteristics. Long-term stabilization of bacteria for storage at elevated temperatures requires the addition of stabilizers followed by a drying step to remove water (Crowe, J. H. et al. 1998 *Annu Rev Physiol* 60:73-103) and packaging that prevents moisture uptake. Such stabilizers tend to be non-reducing disaccharides, which can be dried to an amorphous glassy state (Carpenter, J. F. et al. 2002 *Pharm Biotechnol* 13:109-133). Among the drying processes that have been used for biopreservation include freeze drying (lyophilization) (Franks, F. 1998 *Eur J Pharm Biopharm* 45:221-229), spray drying (Truong-Le, V. L. 2003 "Stabilization of live virus vaccines" IBC Conference on Formulation Strategies September 23$^{rd}$ Abstract 116), spray freeze drying (Costantino, H. R. et al. 2000 *Pharm. Res* 17:1374-1383), air drying (Potts, M. 1994 *Microbiol Rev* 58:755-805), and foam drying (Annear, D. I. 1970 *J Hygiene* 68:457-461). Among these, freeze drying has been the process of choice to stabilize a wide range of biologics including proteins (Carpenter, J. F. et al. 2002 *Pharm Biotechnol* 13:109-133), viruses (Burke, C. et al. 1999 *Critical Rev in Therapeutic Drug Carrier Sys* 16:1-83), and bacteria (Corbel, M. J. 1996 *Dev Biol Stand* 87:113-124; Burke, C. 1999 *Critical Rev in Therapeutic Drug Carrier Sys* 16:1-83). In addition, new aluminum packaging technologies have been developed to avoid problems associated with premature moisture ingress.

After stabilization by lyophilization, Ty21a exhibits a shelf life, of approximately 18-24 months at 2-8° C. (Burke, C. et al. 1999 *Critical Rev in Therapeutic Drug Carrier Sys* 16:1-83; Clarke, P. D. and Forrest, B. D. 1993 WO patent 93/11220), which is typical of many stabilized bacterial vaccine preparations. When exposed to 37° C., lyophilized Ty21a exhibited a half-life of only one day (Clarke, P. D. and Forrest, B. D. 1993 WO 93/11220; Cryz, S. J. et al. 1996 *Dev Biol Stand* 87:277-285), which would not meet WHO requirements for storage outside the cold chain (Milstein, J. B. and Gibson, J. J. 1990 *Bull WHO* 68:93-108), and assuming linear Arrhenius-like kinetics, would have a half-life at 25° C. (i.e., room temperature) of ~2-3 days. Previous experience indicates that an enveloped RNA virus, such as influenza, is equally unstable. For example, lyophilized live PR8 influenza virus loses up to 1 $\log_{10}$ of potency in 1-3 days at 37° C. depending on the residual moisture content (Hone, D. M. et al. 1988 *Infect Immun* 56:1326-1333) and a live attenuated influenza virus, when stabilized with sucrose based formulations, loses 1 $\log_{10}$ of infectivity in 2-4 days when stored at room temperature (Truong-Le, V. L. 2003 "Stabilization of live virus vaccines" IBC Conference on Formulation Strategies September 23$^{rd}$ Abstract 116). However, using appropriate formulations and either freeze dry foaming or spray drying we have now demonstrated long-term stabilization of live influenza viruses (see below). Given the similar stability profile of Ty21a and influenza virus, we believe that appropriate formulation and drying stabilization strategies should be applicable to Ty21a. More importantly, it is known that bacteria including *E. coli, Salmonella ndolo* and *Pseudomonas syringae* have been stabilized for long-term survival at room temperature using in vacuo foam drying conditions similar to those used with influenza (Annear, D. I. 1970 *J Hygiene* 68:457-461; Bronshtein, V. 2003 U.S. Pat. No. 6,509,146; Iijima, T. and Sakane, T. A. 1973 *Cryobiol* 10:379-385; Fry, R. M. and Greaves, R. I. 1951 *J Hyg* 49:220-246).

In summary, we developed a vaccine candidate utilizing the already proven safe and efficacious typhoid vaccine strain Ty21a as a vehicle to deliver plasmid-expressed PA. The final vaccine product will be formulated into a stable dried powder that can be delivered orally or nasally. A vaccine is ultimately provided with an easy to administer single dose unit.

Experimental Data

1. Construction of Multiple Recombinant Plasmids to Optimize Expression of Anthrax PA Our previous studies with pGB-2, a low copy (i.e. 5-7 copies/cell) cloning vector, which contains a selectable spectinomycin resistance gene and a multiple cloning site (MCS) locus, resulted in high level expression of heterologous antigens and increased genetic stability in *S. enterica* serovar Typhi strain Ty21a compared to multicopy plasmids (Xu, D. Q. et al. 2002 *Infect Immun* 70:4414-23). The increased stability is likely due to the reduced metabolic load on the host. For this study use specifically regulated genetic promoters to allow PA gene expression under well-defined environmental conditions, which may provide additional genetic stability. These regulated promoters display low-level expression of the heterologous antigen during vaccine manufacture, but have maximal activity following immunization as *Salmonella* infects intestinal cells. We have designed several plasmid constructs for the expression of anthrax protective antigen under the control of two environmentally inducible promoters. The first is the anaerobically inducible (transcription factor FNR dependent) nirB promoter and the second one is the htrA promoter (sigmaE-RNA polymerase dependent), both of which are fully activated during *Salmonella* infection of eukaryotic cells. These promoters were shown to drive the expression of heterologous proteins, under inducing conditions, to levels as high as 20-30% of total cell protein (Oxer M. D. et al. 1991 *Nucleic Acids Res* 19:2889-2892).

A third method to optimize expression of protective antigen, previously used in Gram-negative bacteria, employs a synthetic PA gene that is codon-optimized for expression in *S. Typhi*. A codon-modified PA gene (PAcm) was constructed synthetically with terminal Nde1 and BamH1 restriction sites for directional cloning. The htrA promoter region was PCR-amplified from the Ty21a genome using primers that introduced HindIII and NdeI restriction enzyme sites at the 5' and 3' ends of the gene respectively (FIG. 13). The 3'-end primer also contains an optimal Shine-Delgarno sequence (AGGAG). The nirB promoter region was generated by combining two complementary synthetic oligo-nucleotides leaving EcoRI and NdeI sticky-ends (FIG. 13). An optimal Shine-Delgarno sequence was also engineered into this promoter region. The plasmid vector was prepared by restriction digest using HindIII/BamHI for htrA constructs or EcoRI/BamHI for nirB constructs (FIG. 13). Typically, three different fragments with compatible ends were combined in a ligation reaction to generate the final expression plasmids.

2. Secretion of PA for Enhanced Immunogenicity

In order to enhance the immunogenicity of *Salmonella*-produced anthrax PA, we have inserted secretion systems that target PA to either the bacterial periplasmic or extracellular spaces. Targeting to the periplasm was achieved by creating an N-terminal genetic fusion between PA and gene III Sec signal sequence from the filamentous phage fd (i.e. this 18 amino acid N-terminal signal sequence is dependent on the bacterial Sec system for secretion to the periplasmic space; Invitrogen, CA). PA can also be secreted extracellularly using the well-studied E. coli haemolysin secretion system (Gentschev I. et al. 2002 Trends Microbiol 10:39-45). We have created in-frame C-terminal fusions of PA with the haemolysin secretion signal HlyAs. The genetic fusion was cloned into pGB-2 containing HlyB and HlyD. Representative constructs, developed separately for both wild type PA and codon-optimized PA, are shown diagrammatically in FIG. 14.

3. Expression of PA Under Inducing Conditions

As listed in Table 4, twelve plasmids containing the two PA genes (i.e. PAwt and PAcm) have been constructed to analyze expression of each from two different promoters (phtrA, pnirB) and coupled with or without two different secretion systems (fd and Hly). DNA sequence analyses have, thus far, confirmed the expected sequences in half of these constructs with the remainder to be tested. Expression of protective antigen in these Ty21a strains can be induced, in vitro, by elevating the temperature to 42° C. during growth for htrA constructs, or by growing the strains under anaerobic conditions for nirB constructs. In preliminary experiments with two constructs, htrA-regulated expression of PA results in approximately 0.5 μg/$10^9$ cfu of Ty21a expressing wild-type PA (phtrA-PAwt) and approximately 10 μg/$10^9$ cfu of Ty21a expressing codon-modified PA (phtrA-PAcm). Thus, the yield of PA in Ty21a can be increased about 20-fold by using a synthetic, codon-optimized gene. These results are shown in FIG. 15.

TABLE 4

Ty21a-PA Vaccine Constructs

| Pawt | PAcm | Localization |
|---|---|---|
| phtrA | phtrA | intracellular |
| pnirB | pnirB | intracellular |
| phtrA-fd | phtrA-fd | periplasmic |
| pnirB-fd | pnirB-fd | periplasmic |
| phtrA-Hly | phtrA-Hly | extracellular |
| pnirB-Hly | pnirB-Hly | extracellular |

4. Plasmid Stability Upon Sub-Culturing without Selection

One of the key requirements for a live attenuated bacterial vector is plasmid stability, both during in vitro growth for manufacture and during in vivo growth within the immunized host. To test for pGB-2 stability, one colony of Ty21a (pnirB-PAwt) was grown in LB broth without spectinomycin for 12 hrs, and the culture was diluted 100-fold and grown for another 12 hrs, and this process was repeated every 12 hrs for a total of 72 hrs. At each time point (12, 24, 36, 48, 60, and 72 hrs) the culture was serially diluted and plated on LB agar plates. After 24 hrs, >100 colonies from each LB agar plate were replicated to LB agar containing 25 μg/ml spectinomycin and the percentage of spectinomycin resistant colonies were calculated. 100% of the resultant colonies were Spc-R, indicating highly stable plasmid maintenance under nonselective growth conditions over 72 hrs, which represents >50 generations.

5. Immune Response and Protection in Mice

Our ultimate goal is aimed at producing a formulated vaccine that can be delivered orally or intranasally to humans. We have initially focused on the intraperitoneal route of immunization in mice for simplicity, reproducibility and to directly compare the responses to those reported by others (Garmory, H. S. et al. 2003 *Infect Immun* 71:3831-3836). Once the dose level, immunization schedule and plasmid construct have been optimized for maximum immune stimulation, oral and/or intranasal immunization will be tested. Our experimental data was generated with the non-optimized Ty21a-PAwt construct (non-optimized codon usage, constitutive promoters and intracellular localization) expressing only ~5% of the optimum PA expression shown above (FIG. 15). Three groups of 12 female BALB/c mice, 6-8 weeks old, were immunized intraperitoneally (i.p.) with a single dose of $5\times10^7$ cfu of Ty21a expressing PAwt [Ty21a-PAwt], $5\times10^7$ cfu of Ty21a-PAwt lysed by sonication (i.e. to mimic PA secretion), or with 0.5 ml of PBS. Mice were boosted with an identical dose four weeks after the first immunization. This dosing regimen is shown diagrammatically in FIG. 16. Blood samples were collected from the tail vein of all animals on days 14, 28, 48, and 65 after the first immunization. Serum samples were analyzed by ELISA to determine PA-specific IgG antibody titers. Mice vaccinated with a single injection of Ty21a-PAwt elicited a significant humoral response to PA with antibody geometric mean titers (GMT) of 100-200. Following a boost at four weeks the antibody titers increased at least two-fold for mice immunized with either Ty21a-PAwt (500 GMT) or lysed Ty21a-PAwt (210 GMT). These titers were maintained for at least four weeks after boosting (FIG. 17).

As an initial test of protective efficacy that can be performed under BSL-2 conditions, mice immunized with Ty21a-PAwt were challenged with a lethal dose of anthrax lethal toxin (LT) 9 weeks after the first immunization. The stringent challenge consisted of LT (50 μg of PA plus 25 μg of LF, i.e., ~50 $LD_{50}$'s) administered i.v. in the tail in a volume of 100 μL. All 12 mice in the PBS control group and all mice immunized with whole Ty21a-PAwt succumbed to the challenge. However, 2 of 11 mice (18%) immunized with lysed Ty21a-PAwt survived the challenge and the remaining 9 mice had time to death (TTD) prolonged by 1 day. Prolongation in TTD has been noted in other studies (Welkos, S. L. and Friedlander, A. M. 1988 *Microbial Pathogenesis* 5:127-139). Though preliminary, these data lend support to a recent finding (Garmory, H. S. et al. 2003 *Infect Immun* 71:3831-3836) that secreted PA is more effective than intracellular PA at triggering protection. In other preliminary studies, 3 vaccine doses of the same construct have stimulated an anti-PA GMT of >1000 in unchallenged mice. At this point, all immunizations have been conducted with PAwt constructs which produce only ~5% of the PA antigen of PAcm constructs. Immunization studies with optimal PAcm expression will be initiated shortly and we believe that optimal dosing strategies combined with secreted expression of induced PAcm will trigger high levels (i.e. >10,000 GMT) of anti-PA in mice and provide strong protection against challenge.

6. Physical Stabilization of Influenza Virus Dry Formulations

One of our goals is to produce a vaccine with optimal physical as well as genetic stability. Our experience in stabilizing thermally labile live organisms has centered on live attenuated influenza virus as a model vaccine. The stability of influenza virus vaccine stabilized in a conventional sucrose-phosphate-glutamate (SPG) buffer is shown in Table 5. Although stable for several months in the frozen state (−20° C.), it loses potency at room temperature (25° C.) in approximately 6 days.

TABLE 5

| The stability of influenza virus vaccine | |
|---|---|
| Storage Temperature | Time to 1 log loss ($Log_{10}$ $TCID_{50}$/mL) |
| −20° C. | 8-12 months (depending on the strain) |
| 2-8° C. | <2 months |
| 25° C. | 6 days |
| 37° C. | <5 days |

To enhance storage stability, many researchers have employed conventional lyophilization approaches with limited success. An often-mentioned challenge associated with this drying process has been how to minimize protein structural damage that can occur during the freezing step (Anchordoquy, T. J. et al. 2001 *Arch Biochem Biophys* 390:35-41). Using lyophilization, long-term stability of live influenza could be achieved at refrigerated temperature; however, this stabilized preparation still loses one $log_{10}$ of infectivity within 1-2 months at room temperature (Greiff, D. and Rightsel, W. A. 1968 *Appl Microbiol* 16:835-841).

Stabilization by Spray Drying

In spray drying, a liquid feed is spray atomized into fine droplets under a stream of dry heated gas. The evaporation of the droplets results in powders made of the dissolved solutes. A gentle spray drying process was developed that removed water from influenza vaccine without exposing the virus to extreme temperature cycles. The mild thermal drying process efficiently dries liquid formulations at lower heating temperatures than other spray drying processes. A component of this process is an atomizing nozzle that can generate ultra-fine liquid droplets, thereby increasing the effective surface area-to-volume ratio. The increased surface area facilitates the evaporative process and thus permits drying at lower temperatures and reduced thermal stress. Live attenuated influenza vaccine formulated and dried using a thermally mild spray drying process resulted in the preservation of virus infectivity at room temperature (25° C.) for almost 1 year (FIG. 18). This represents a greater than 50-fold increase in the shelf life of the vaccine.

Stabilization by Freeze Dry Foaming

A second drying technology to preserve influenza virus infectivity is termed freeze dry foaming. This is essentially a freeze-drying process that is done under cake collapse conditions. In contrast to conventional freeze drying, this mode of freeze drying does not subject the product to prolonged potentially damaging deep freeze cycles because sublimation of ice occurs more rapidly over a larger total surface area. A second potential advantage is that the dried foams exhibit significantly lower specific surface area than conventional freeze-dried cakes or spray-dried powders, which appears to be a preferable solid state for long term storage due to the smaller total surface area available for heat and mass transfer as well as lower total surface tension. This process incorporates the use of a plasticizer formulation strategy to optimize structural retention (Cicerone, T. C. et al. 2003 *Bioprocess Int* 1:2-9). The resultant dry glassy foam can be reconstituted with a diluent for liquid administration or milled into fine powder for solid dosage form administration. Influenza virus stabilized with the freeze dry foam technology resulted in substantial shelf life during room temperature storage (FIG. 19). During a 22 month real-time stability study at room temperature, three influenza virus strains (H1N1, H3N2 and B) all had shelf lives (≦1 $log_{10}$ infectivity loss) greater than 2 years and 2 strains had a shelf life of 4 years or greater (FIG. 19 A-C). These stability profiles should be adequate to provide a commercially viable shelf-life which is typically about 18 months.

7. Production of Particle Size for Optimal Nasal Deposition

Figure 20A:
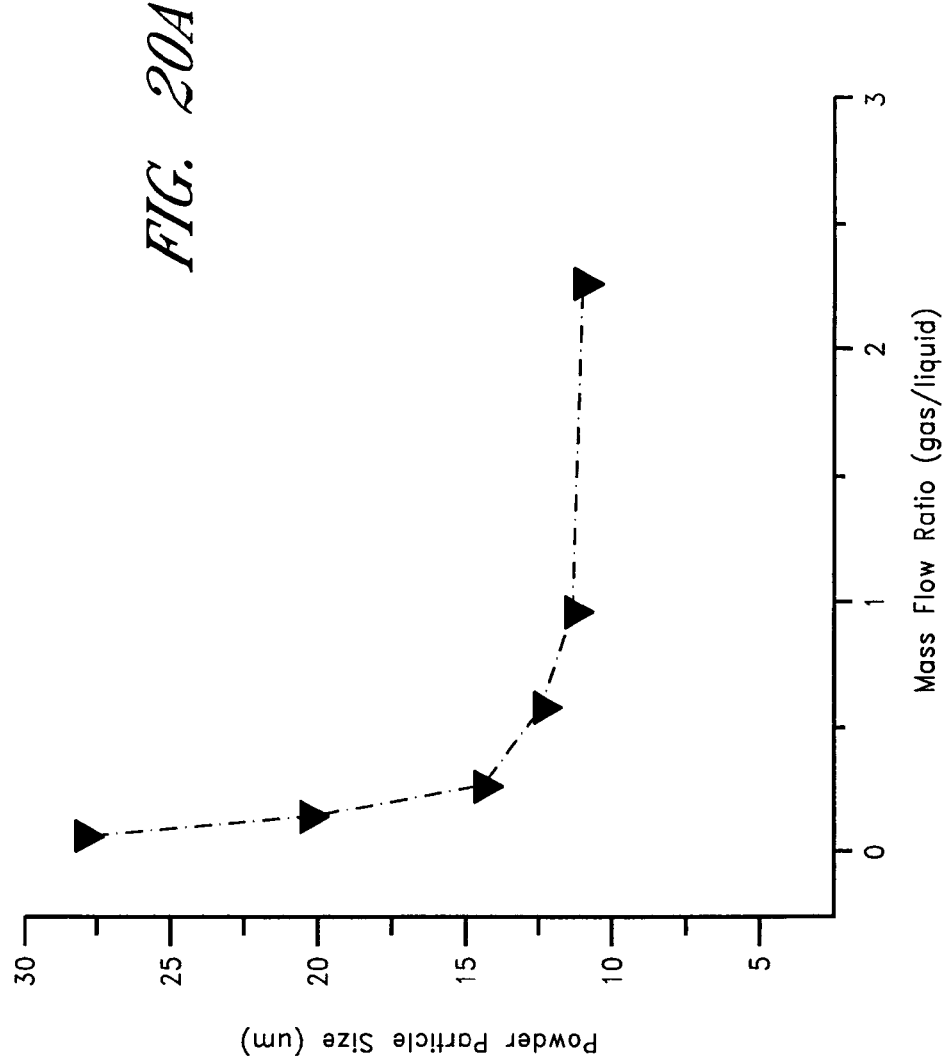
Figure 20B:
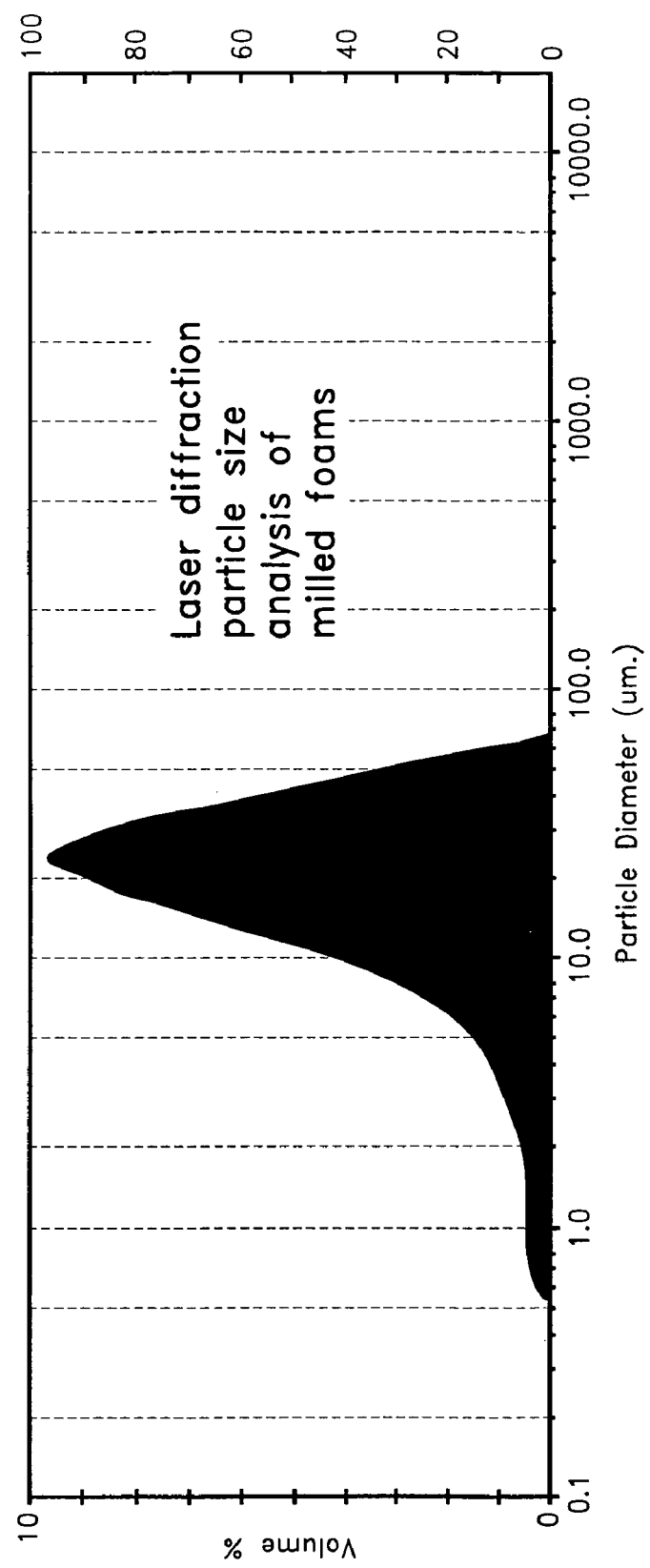

Powder particles that exhibit a size range of approximately 5 to 100 microns are optimal for nasal deposition while those less than ~3 microns can penetrate to lower lung airways (Heyder J et al. 1986 *J Aerosol Sci* 17:811-825). We have found that both spray drying and freeze dry foaming processes could be used to manufacture dry powder particles with appropriate size range for nasal deposition (FIG. 20 A & B). Our data showed that the spray drying process could produce a range of specific powder particle sizes (FIG. 20A). For the freeze dry foaming process, the resultant foam was further processed into fine powder by employing conventional mechanical impact milling equipment. The extent of grinding directly affected the final particle size distribution (FIG. 20B).

Part II C

Plasmid Construction Strategies

Cloning of nirB Promoter Region in Plasmid pGB-2. A synthetic nirB promoter was created by Taq polymerase extension of annealed oligonucleotides S100 and S101 (SEQ ID NOs: 19 and 20, respectively and see Table 6) containing a complementary 20-bp region at their respective 3' ends. The 90 by product was PCR amplified using oligonucleotide primers S102 and S103 (SEQ ID NOs: 21 and 22, respectively and see Table 6). The PCR product with an Eco RI restriction site at the 5' end and a SmaI site at the 3' end was cloned into the EcoRI and SmaI restriction sites of plasmid pGB-2 by digestion with EcoRI and SmaI followed by ligation with T4 DNA ligase. Plasmid pGB-2 is a low copy (i.e. 5-7 copies/cell) cloning vector, which contains a selectable spectinomycin resistance gene and a multiple cloning site (MCS) locus. The ligated products were transformed into an *E. coli* host (XL-1 Blue) for amplification and *Salmonella Typhi* Ty21a for protein expression analysis (see FIG. 21).

Generation of htrA Promoter. The htrA promoter region was PCR amplified from *Salmonella Typhi* TY21a genomic DNA using primers M105 and M106 (SEQ ID NOs: 29 and 30, respectively and see Table 6) containing HindIII and NdeI restriction sites, respectively (see FIG. 22). Primer M106 also includes a strong Shine-Dalgarno sequence (AGGAG) just upstream of the ATG codon, which is also part of the NdeI site.

Intracellular Expression of Protective Antigen pnirB-PA Expression Systems. The nirB promoter region was PCR amplified from plasmid pGB-2/nirBp with oligonucleotides M100 and M110 (SEQ ID NOs: 27 and 31, respectively and see Table 6) to generate a product having an EcoRI restriction site at the 5' end and an NdeI site at the 3' end. Oligonucleotide M101 also contains a strong Shine-Dalgarno sequence (AGGAG) just upstream of the start ATG codon. The gene encoding the mature form of protective antigen (PA) (see FIG. 23) was isolated from plasmid pYS5 (Singh, Y. et al. 1989 *J. Biol. Chem.* 264:19103-19107) by restriction endonuclease digestion with NdeI and BamHI. The Eco RI-Nde I nirB promoter fragment (109 bp) and the Nde I-Barn HI PA fragment (2202 bp) were then cloned into the EcoRI and BamHI restriction sites of plasmid pGB-2 via a three-way ligation reaction. Similarly, a synthetic codon-modified version of the PA gene (PAcm) (see FIG. 23) was cloned into pGB-2, downstream from the nirB promoter (see FIG. 24).

htrA-PA Expression Systems. As before, the gene encoding the mature protective antigen (PA) of *B. anthracis* was isolated from plasmid pYS5 by restriction endonuclease digestion with NdeI and BamHI. The HindIII-NdeI htrA promoter fragment (116 bp) and the NdeI-BamHI PA fragment (2202 bp) were then cloned into the HindIII and BamHI restriction sites of plasmid pGB-2. The same strategy was used to clone PAcm downstream from the htrA promoter (see FIG. 25).

Periplasmic Expression Systems. Targeting to the periplasmic space is achieved by creating an N-terminal genetic fusion between PA and the 18 amino acid geneIII Sec-dependent signal sequence (fds) from the filamentous phage fd. After synthesis in the cytoplasm, the fusion protein is transported through the inner membrane, and the signal sequence is then cleaved off (Ito, K. et al. 1980 *J Biol Chem* 255:2123-2130).

pnirB-fds-PA. The genetic fusion between the geneIII signal sequence and PA was made by a three-step PCR amplification procedure. In the first step, PA was PCR amplified using oligonucleotides S110 and S111 (SEQ ID NOs: 23 and 24, respectively and see Table 6). S110 creates the fusion by encoding the first 5 amino acids of PA downstream of the last 9 amino acids of the geneIII signal sequence. The product of the first PCR reaction was used as the template for the next reaction using oligonucleotides S112 and S111 (SEQ ID NOs: 25 and 24, respectively and see Table 6). S112 encodes the first 9 amino acids of the geneIII signal sequence. The last PCR reaction involves oligonucleotides S113 and S111 (SEQ ID NOs: 26 and 24, respectively and see Table 6) which amplify the fusion product and introduce a BglII restriction site at the 5' end and a BamHI site at the 3' end. This final product was restriction endonuclease digested with BglII and BamHI and cloned into the BglII/BamHI sites of plasmid pGB-nirBp (see FIG. 26).

pnirB-fds-PAcm. Fusion of the fd signal sequence (fds) to the codon-modified PA gene (PAcm) was done by first amplifying the nirBp-fds region of plasmid pnirB-fds-PA with oligonucleotide primers M101 and M111 (SEQ ID NOs: 28 and 32, respectively and see Table 6). Primer M101 anneals to vector (pGB-2) sequences upstream of the nirB promoter. Primer M111 anneals to the 3' end of the geneIII signal sequence and is complementary to the first 20 by of PAcm. The 240 by PCR product was then used as the 5'-end primer for a subsequent PCR reaction to amplify PAcm. Oligonucleotide M101 was used as the 3'-end primer. The amplified fds-PAcm product was then digested with XbaI and BamHI and used to replace the nirBp-fds-PA region of plasmid pnirB-fds-PA which had also been digested with XbaI and BamHI (see FIG. 27).

htrA-fds-PA Expression Systems. The fds-PA and fds-PAcm gene fusions were PCR amplified from plasmid pnirB-fds-PA (PAcm) with oligonucleotide primers M112 and M101 (SEQ ID NOs: 33 and 28, respectively and see Table 6). Primer M112 introduces an NdeI site at the ATG start codon of the geneIII signal sequence and M101 anneals to vector sequences just downstream form the BamHI site. The PCR products were restriction enzyme digested with NdeI and BamHI and cloned into vector phtrA-PA replacing the PA gene (see FIG. 28).

Expression Systems for PA Secretion htrA-PA-HlyA$_s$. The C-terminal 60 amino acids of the hlyA gene product are sufficient to effect the secretion of HlyA as well as other polypeptides fused to this secretion signal (Gentschev I. et al. 1996 *Gene* 179:133-140). The C-terminal 183 nucleotides encoding the secretion signal of the hlyA gene product (HlyA$_s$) (60 amino acids+stop codon), and the DNA region encoding the Hly B and Hly D gene products were PCR amplified using oligonucleotide primers M120 and M121 (SEQ ID NOs: 34 and 35, respectively and see Table 6). The resulting PCR product (~3.9 kb) was restriction enzyme digested with NsiI and BamHI (see FIG. 29A).

The gene encoding PA (or PAcm) was PCR amplified with primers M100 and M125 (SEQ ID NOs: 27 and 36, respectively and see Table 6) to remove the stop codon at the 3' end and instead introduce an NsiI restriction site for in-frame ligation at the NsiI site of the HlyAs-BD cassette. The resulting PCR product was restriction endonuclease digested with NdeI and BamHI (see FIG. 29B).

Figure 29C:
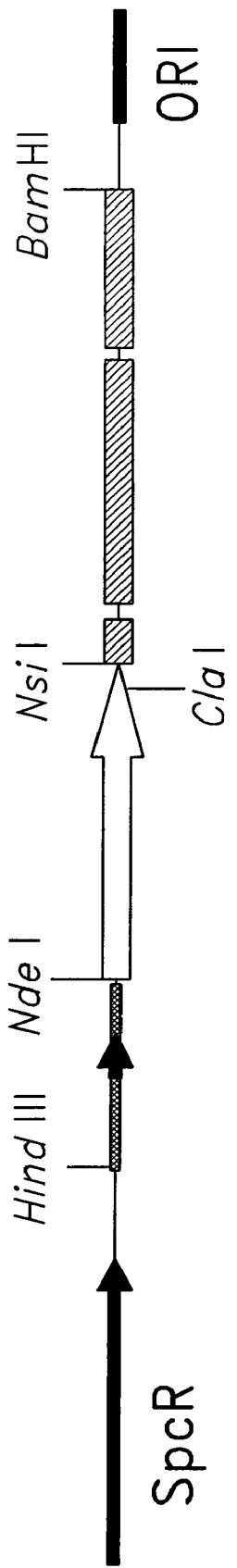

A three-way ligation was performed to ligate both PA (PAcm) and the HlyAs-BD cassette into plasmid pGB-2/htrAp (see FIG. 29C).

NirB-PA-Hly. As with the htrA-PA-Hly constructs, the amplified PA genes lacking the stop codon, together with the Hly cassette were ligated into the NdeI and BamHI sites of plasmid pnirB-PA replacing PA and placing the PA-HlyAs fusion under the control of the nirB promoter (see FIG. 30A). Placement of the PAcm-HlyAs fusion under the control of the nirB promoter was done by restriction enzyme digestion with ClaI, unique, internal site in PAcm, and BamHI (see FIG. 30B). This partial PAcm-HlyAs fusion fragment was then cloned into the ClaI and BamHI restriction sites of plasmid phtrA-PAcm replacing the last 182 nucleotides (ClaI/BamHI fragment) (see FIG. 30C).

SUMMARY

A total of 12 expression plasmids for Protective Antigen were created:
1. pnirB-PA
2. pnirB-PAcm
3. pnirB-fds-PA
4. pnirB-fds-PAcm
5. pnirB-PA-hlyAs-BD
6. pnirB-PAcm-hlyAs-BD
7. phtrA-PA
8. phtrA-PAcm
9. phtrA-fds-PA
10. phtrA-fds-PAcm
11. phtrA-PA-hlyAs-BD
12. phtrA-PAcm-hlyAs-BD

TABLE 6

Oligonucleotides used in this study

| Oligo-nucleo-tide | SEQ ID NO. | Nucleotide Sequence[a] | Description |
|---|---|---|---|
| S100[b] | 19 | 5'-GGAATTCCGCTCTAGAGCGGTAAATTTG ATGTACATCAAATGGTACCCCTTGCTGAA TCG-3' | Synthetic nirB promoter, EcoRI |
| S101[b] | 20 | 5'-TCCCCCGGGTTAAGATCTGGGCCCTACC GCCTACCTTAACGATTCAGCAAGGGGTA CCA-3' | Synthetic nirB promoter, SmaI |
| S102 | 21 | 5'-GGAATTCCGCTCTAGAGCGG-3' | nirB promoter, 5' PCR primer, EcoRI |
| S103 | 22 | 5-TCCCCCGGGATTAAGATCTG-3' | NirB promoter, 3' PCR primer, Sma I, BglII |
| S110 | 23 | 5'-CTGGTGGTGCCGTTCTATAGCCATAGCG AAGTTAAACAGGAA-3' | fds-PA fusion, first PCR, 5' primer |
| S111 | 24 | 5'-CGGGATCCCGTCACCTAGAATTACC-3' | PA 3'-end, BamHI |
| S112 | 25 | 5'-ATGAAAAAACTGCTGTTCGCGATTCCGC TGGTGGTGCCG-3' | fds-PA fusion, second PCR, 5' primer |
| S113 | 26 | 5'-GGAAGATCTTAATCATCCACAGGAGAC TTTCTGATGAAAAAACTGCTG-3' | fds region upstream, 5' PCR primer, BglII |
| M100 | 27 | 5'-GGCTGGCTTTTTCTTGTTATCGC-3' | PGB-2 PCR/sequencing primer, upstream of HindIII |
| M101 | 28 | 5'- CTAATGCACCCAGTAAGGCAGCGG-3' | PGB-2 PCR/sequencing primer downstream of EcoRI |
| M105 | 29 | 5'-GCGCAAGCTTTGGACTTTTGTAAAGATG G-3' | htrA promoter upstream region, HindIII |
| M106 | 30 | 5'-GGGCATATGTCCTCTCCTTAAAATTGCT GTGTACG-3' | htrA promoter region downstream, NdeI |
| M110 | 31 | 5'-CGGTTTTCCTGTTTAACTTCGCTATGGC TATAGAACGG CACC-3' | fds-PAcm fusion primer |
| M111 | 32 | 5'-GGGTGGCATATGAAAGTCTCCTGTGGA TGATTAAGAT CTGG-3' | NirB promoter 3'-end, NdeI |
| M112 | 33 | 5'-CCTCCATATGAAAAAACTGCTGTTCGC-3' | fd signal sequence 5'-end, NdeI |
| M120 | 34 | 5'-GATAAAGATGGCCGGGTCATCACACCA GATTCCC-3' | Anneals 94 bp upstream of NsiI site of hlyA |
| M121 | 35 | 5'-CCTCCACCGGATCCTTAACGCTCATGTA AAC-3' | Hly D 3'-end region, BamHI |
| M125 | 36 | 5'-CCTCCGCCGTGATGCATAGCCAATCTCA TAGCC-3' | PA 3'-end, removes stop codon, NsiI |

[a]Restriction enzyme sites are underlined

[b]Region of complementarity is shown in bold

Part II D

Vaccines for Immunization Against Anthrax

This invention relates broadly to a class of vaccines for the prevention of anthrax disease. A living, non-pathogenic mutant, oral vaccine strain of *Salmonella Typhi* has already been shown to be safe and effective in protecting against typhoid fever; it is a mutant, galactose epimeraseless strain of *S. Typhi* designated as Ty21a. Its preparation, safety, and efficacy as a vaccine have already been described in Germanier, R. and Furer 1975 *J Infect Dis* 131:553-558; Wandan, M. H. et al. 1980 *Bull WHO* 58:469-474.

A particular vaccine of interest according to this invention is a living, attenuated vaccine to be used to protect against *Bacillus anthracis*.

The invention encompasses functional fragments or functional variants of wild type anthrax PA. A "functional" fragment or variant, as used herein, includes a polypeptide that comprises any of a variety of changes (modifications), either naturally occurring or deliberately generated, provided that the polypeptide retains at least one epitope which allows it to be immunogenic. Preferably, the fragment or variant -retains the ability to elicit (induce) a protective response against anthrax infection. One of skill in the art can readily determine if a given fragment or variant exhibits the desired property, using conventional methods. Naturally occurring allelic variants of the PA are encompassed by the invention.

Antigens used in compositions or methods of the invention can be functional fragments of full-length proteins. Any desirable size (length) polypeptide can be used, ranging from one amino acid shorter than a wild type protein to a small peptide (e.g., about 8-10 amino acids long) bearing only a single epitope and/or antigenic sequence.

The antigens can also be functional variants. For example, variant PA polypeptides used in the invention may exhibit substantial identity to comparable portions of wild type PA. The term "substantial identity" or "substantial similarity" as used herein indicates that a polypeptide (or a nucleic acid) comprises a sequence that has at least about 90% sequence identity to a reference sequence, or preferably at least about 95%, or more preferably at least about 98% sequence identity to the reference sequence, over a comparison window of at least about 10 to about 100 or more amino acids residues or nucleotides. Methods to determine sequence identity (between nucleic acids or proteins) are conventional. Alignments can be accomplished by using any effective algorithm. For pairwise alignments of DNA sequences, the methods described by Wilbur-Lipman (e.g., Wilbur et al. 1983 *Proc Natl Acad Sci USA* 80:726-730) or Martinez/Needleman- Wunsch (Martinez 1983 *Nucleic Acid Res* 11:4629-4634) can be used. Pairs of protein sequences can be aligned by the Lipman-Pearson method (Lipman et al. 1985 *Science* 227: 1435-1441), e.g., with k-tuple set at 2, gap penalty set at 4, and gap length penalty set at 12. Various commercial and free sources of alignment programs are available, e.g., MegAlign by DNA Star, BLAST (National Center for Biotechnology Information), BCM (Baylor College of Medicine) Launcher, etc. Percent sequence identity can also be determined by other conventional methods, e.g., as described in Altschul et al. 1986 Bull Math Bio 48:603-616, and Henikoff et al. 1992 *Proc Natl Acad Sci USA* 89:10915-10919.

Variant antigens of the invention include polypeptides having one or more naturally occurring (e.g., through natural mutation) or non-naturally occurring (e.g., by deliberate modification, such as by site-directed mutagenesis) modifications, e.g., insertions, deletions, additions and/or substitutions, either conservative or non-conservative. By "conservative substitutions" is meant by combinations such as Gly, Ala; Val, Ile, Leu; Asp, Glu; Asn, Gln; Ser, Thr; Lys, Arg; and Phe, Tyr. Variants can include, e.g., homologs, muteins and minietics. The invention also encompasses variants such as polypeptides in which cysteine residues which are nonessential for biological activity are deleted or replaced with other amino acids, thereby preventing the formation of incorrect intramolecular disulfide bridges; naturally occurring variants arising from alternative mRNA splicing events; and altered forms reflecting genetic polymorphism (e.g., allelic variation). Other active variants may comprise added peptide sequences, either naturally occurring or heterologous, such as, e.g., leader, signal, secretory, targeting, enzymatic etc. sequences. Furthermore, the polypeptide can be modified by any of a variety of art-recognized modifications.

Another aspect of the invention is a method of treating a patient in need thereof, comprising administering to the patient an effective amount of an immunogenic anthrax composition (e.g., an anthrax vaccine) produced by a method of the invention. By an "effective amount" is meant herein an amount that is effective to elicit a desired response. For example, an effective amount of an immunogenic composition is an amount that is effective to elicit a detectable immune response. An effective dose can be determined empirically, according to conventional procedures, taking into account well known factors such as the age, weight, and/or clinical condition of the patient, the method of and scheduling of administration, and the like. As for other methods disclosed herein, the patient can be any animal, preferably a mammal such as, e.g., a farm or other domestic animal, or a rat, mouse, hamster, guinea pig, rabbit, etc., preferably a human.

While the present invention has been described in some detail and form for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:

1. A living attenuated vaccine, for the immunization against anthrax disease, comprising an effective dose of S. Typhi Ty21a, said S. Typhi Ty21a comprising a low-copy plasmid, which plasmid comprises a nucleic acid sequence having at least 90% sequence identity to the sequence of SEQ ID NO: 10, said sequence encoding a *Bacillus anthracis* protective antigen (PA), said plasmid further comprising a nirB promoter or an htrA promoter, and a nucleotide sequence encoding a hemolysin secretion system.

2. A vaccine according to claim 1, wherein the plasmid is pGB2.

3. A vaccine according to claim 1 in freeze-dried form.

4. A method of immunizing a susceptible host against *B. anthracis* disease comprising administering to the host an effective amount of the vaccine according to claim 1 to elicit an immunizing response.

5. The vaccine according to claim 1, wherein said *Bacillus anthracis* protective antigen (PA) is encoded by a sequence optimized for expression in said S. Typhi.

6. The vaccine according to claim 1, wherein said plasmid is a low-copy plasmid, low copy being 5-7 copies per cell.

7. A nucleic acid construct comprising
a low copy pGB2 plasmid backbone,
a nirB promoter or an htrA promoter inducible in a eukaryotic cell,
the sequence of SEQ ID NO: 10 encoding a *Bacillus anthracis* protective antigen (PA), and an encoded extracellular secretion signal sequence comprising a nucleotide sequence encoding a hemolysin secretion system.

8. A S. Typhi Ty21a comprising the nucleic acid construct of claim 7.

9. An immunogenic composition comprising the S. Typhi of claim 8.

10. A S. Typhi comprising the nucleic acid construct of claim 7.

11. An immunogenic composition comprising the S. Typhi of claim 10.

12. The nucleic acid construct according to claim 7, wherein the construct comprises an htrA promoter.

13. The vaccine of claim 1, wherein the nucleic acid sequence comprises a nucleotide sequence having at least 95% sequence identity to the sequence of SEQ ID NO: 10.

14. The vaccine of claim 13, wherein the plasmid comprises an htrA promoter.

15. The vaccine of claim 1, wherein the nucleic acid sequence comprises a nucleotide sequence having at least 98% sequence identity to the sequence of SEQ ID NO: 10.

16. The vaccine of claim 15, wherein the plasmid comprises an htrA promoter.

17. A vaccine according to claim 1, wherein the plasmid comprises the nucleic acid sequence of SEQ ID NO: 10.

18. The vaccine of claim 1, wherein the plasmid comprises an htrA promoter.

19. The vaccine of claim 1, wherein the plasmid comprises a nirB promoter.

20. The vaccine of claim 1, wherein the plasmid is a pGB2 plasmid backbone, the nucleic acid sequence comprises the nucleic acid sequence of SEQ ID NO: 10, and the promoter is an htrA promoter.

21. A nucleic acid construct comprising:
- a low copy plasmid;
- a promoter inducible in a eukaryotic cell, wherein the promoter is a nirB promoter or an htrA promoter;
- a nucleotide sequence encoding a *Bacillus anthracis* protective antigen (PA), wherein the nucleotide sequence comprises the sequence of SEQ ID NO: 10; and
- an encoded extracellular secretion signal sequence comprising a nucleotide sequence encoding a hemolysin secretion system.

* * * * *